United States Patent
Yilmaz et al.

(10) Patent No.: US 11,266,617 B2
(45) Date of Patent: Mar. 8, 2022

(54) BETA-HYDROXYBUTYRATE ENCAPSULATED PLGA NANOPARTICLE COMPOSITIONS

(71) Applicant: Massachusetts Institute of Technology, Cambridge, MA (US)

(72) Inventors: Omer Yilmaz, Cambridge, MA (US); Chia-Wei Cheng, Cambridge, MA (US); George Eng, Boston, MA (US); Fang Wang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 105 days.

(21) Appl. No.: 16/655,125

(22) Filed: Oct. 16, 2019

(65) Prior Publication Data
US 2020/0147018 A1    May 14, 2020

Related U.S. Application Data

(60) Provisional application No. 62/855,915, filed on May 31, 2019, provisional application No. 62/796,576, filed on Jan. 24, 2019, provisional application No. 62/746,149, filed on Oct. 16, 2018.

(51) Int. Cl.
| | | |
|---|---|---|
| *A61K 31/194* | (2006.01) | |
| *A61K 9/16* | (2006.01) | |
| *A61K 9/51* | (2006.01) | |
| *B82Y 5/00* | (2011.01) | |

(52) U.S. Cl.
CPC .......... *A61K 31/194* (2013.01); *A61K 9/1647* (2013.01); *A61K 9/5153* (2013.01); *B82Y 5/00* (2013.01)

(58) Field of Classification Search
CPC .. A61K 31/194; A61K 9/1647; A61K 9/5153; A61K 9/0019; A61K 31/19; B82Y 5/00; A61P 1/00
See application file for complete search history.

(56) References Cited

U.S. PATENT DOCUMENTS

2015/0250755 A1    9/2015 Veech et al.

FOREIGN PATENT DOCUMENTS

WO    2016123229 A1    8/2016

OTHER PUBLICATIONS

Errico et al, Poly(hydroxyalkanoates) Based Polymeric Nanoparticles for Drug Delivery, Journal of Biomedicine and Biotechnology, ID 571702, 10 pages. (Year: 2009).*

(Continued)

*Primary Examiner* — Carlos A Azpuru
(74) *Attorney, Agent, or Firm* — Hamilton, Brook, Smith & Reynolds, P.C.

(57) ABSTRACT

The present invention provides compositions comprising β-hydroxybutyrate, cyclic or linear β-hydroxybutyrate oligomers, and/or β-hydroxybutyrate ester derivatives, or pharmaceutically-acceptable salts thereof. In various embodiments, the compositions are encapsulated by nanoparticles, such as nanoparticles comprising, e.g., poly(lactic-co-glycolic acid). In additional embodiments, the invention provides methods of using such compositions to induce intestinal stem cell regeneration and/or treat radiation-induced intestinal damage in a subject.

5 Claims, 60 Drawing Sheets
(52 of 60 Drawing Sheet(s) Filed in Color)

(56) References Cited

OTHER PUBLICATIONS

Mihaylova et al: "Fasting Activates Fatty Acid Oxidation to Enhance Intestinal Stem Cell Function during Homeostasis and Aging", Cell Stem Cell, vol. 22, No. 5, May 1, 2018, pp. 769-778.
Stacey et al: "Radiation-induced small bowel disease: latest developments and clinical guidance", Therapeutic Advances in Chronic Disease, 2011SAGE Publications LTDGBR, vol. 5, No. 1, Jan. 1, 2014, pp. 15-29.
Notification Concerning Transmittal of International Preliminary Report on Patentability for International Application No. PCT/US2019/056611, entitled Compositions And Methods For Inducing Intestinal Stem Cell Regeneration, consisting of 14 pages, dated Apr. 29, 2021.
Notification of Transmittal of The International Search Report and Written Opinion for International Application No. PCT/US2019/056611, entitled Compositions And Methods For Inducing Intestinal Stem Cell Regeneration, consisting of 14 pages, dated Feb. 5, 2020.

\* cited by examiner

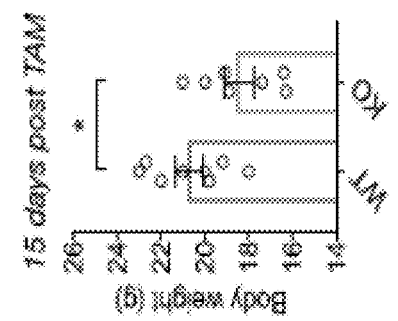
FIG. 2A
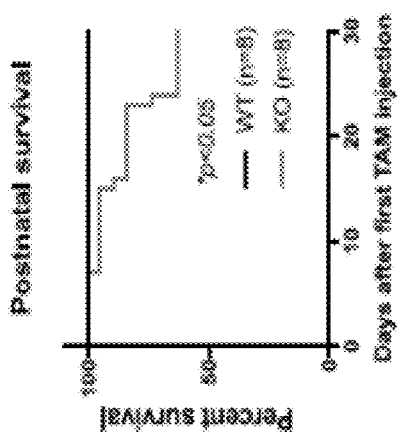
FIG. 2B
FIG. 2C
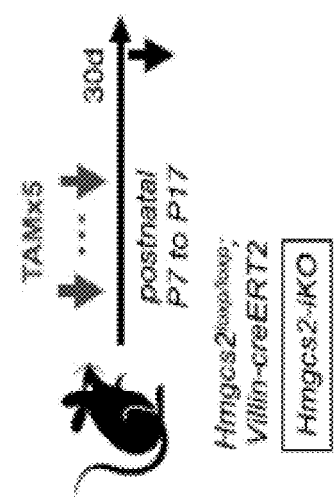
FIG. 2D
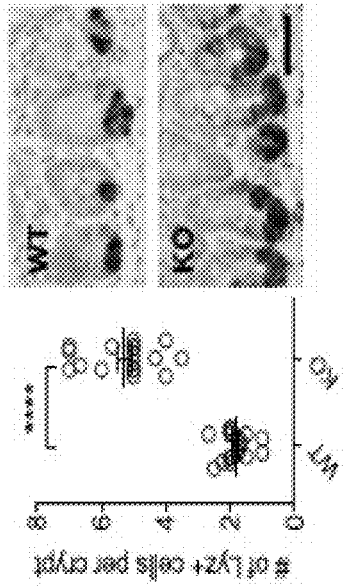
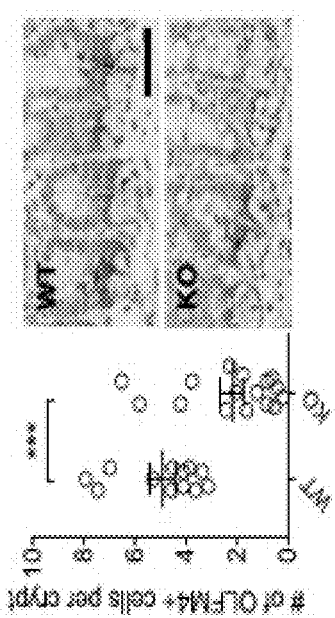
FIG. 2E

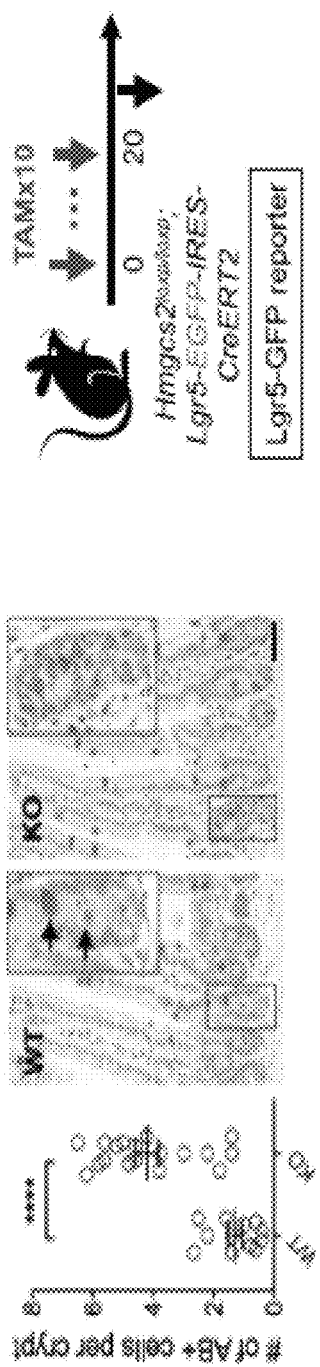
FIG. 2F
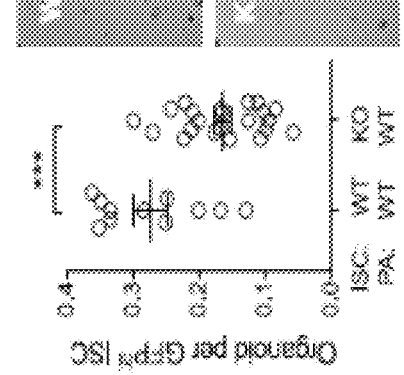
FIG. 2G
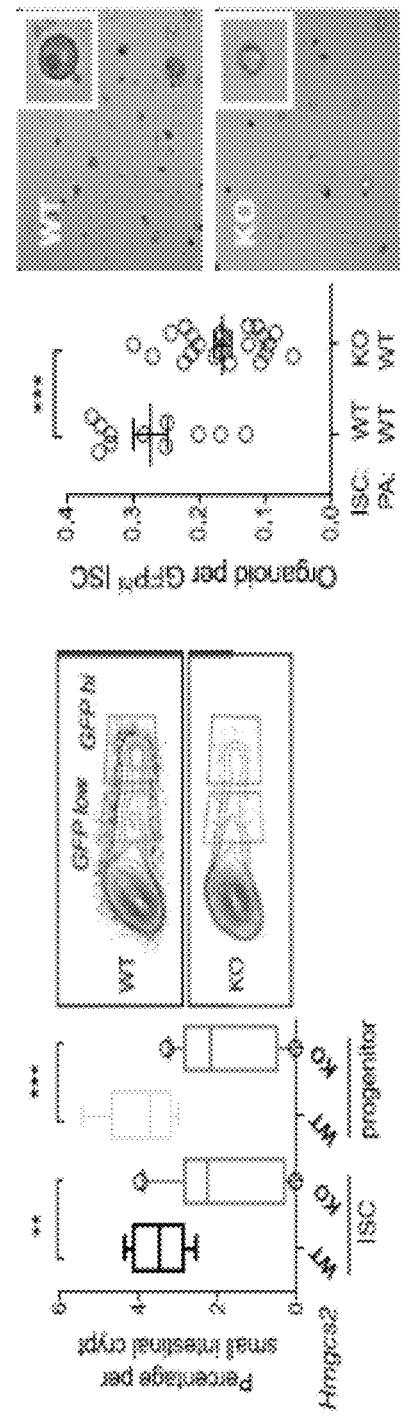
FIG. 2H
FIG. 2I

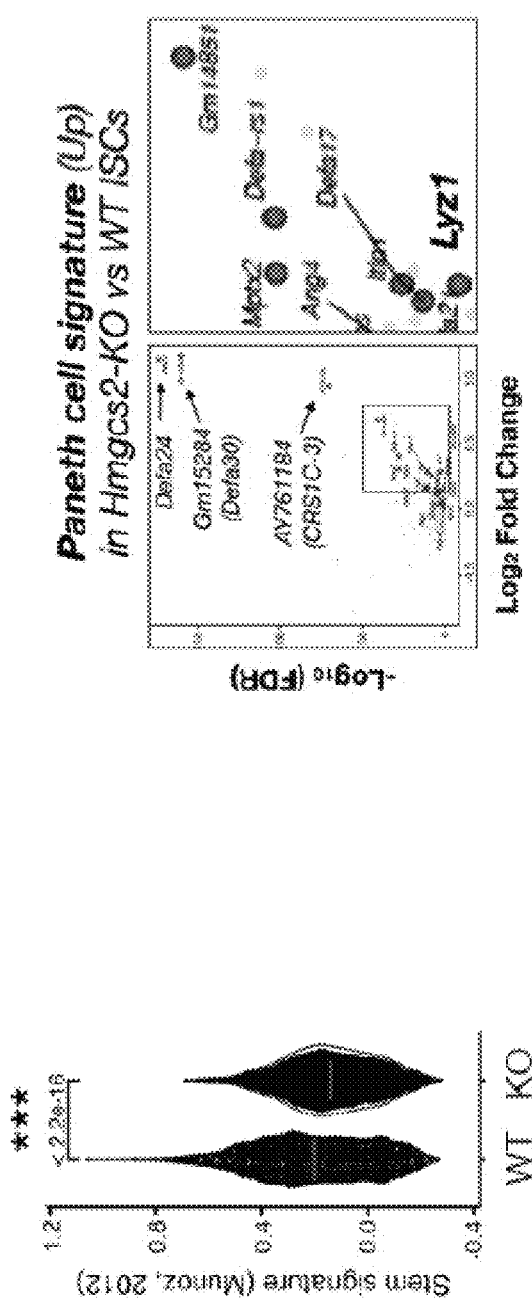
FIG. 3E
FIG. 3F
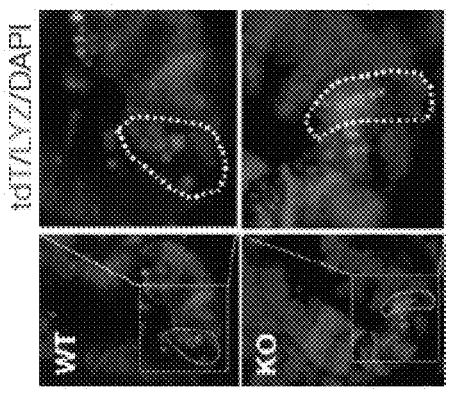
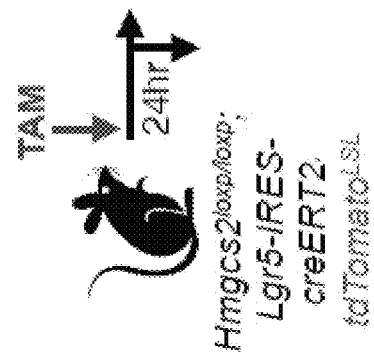
FIG. 3G

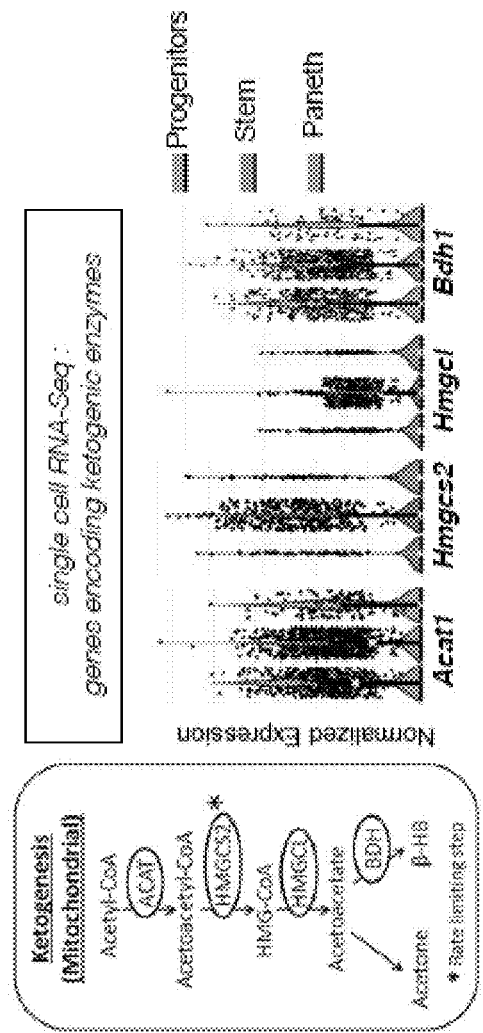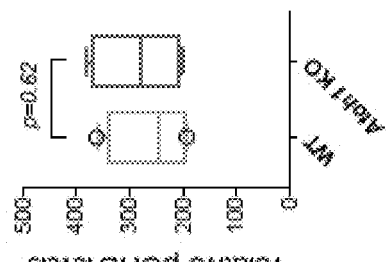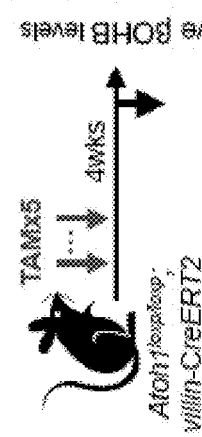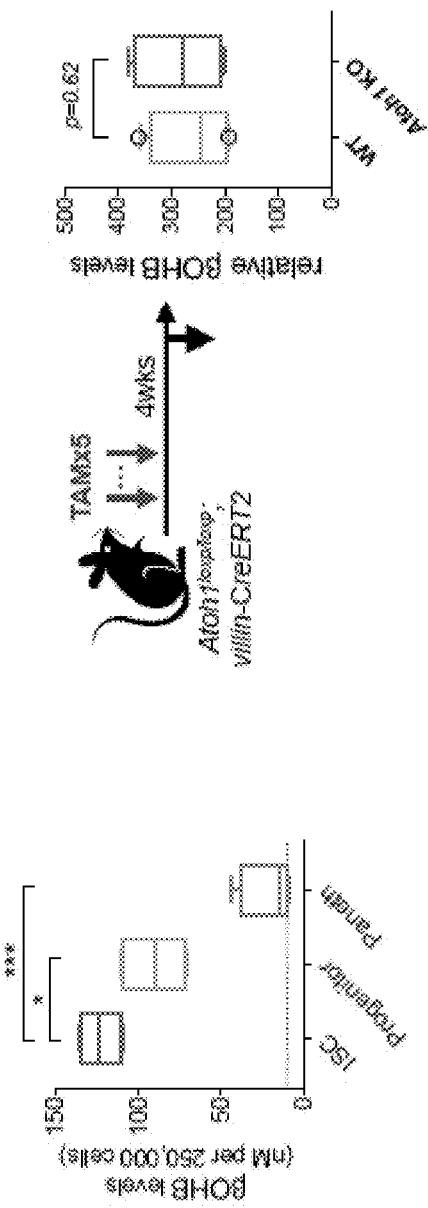
FIG. 4A
FIG. 4B
FIG. 4C

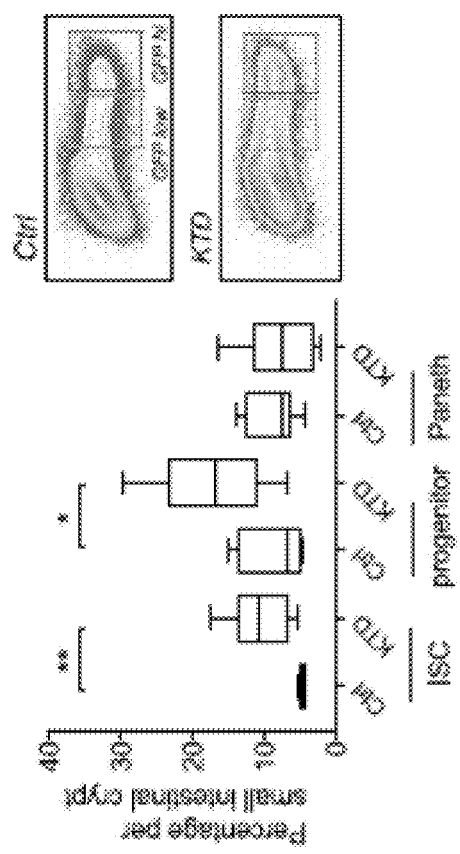
FIG. 6D
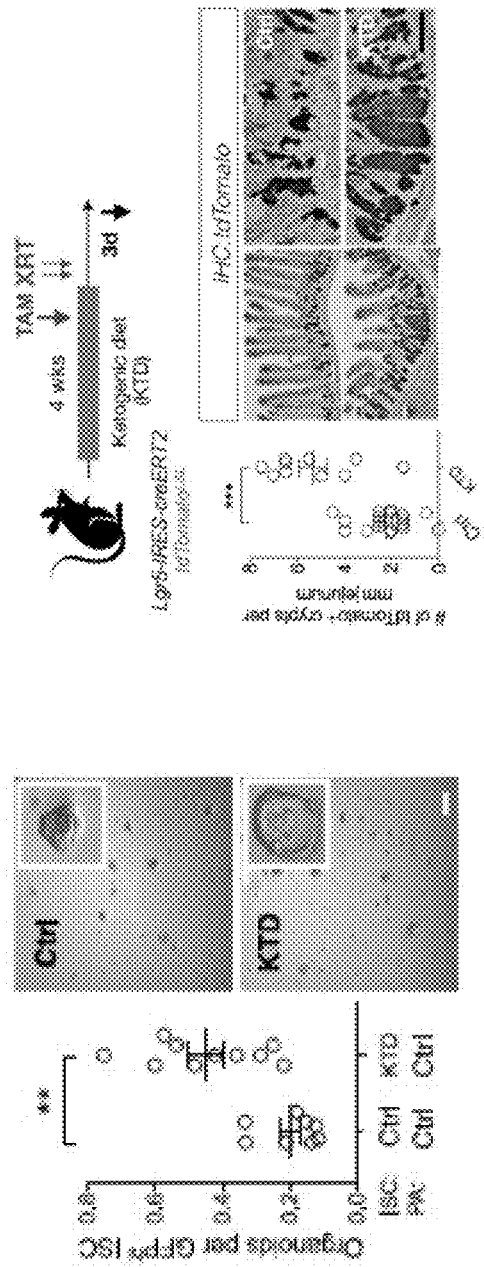
FIG. 6F
FIG. 6E

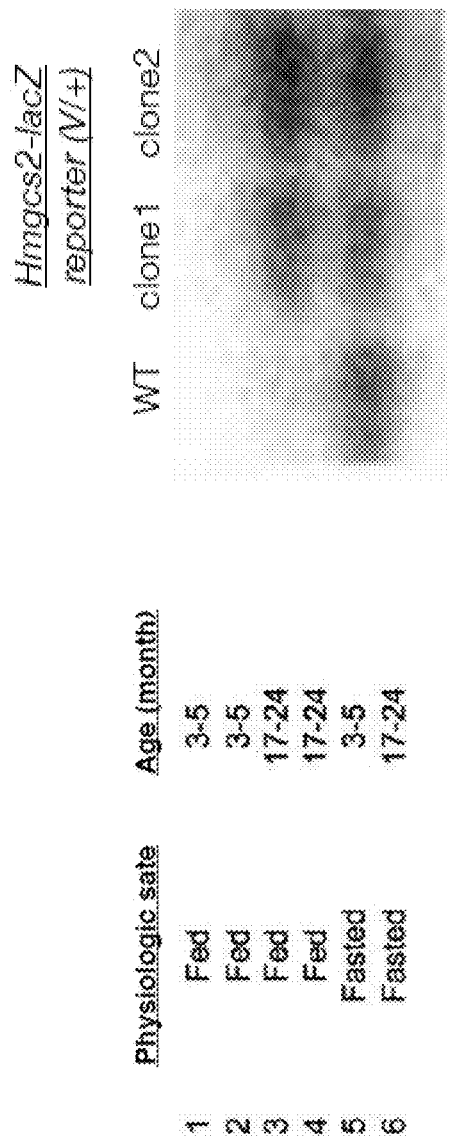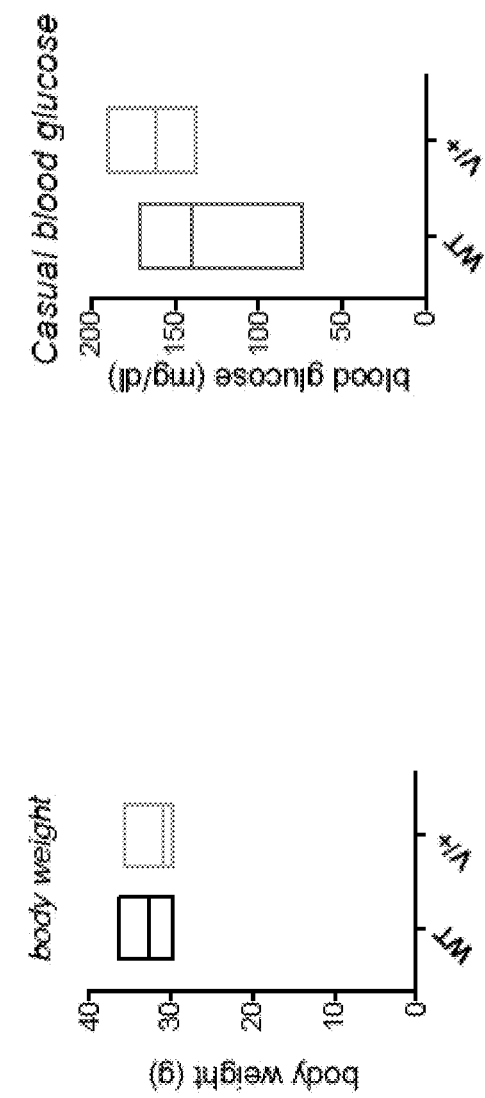
FIG. 8F
FIG. 8G
FIG. 8H
FIG. 8I

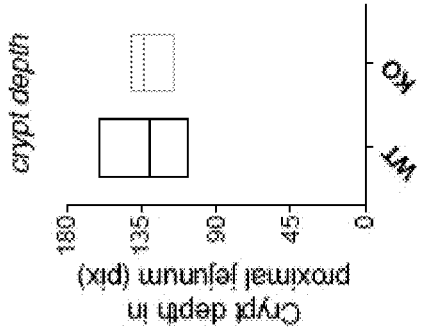
FIG. 9I
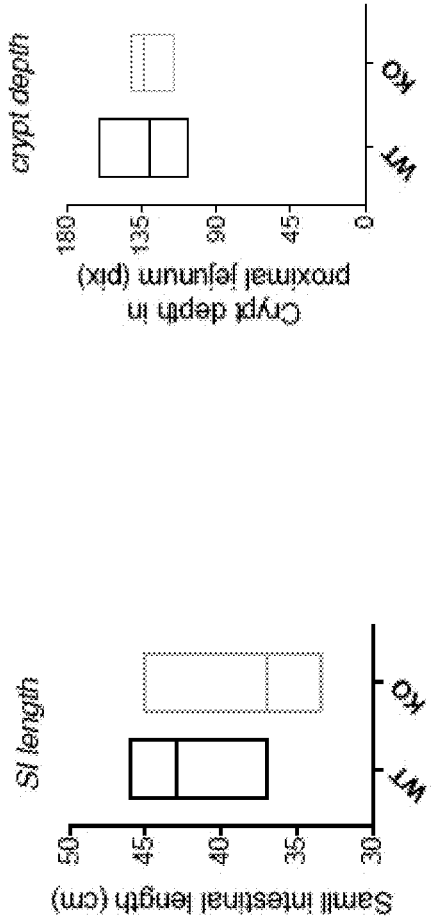
FIG. 9H
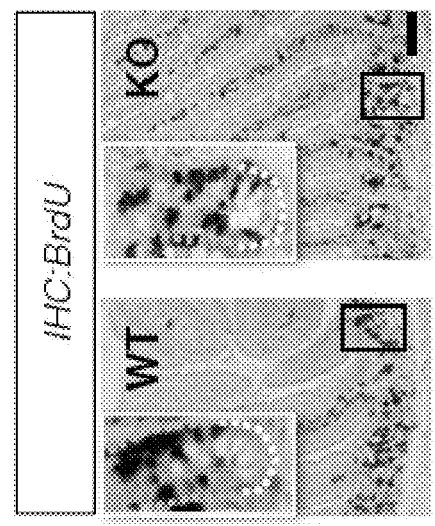
FIG. 9J
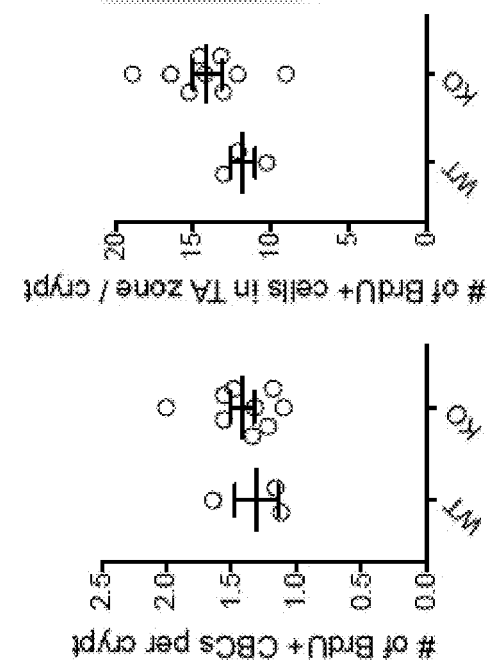

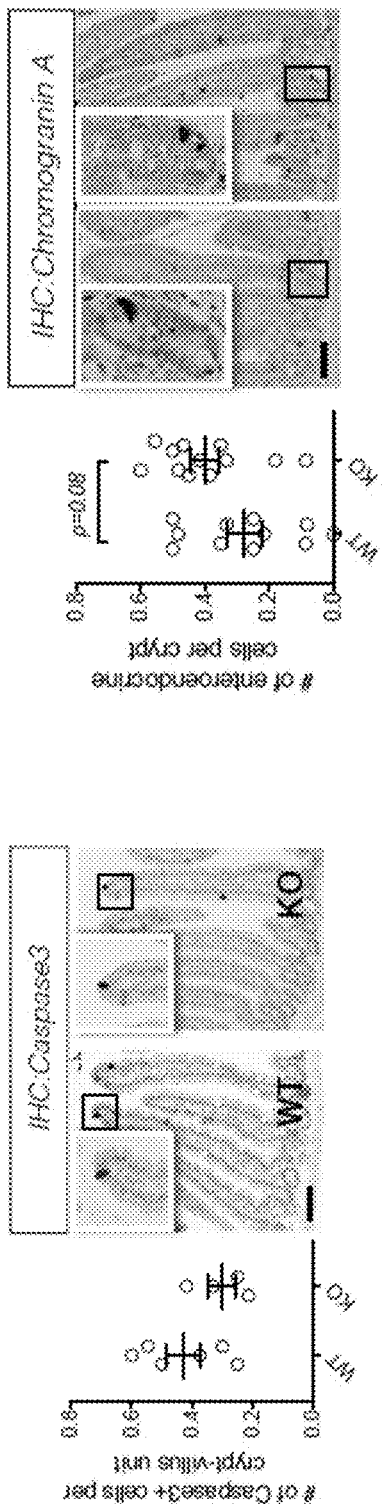
FIG. 9L
FIG. 9K
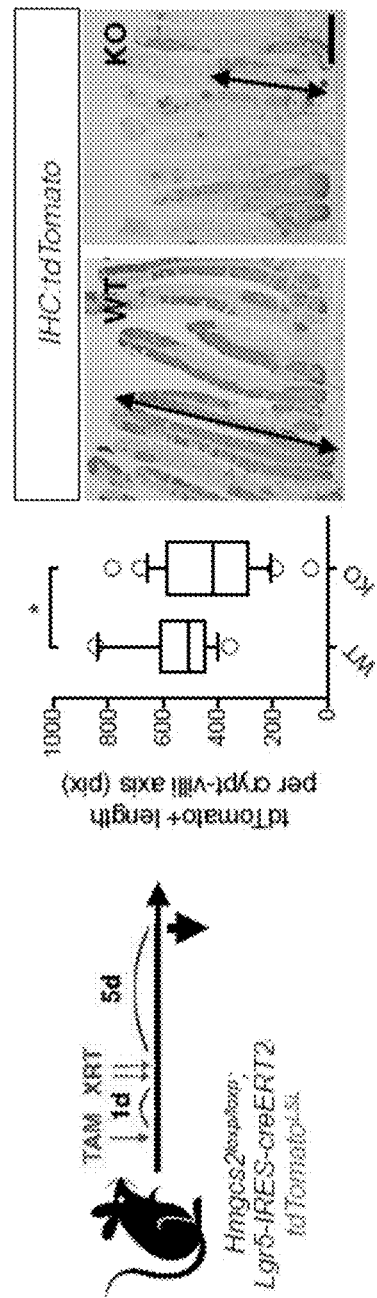
FIG. 9M

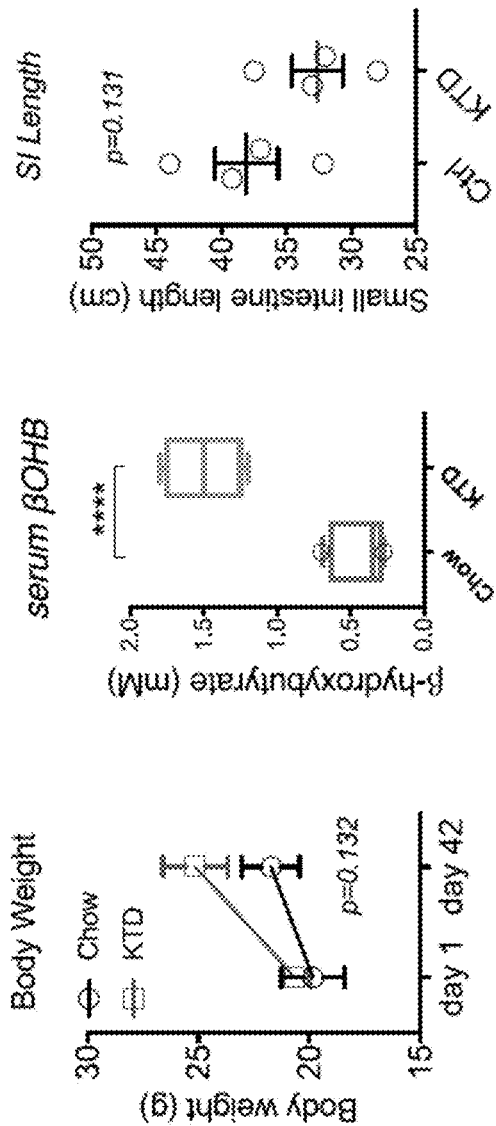
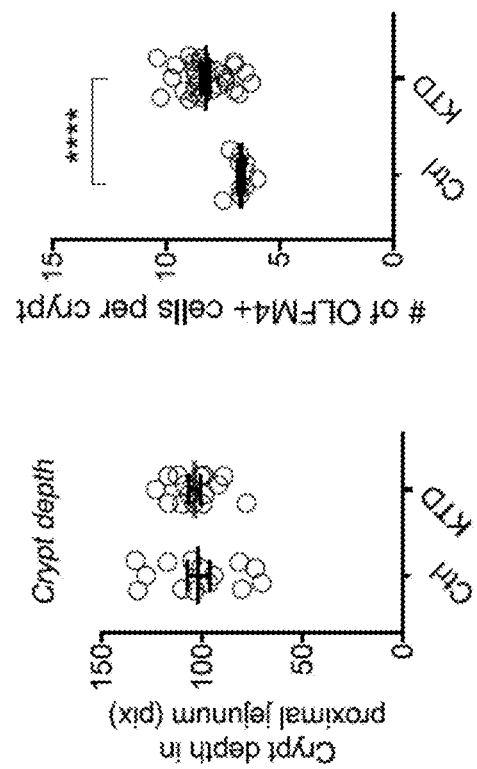
FIG. 13A
FIG. 13B
FIG. 13C
FIG. 13D
FIG. 13E

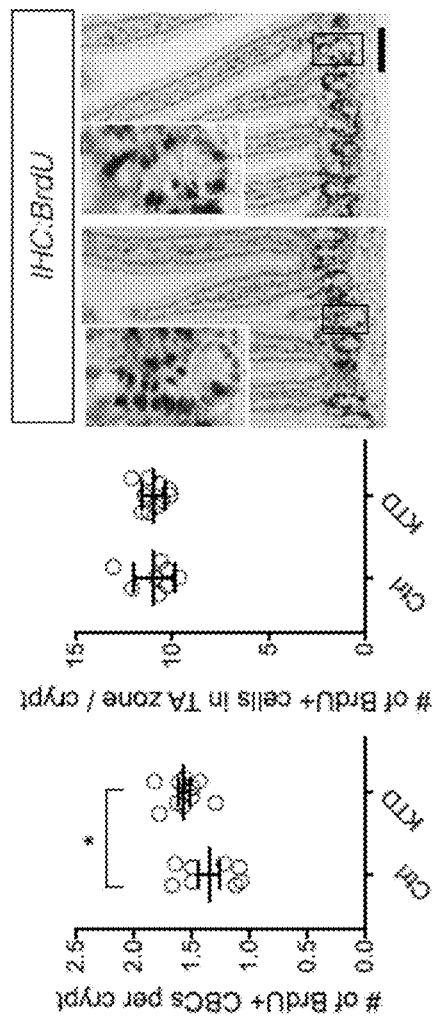
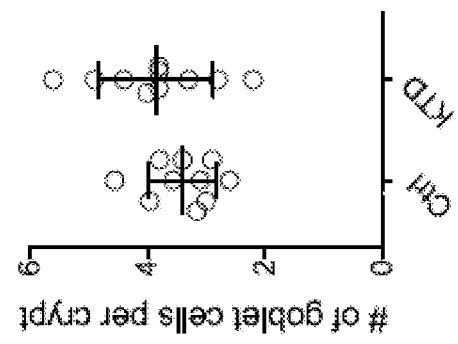
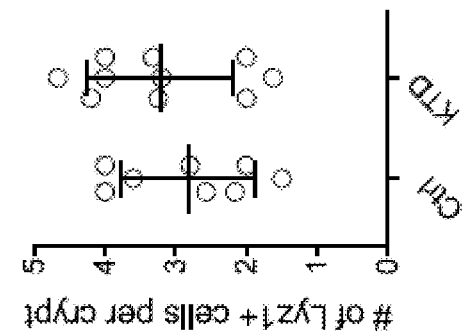
FIG. 13H
FIG. 13I
FIG. 13J

BETA-HYDROXYBUTYRATE ENCAPSULATED PLGA NANOPARTICLE COMPOSITIONS

RELATED APPLICATIONS

This application claims the benefit of U.S. Provisional Application No. 62/855,915, filed on May 31, 2019, U.S. Provisional Application No. 62/796,576, filed on Jan. 24, 2019, and U.S. Provisional Application No. 62/746,149, filed on Oct. 16, 2018. The entire teachings of the above applications are incorporated herein by reference.

GOVERNMENT SUPPORT

This invention was made with Government support under Grant Nos. AG045144, CA211184, and K99 DK123407 awarded by the National Institutes of Health (NIH). The Government has certain rights in the invention.

BACKGROUND

In the mammalian intestine, the actively cycling $Lgr5^+$ intestinal stem cells (ISCs) depend on the precise control of intrinsic regulatory programs that include the Wnt, Notch, and BMP developmental signaling pathways as well as extrinsic cues from their environment to dynamically remodel intestinal composition (Barker et al., 2007; Fre et al., 2005; Mihaylova et al., 2014; Nakada et al., 2011; Qi et al., 2017; van der Flier et al., 2009; Yan et al., 2017). $Lgr5^+$ ISCs reside at the bottom of intestinal crypts and are nestled between Paneth cells in the small intestine (Sato et al., 2011), deep secretory cells in the colon (Sasaki et al., 2016) and stromal cells throughout the small intestine and colon (Degirmenci et al., 2018; Shoshkes-Carmel et al., 2018), which comprise components of the ISC niche. These ISC niche cells elaborate myriad growth factors and ligands that determine ISC identity in part through modulation of these developmental pathways. In addition to these semi-static epithelial and stromal niche components, migratory immune cell subsets provide inputs that inform stem cell fate decisions through cytokine signaling based on external signals (Biton et al., 2018; Lindemans et al., 2015).

$Lgr5^+$ ISCs drive intestinal maintenance in homeostasis and regeneration in response to injury, such as from radiation-induced damage (Beumer and Clevers, 2016; Metcalfe et al., 2014). Accordingly, there is a need for compositions and methods that maintain or promote regeneration of $Lgr5^+$ ISCs in the human gut in subjects suffering from such injuries.

SUMMARY

The present disclosure is based, in part, on the discovery that the ketone body, β-hydroxybutyrate (βOHB), governs a diet responsive metabolite signaling axis in $Lgr5^+$ intestinal stem cells (ISCs) that modulates the Notch program to sustain intestinal stemness in homeostasis and regenerative adaptation.

In one aspect, the present disclosure provides a composition comprising β-hydroxybutyrate, or a pharmaceutically-acceptable salt thereof, encapsulated by a nanoparticle.

In another aspect, the present disclosure provides a composition comprising a 3-hydroxybutyrate ester derivative (e.g., glycerol-tri((R)-3-hydroxybutyrate)), or a pharmaceutically-acceptable salt thereof, encapsulated by a nanoparticle.

In a further aspect, the present disclosure provides a method of inducing intestinal stem cell regeneration in a subject, comprising administering an effective amount of β-hydroxybutyrate, or a pharmaceutically-acceptable salt thereof, to the subject.

In yet another aspect, the present disclosure provides a method of inducing intestinal stem cell regeneration in a subject, comprising administering an effective amount of a 3-hydroxybutyrate ester derivative (e.g., glycerol-tri((R)-3-hydroxybutyrate)), or a pharmaceutically-acceptable salt thereof, to the subject.

In another aspect, the present disclosure provides a method of treating radiation-induced intestinal damage in a subject, comprising administering an effective amount of β-hydroxybutyrate, or a pharmaceutically-acceptable salt thereof, to the subject.

In an additional aspect, the present disclosure provides a method of treating radiation-induced intestinal damage in a subject, comprising administering an effective amount of a 3-hydroxybutyrate ester derivative (e.g., glycerol-tri((R)-3-hydroxybutyrate)), or a pharmaceutically-acceptable salt thereof, to the subject.

In another aspect, the present disclosure provides a method of treating radiation-induced intestinal damage in a subject, comprising administering an effective amount of a histone deacetylase (HDAC) inhibitor to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A, Principal component analysis (PCA) for genes differentially expressed in $Lgr5\text{-}GFP^{low}$ progenitors versus $Lgr5\text{-}GFP^{hi}$ ISCs. Variance filtered by $(\rho/\rho_{max})$=5e-4; p=0.14, q=0.28; plot/total: 253/45578 variables. Axin2, axin-like protein 2; Hmgcs2, 3-Hydroxy-3-Methylglutaryl-CoA Synthase 2; Lgr5, Leucine-rich repeat-containing G-protein coupled receptor 5; Olfm4, Olfactomedin 4; n=4 mice. (see also Table S1). FIG. 1B, Mouse HMGCS2 protein expression by immunohistochemistry (IHC, brown) and Lgr5 expression by ISH (red). White-dashed line defines the intestinal crypt and black arrows indicate $HMGCS2^+$ cells. The image represents one of 3 biological replicates. Scale bar, 50 um. FIG. 1C, Human HMGCS2 protein expression by immunohistochemistry (IHC, brown). White-dashed line defines the intestinal crypt and black arrows indicate $HMGCS2^+$ cells. The image represents one of 10 biological replicates. Scale bar, 50 um. FIG. 1D, Stacked barplots show cell composition (%) of $Hmgcs2^-$, Hmgcs2-expressing, $Lgr5^-$ and Lgr5-expressing intestinal epithelial cells. Numbers in parenthesis indicate the total number (n) of the noted cell populations. FIG. 1E, Hmgcs2-lacZ reporter construct where the lacZ-tagged allele reflects endogenous Hmgcs2 expression (left). Hmgcs2-lacZ expression (blue) in the small intestine (right). The image represents one of 3 biological replicates. Scale bar, 50 um. FIG. 1F, Organoid-forming potential of flow-sorted $Hmgcs2\text{-}lacZ^-$ and $Hmgcs2\text{-}lacZ^+$ crypt epithelial cells (7AAD$^-$EpCAM$^+$). 5,000 cells from each population was flow-sorted into matrigel with crypt culture media. Arrows indicate organoids and asterisk indicates aborted organoid debris. The numbers of organoids formed from plated cells were quantified at 5 day in culture. Data represent mean+/−s.e.m. **p<0.01. n=6 samples from 3 mice. Scale bar: 20 μm.

FIGS. 2A-2L show loss of Hmgcs2 compromises ISC self-renewal and differentiation. FIG. 2A, Schematic of intestinal Hmgcs2 deletion in postnatal mice with Villin-CreERT2 (iKO) including the timeline for tamoxifen (TAM) injections and tissue collection. FIG. 2B, Kaplan-Meier survival curves of the WT and Hmgcs2-iKO mice starting the first day of tamoxifen injection. FIG. 2C, Body weights of WT and Hmgcs2-iKO mice. 15 days after first TAM injection. FIGS. 2D-F, Quantification (left) and representative images (right) of Olfactomedin 4+ (OLFM4$^+$) stem cells by IHC (FIG. 2D), Lysozyme+(LYZ+) Paneth cells by IHC and (FIG. 2E), Mucin$^+$ goblet cells by Alcian Blue (AB) (FIG. 2F) in proximal jejunal crypts. n>5 mice per group. For FIGS. 2D-2F, mice were analyzed at the age of 37 days. For FIGS. 2D-2F, Scale bars, 100 um. FIG. 2G, Schematic of Hmgcs2 deletion with Lgr5-EGFP-IRES-CreERT2 (Lgr5-GFP reporter) including the timeline for tamoxifen (TAM) injections and tissue collection. 1 day after last TAM injection (Day 21), ISCs and Paneth cells from WT or conditional Hmgcs2-null (KO) intestinal crypts were isolated using flow cytometry. FIG. 2H, Frequency of 7AAD$^-$/Epcam$^+$/CD24$^-$/Lgr5-GFP$^{hi}$ ISCs and Lgr5-GFP$^{low}$ progenitors in crypt cells from WT and KO mice by flow cytometry. n>10 mice per group. FIG. 2I, Organoid-forming assay for sorted WT and KO ISCs co-cultured with WT Paneth cells. Representative images: day 5 organoids. n>10 mice per group. Scale bar: 100 um. FIG. 2J, Schematic of the Lgr5 lineage tracing including timeline of TAM injection, irradiation (XRT, 7.5Gy×2) and tissue collection. FIGS. 2K-2L, Quantification and representative images of tdTomato+ Lgr5$^+$ ISC-derived progeny labeled by IHC for tdTomato (FIG. 2K) and number of surviving crypts assessed by the microcolony assay (FIG. 2L). Scale bar: 100 μm. n>25 crypts per measurement, n>5 measurements per mouse and n>3 mice per group. For box-and-whisker plots (FIG. 2H), the data are expressed as 10 to 90 percentiles. For dot plots (FIGS. 2C-2F, 2I, 2K and 2L), the data are expressed as mean+/−s.e.m. *p<0.05, p<0.01, *p<0.005, ****p<0.001. n>25 crypts per measurement, n>3 measurements per mouse and n>5 mice per group.

FIGS. 3A-3J show HMGCS2 regulates stemness and secretory differentiation through NOTCH signaling. FIG. 3A, Schematic of the mouse model including the timeline of tamoxifen (TAM) injection and tissue collection for single-cell RNA-seq (scRNA-seq). 5 days after TAM injection, intestinal crypts were isolated from WT and Hmgcs2-KO mice and the Lgr5+ ISC-derived tdTomato+ progeny were flow-sorted for scRNA-seq. FIG. 3B, Cell-type clusters. t-SNE was used to visualize the clustering (color coding) of 17,162 single cells (Hmgcs2-KO; n=2 mice; 7793 cells, vs WT; n=2 mice; 9369 cells), based on the expression of known marker genes (Haber et al., 2017). See also Figures S3B. EEC, enteroendocrine cells; TA, transit amplifying (progenitor) cells. FIG. 3C, Merged t-SNE plot of Tdtomato$^+$ progeny derived from WT (blue) and Hmgcs2-KO (red) ISCs. FIG. 3D, Fraction of total cells per cell type. Error bars, s.e.m.; *FDR<0.25, FDR<0.1, *FDR<0.01; χ2 test. FIG. 3E, Violin plot showing the distribution of the mean expression of the stem cell signature genes (Munoz et al., 2012a) in WT and Hmgcs2-KO ISCs. ***FDR<0.0001; Mann-Whitney U test. FIG. 3F, Volcano plot displaying differential expressed (DE) genes in Hmgcs2-KO ISCs vs. WT ISCs. 20 of 194 significantly up-regulated genes in Hmgcs2-KO ISCs are Paneth cell markers (green dots) ((Haber et al., 2017)). p<0.0001. n=2151 WT ISCs and n=2754 KO ISCs. FIG. 3G, Representative image and quantification at 24 hr after TAM injection by immunofluorescence (IF) staining: tdTomato for progeny of Lgr5$^+$ ISCs and Lysozyme (LYZ) as Paneth cell marker. n>25 crypts per measurement, n>3 measurements per mouse and n>5 mice per group. FIG. 3H, Gene set enrichment analysis of Notch-inhibition response genes (left) and Atoh1 deletion target genes (right) (Kim et al., 2014). Bar plot of the −Log$_{10}$ (p-value) indicates the gene sets up-(white) or down-regulated (gray) in Hmgcs2-KO ISCs compared to WT ISCs. FIG. 3I, Hes Family BHLH Transcription Factor 1 (Hes1) and Atonal BHLH Transcription Factor 1 (Atoh1) mRNA expression in intestinal crypts by ISH. Image represents one of 5 biological replicates per group. Yellow arrows indicate Atoh1 transcript positive cells. Scale bar: 50 um. FIG. 3J, Schematic for assessing organoid-forming ability of genetically-engineered organoid cells with the CRISPR/CAS9 mediated loss of Hmgcs2 (left) and the constitutive Notch activation by Cre-induced NICD expression (right) or both. Transfected cells were flow-sorted based on the fluorescent markers and plated onto matrigel. Organoids were quantified and imaged after 5 days of culture (n=4 measurements from 2 independent experiments). Scale bar: 200 μm. Data in the dot plot are expressed as mean+/−s.e.m. *p<0.05 and **p<0.01.

FIGS. 4A-4F show β-hydroxybutyrate (βOHB) compensates for Hmgcs2 loss in ISCs. FIG. 4A, Relative expression of genes encoding enzymes for ketogenesis in ISCs, progenitors and Paneth cells: ACAT, acetyl-CoA acetyltransferase; BDH, 3-hydroxybutyrate dehydrogenase; HMGL, HMG-CoA lyase, visualized by violin plots for scRNA-Seq data. n=6 mice. FIG. 4B, Relative β-Hydroxybutyrate (βOHB) levels in flow-sorted Lgr5-GFP$^{hi}$ ISCs, Lgr5-GFP$^{low}$ progenitors and Paneth cells. 250,000 cells of each cell population were directly sorted into the assay buffer and immediately processed for βOHB measurement. Dashed line indicates the detection limit of the colorimetric assay. n=8 samples per population from 4 mice. FIG. 4C, Schematic for Atoh1 deletion. 4 weeks after 5$^{th}$ (last) tamoxifen (TAM) injection, intestinal tissues were harvested for histology. Intestinal crypts were isolated for βOHB measurement. Quantification of βOHB levels in intestinal crypts from WT and Atoh1-KO mice. Levels of βOHB were normalized to total protein of crypt cells. n=16 samples from 8 mice per group. FIG. 4D, Schematic of the mouse model of Hmgcs2 loss. After tamoxifen (TAM) injection, intestinal tissues were harvested for histology and intestinal crypts were isolated for βOHB measurement at the indicated time points (i.e. 24 hr, 7 d and 12 d after first TAM injection). FIG. 4E, Hes1 mRNA expression in intestinal crypts by ISH at indicated timepoints after inducing Hmgcs2 loss. Image represents one of 5 biological replicates per group. FIG. 4F, Schematic (top) of the mouse model including the timeline of tamoxifen (TAM) injection, oral administration of nanoparticle PLGA encapsulated βOHB or non-encapsulated βOHB oligomers, irradiation (XRT, 7.5 Gy×2) and tissue collection. Quantification (bottom) and representative images (right) of tdTomato+ Lgr5$^+$ ISC-derived lineage (cell progenies) by IHC. Scale bar: 100 μm. n>25 crypts per measurement, n>5 measurements per mouse and n>3 mice per group. For box-and-whisker plots (FIGS. 4B-4D), data were expressed as box-and-whisker 10 to 90 percentiles. Data in dot plots were expressed as mean+/−s.e.m. *p<0.05, p<0.01, *p<0.005.

FIG. 5A, Violin plots of genes related to FIG. 12A: Notch receptor Notch1, Class I HDAC genes: HDAC1/2/3 and Notch target Hes1, based on a previously published scRNA-Seq data (Haber et al., 2017). FIG. 5B, Representative flow cytometry plots (top) and quantification of GFP expression (bottom) Hes1-GFP+ primary organoids exposed to γ-secretase inhibitor (GSI, 10 uM), βOHB (50 uM) and HDAC inhibitor (JNJ-26481585, 0.2 nM), compared to control condition. n=6 samples per treatment from n=3 mice. FIG. 5C, Organoid-forming assay for intestinal crypts isolated from WT and Hmgcs2-KO mice, with combinations of HDAC inhibitor JNJ-26481585 (JNJ) or βOHB treatments or Notch receptor inhibitor (GSI, gamma secretase inhibitor). Quantification and representative images: day-5-to-7 organoids. n=4 mice. Scale bar: 500 µm. Arrows indicate organoids and asterisks indicate aborted crypts. FIG. 5D, Schematic (top) of the mouse model including the timeline of tamoxifen (TAM) and HDACi (JNJ) injection and tissue collection. Nuclear NICD, a measure of Notch activation, by immunofluorescence (IF). Inset: arrow illustrates NICD$^{high}$ nucleus and asterisk indicates NICD$^{low}$ nucleus. Data (bottom) represents n>25 crypts per measurement, n>3 measurements per mouse and n>3 mice per group. Scale bar: 20 µm. FIG. 5E, Quantification of OLFM4$^+$ stem cells, LYZ+ Paneth cells and AB/PAS+ goblet cells in proximal jejunal crypts by IHC. FIG. 5F, Schematic of the mouse model including timeline of TAM and HDACi (JNJ) injection, irradiation (XRT, 7.5 Gy×2) and tissue collection. FIG. 5G, Quantification and representative images of tdTomato+ Lgr5$^+$ ISC-derived lineage (cell progenies) by IHC. Scale bar: 100 µm. n>25 crypts per measurement, n>3 measurements per mouse and n>5 mice per group. For box-and-whisker plots (FIG. 5C) data were expressed as box-and-whisker 10 to 90 percentiles, Data in bar graph (FIG. 5D) and dot plot (FIG. 5E and FIG. 5G) are expressed as mean+/−s.e.m. *p<0.05, p<0.01, *p<0.005, ****p<0.0001.

FIGS. 6A-6H show ketogenic diet enhances ISC self-renewal in an HMGCS2-dependent manner. FIG. 6A, Schematic (top) of the mouse model including the timeline of ketogenic diet (KTD) and tissue collection. After 3-4 weeks of the diet, intestinal tissues of KTD-fed or chow-fed (Ctrl) mice were harvested for histology, crypts culture or sorted by flow cytometry for cell frequency analysis. n>5 mice per group. HMGCS2 expression (bottom) by IHC. The image represents one of 5 biological replicates. Scale bars: 50 µm. FIG. 6B, βOHB levels in intestinal crypts from KTD- and Chow-fed mice. Levels of βOHB were normalized to total protein of crypt cells. n=12 samples from 6 mice per group. FIG. 6C, Hes1-GFP expression, a measure of Notch activation by flow cytometry, of crypt cells from KTD- and Chow-fed mice. FIG. 6D, Frequencies of Lgr5-GFP$^{hi}$ ISCs, Lgr5-GFP$^{low}$ progenitors and CD24+c-Kit+ Paneth cells in crypts from KTD- and Chow-fed mice. n=6 mice per group. FIG. 6E, Organoid-forming assay for sorted ISCs from KTD and Chow mice, co-cultured with Paneth cells from Chow mice. n=6 mice per group. representative images: day 5 organoids. Scale bar: 100 um. FIG. 6F, Schematic (top) of the Lgr5 lineage tracing including timeline of TAM injection, irradiation (XRT, 7.5 Gy×2) and tissue collection. Intestinal tissues were harvested for histology and intestinal crypts were isolated for βOHB measurement at the indicated time points. Quantification and representative images (bottom) of tdTomato+ Lgr5$^+$ ISC-derived progeny labeled by IHC for tdTomato. For G-H, Schematic (top) of intestinal Hmgcs2-deletion (iKO) and whole-body Hmgcs2-deletion (wKO) mice on KTD, including timeline of TAM injection, irradiation (XRT, 7.5 Gy×2) and tissue collection. βOHB levels (bottom) in intestinal crypts isolated from the indicated groups (FIG. 6G), number of surviving crypts assessed by the microcolony assay (FIG. 6H). For FIG. 6F and FIG. 6H, Scale bar: 100 µm. n>25 crypts per measurement, n>5 measurements per mouse and n>3 mice per group. Data in dot plots (FIG. 6C, FIG. 6E and FIG. 6F) are expressed as mean+/−s.e.m. For (FIG. 6B, FIG. 6D and FIG. 6G), Box-and-whisker 10 to 90 percentiles. *p<0.05, p<0.01, **p<0.001.

FIG. 7A, Schematic (top) of the mouse model including the timeline of glucose supplementation (Gluc) and tissue collection. After 3-4 weeks of the diet, intestinal tissues of Gluc and Ctrl mice were harvested for histology, crypts culture or sorted by flow cytometry for cell frequency analysis. n>5 mice per group. HMGCS2 expression (bottom) by IHC. The image represents one of 5 biological replicates. Scale bars: 50 µm. FIG. 7B, βOHB levels in intestinal crypts from Gluc and Ctrl mice. Levels of βOHB were normalized to total protein of crypt cells. n=12 samples from 6 mice per group. FIG. 7C, Hes1-GFP expression, a measure of Notch activation by flow cytometry, of crypt cells from Gluc and Ctrl mice. FIG. 7D-7E, Schematic (top) of the Lgr5 lineage tracing including timeline of TAM injection, irradiation (XRT, 7.5 Gy×2) and tissue collection. Quantification and representative images (bottom) of tdTomato+ Lgr5$^+$ ISC-derived progeny labeled by IHC for tdTomato (FIG. 7D) and number of surviving crypts assessed by the microcolony assay (FIG. 7E). Scale bar: 100 µm. n>25 crypts per measurement, n>5 measurements per mouse and n>3 mice per group. FIG. 7F, Model of how ketone body (βOHB) signaling dynamically regulates intestinal stemness in homeostasis and in response to diet. In normal dietary states, mitochondrial HMGSCS2-derived βOHB enforces NOTCH signaling through HDAC, class 1 inhibition. Genetic ablation of Hmgcs2 reduces ISC βOHB levels, thereby increasing HDAC-mediated suppression of the NOTCH transcriptional program, which diminishes ISC numbers, function and skews differentiation towards the secretory lineage. Ketogenic diets (KTD) enhance both systemic and stem cell produced βOHB levels in ISCs, leading to higher NOTCH activity, ISC function, and post-injury regeneration. In contrast, glucose supplemented diets suppress ketogenesis and have the opposite effects on intestinal stemness. Thus, it is proposed that dynamic control of ISC βOHB levels enables it to serve as a metabolic messenger to execute intestinal remodeling in response to diverse physiological states.

FIGS. 8A-8L show characterization of Hmgcs2 and metabolic gene expression in ISCs. Related to FIG. 1. FIG. 8A, Schematic of enzymes involved in ketogenesis. * denote the rate-limiting step. FIG. 8B, mRNA expression levels of Hmgcs2 in flow-sorted ISCs, progenitors and Paneth cells measured by quantitative PCR (qPCR). Data were expressed as box-and-whisker 10 to 90 percentiles. *p<0.05 comparing to progenitor and Paneth cells. n=5 mice. FIG. 8C, Protein expression levels of HMGCS2 in flow-sorted ISCs (Lgr5-GFP$^{hi}$), progenitors (Lgr5-GFP$^{low}$) and Paneth cells by Western blotting. Relative expression levels were measured by normalized gray values of HMGCS2/alpha-Tublin images. p<0.01 and *p<0.005. FIG. 8D, HMGCS2 protein expression in flow-sorted crypt epithelial cells (gray squares) and Lgr5+ ISCs (blue circles) by single-cell western blotting. n>250 cells per sample. (see Methods for the definition and calculation of "Peak Signal to Noise"). The absolute levels of "peak signal to noise levels of HMGCS2" are not comparable across assays (chips). The cut-off (<0.1) was set based on internal control within each assay (chip). FIG. 8E, Examples of relative expression heatmap of genes encoding rate-limiting metabolic enzymes: 3-hydroxy-3-methylglutaryl-CoA synthase 2 (Hmgcs2) for ketogenesis, Carnitine palmitoyltransferase 1A (Cpt1a) for fatty acid β-oxidation, isocitrate dehydrogenase (Idh1) for TCA cycle, glycogen synthase (Gys1) for glycogen synthesis, fructose-1,6,biphosphatase (Fbp1) for gluconeogenesis, phosphofructokinase-1 (Pfkm) for glycolysis (Rognstad, 1979; Zhao et al., 2009). See FIG. 8F for Physiologic conditions and age of mice from 6 independent experiments for Sample #1-#6. (See Data Availability) n=6 mice. FIG. 8G, Southern blot analysis to screen Hmgcs2 heterozygous-knockout (Hmgcs2$^{v/+}$) ES clones. The WT allele (lane 1) gave a band of 9-kb, while the Hmgcs2$^{v/+}$ allele (lane 2 and 3) gave a 9- and a 12-kb bands. Image is representative of 25 clones. H-1, Compared to WT mice, Hmgcs2$^{v/+}$ mice showed no difference in body mass (FIG. 8H), non-fasting blood glucose levels from tail-tip sample (FIG. 8I), serum βOHB levels based on LC/MS metabolomics analysis (FIG. 8J), small intestine length (FIG. 8K) and crypt depth in the jejunum (FIG. 8L), n>5 mice per group. Approximate Age: 3-6 months.

FIGS. 9A-9M show Hmgcs2 loss perturbs sternness and differentiation in the intestine. Related to FIG. 2. FIG. 9A, Schematic of the mouse model with the timeline for tamoxifen (TAM) injections and tissue collection. FIG. 9B, Excision confirmation by PCR. WT band: 1392 bp; excision band: 408 bp; Floxed band (239 bp) was not detectable. Image represents n>5 mice per group. FIG. 9C, Organoid area from ISCs co-cultured with Paneth cells at day 5. FIG. 9D, Schematic of the mouse model with the timeline for TAM injections and tissue collection. FIG. 9E, IHC for HMGCS2 and tdTomato F, Excision confirmation by PCR after TAM at indicated time. Images represent one of 5 biological replicates per group. FIG. 9G, Schematic of the mouse model including the timeline for TAM injection and tissue collection. 1, 7, 12 and 17 days after a single TAM injection, small intestine tissues were collected for histology. Quantification of OLFM4+ cells in proximal jejunal crypts by IHC. n>25 crypts per measurement, n>3 measurements per mouse and n>5 mice per group. Numbers of LYSOZYME+ (LYZ+) Paneth cells in proximal jejunal crypts by IHC, MUCIN+ goblet cells in proximal jejunal crypts by Alcian Blue (AB) and Periodic Acid Schiff's (PAS) staining. n>25 crypts per measurement, n>3 measurements per mouse and n>5 mice per group. For (FIGS. 9H-9L), Compared to WT intestines, Hmgcs2-null intestines have no difference in FIG. 9H, length of intestine; FIG. 9I, crypt depth in jejunum; FIG. 9J, BrdU+ ISCs and progenitors, 4 hours after BrdU administration; FIG. 9K, Caspase 3+ apoptotic cells per crypt-villus unit; FIG. 9L, Chromogranin A+ enteroendocrine cells per proximal jejunal crypts, 17 days after TAM injection. FIG. 9M, Schematic of the mouse model with timeline of TAM injection, irradiation (XRT, 7.5 Gy×2) and tissue collection. Quantification and representative images of tdTomato+ progeny derived from Lgr5+ ISCs assessed by IHC. For box-and-whisker plots (FIGS. 9C, 9F, 9G and 9L), the data are expressed as 10 to 90 percentiles. Data in dot plots are expressed as mean+/−s.e.m. Scale bars: 100 um. n>5 mice per group. Approximate Age: 3-6 months.

FIG. 10A, QC metrics (Methods) and FIG. 10B, Cell-type signatures. The relative expression level (row-wise Z score of log 2 (TPM+1), where TPM denotes transcripts per million; color scale) of genes (rows) across cells (columns) is shown, sorted by type (Methods). FIG. 10C, Feature heat maps for genes encoding secretory lineage markers: Muc2, Mucin2, oligomeric Mucus/Gel-Forming; Lyz1, lysozyme1; Reg4, regenerating Family Member 4; and that of stem cell markers: Leucine-rich repeat-containing G-protein coupled receptor 5 (Lgr5), Olfactomedin 4 (Olfm4) and Achaete-Scute Family BHLH Transcription Factor 2 (Ascl2). FIGS. 10D-10F, Violin plots for mean expression of feature genes of (FIG. 10D) Paneth cell signature, (FIG. 10E) apoptosis and (FIG. 10F) proliferation in WT vs. Hmgcs2-KO stem cell clusters. FIG. 10G, Split channel images of immunofluorescence (IF) staining: tdTomato+ for Lgr5+ ISCs progeny and Lysozyme (LYZ) as Paneth cell marker. FIG. 10H, Schematic (left) of the mouse model with timeline of TAM injection and tissue collection for FACS analysis. 6 day after last TAM injection, intestinal crypts were isolated from mice and the tdTomato+ progeny of WT and Hmgcs2-KO ISCs were analyzed using flow cytometry (right). Frequency of Lgr5-GFP$^{hi}$ ISCs, Lgr5-GFP$^{low}$ progenitors and CD24+c-Kit+ Paneth cells in tdTomato+ crypt cells were quantified by flow cytometry.

FIG. 11A, Schematic of the mouse model for intestinal Cpt1a deletion with the timeline for tamoxifen (TAM) injections and tissue collection.

FIG. 12A, Enrichment plots generated by GSEA analysis for Lgr5-GFP$^{hi}$ against Lgr5-GFP$^{low}$, based on gene sets from the Reactome Pathway Database (NOTCH1 Intracellular Domain Regulates Transcription). FIG. 12B, βOHB levels in intestinal crypts from fed and fasted mice. Levels of βOHB were normalized to total protein of crypt cells. FIG. 12C, Venn diagram analysis of lysine H3K27 acetylation (H3K27ac) sites in fed and fasted (24 h) mice. FIG. 12D, Barplot displaying genomic localization of H3K27ac sites in promoter (within −/+5 kbTSS) and enhancer (outside −/+5 kbTSS) regions in fed and fasted mice. FIG. 12E, Genome browser view of ChIP-seq tracks for H3K27ac on the Hes7 locus in fed and fasted mice. FIG. 12F, Organoid-formation assay for the indicated treatments. Number of organoids per intestinal crypt quantified at 3-to-5 day. JNJ, Quisinostat (JNJ-26481585); MS-275, Entinostat (MS-275); TSA, Trichostatin A. FIG. 12G, Deletion of HDAC1 assessed by flow cytometry (top) and organoid-forming assay (bottom) for genetically-engineered primary organoid cells with i) Hmgcs2-deletion by Cre-loxp deletion, ii) Hdac1 deletion by CRISPR/Cas9 or both i and ii. Transfected cells were sorted based on the fluorescent markers and plated onto matrigel (Method). Organoids were quantified and imaged on day 5 (n=4 measurements from 2 independent experiments). Scale bars: 200 μm. FIG. 12H, Schematic of the mouse model with the timeline of tamoxifen (TAM), HDACi (JNJ) injection and tissue collection. Immunofluorescence (IF) for nuclear H3K27ac in WT, Hmgcs2-KO and Hmgcs2-KO+HDACi. Data represents n>25 crypts per measurement, n>3 measurements per mouse and n>3 mice per group. FIG. 12I, Representative images of OLFM4+ stem cells, LYZ+ Paneth cells and AB/PAS+ goblet cells in proximal jejunal crypts by immunohistochemistry (IHC). The image represents one of 5 biological replicates. Scale bar: 50 μm, Data in the bar graph (FIG. 12B and FIG. 12F) and dot plot (FIG. 12C) are expressed as mean+/−s.e.m. For (FIG. 12D), box-and-whisker 10 to 90 percentiles. *p<0.05, p<0.01, **p<0.001.

FIGS. 13A-13M shows characterization of the effects of a ketogenic diet on ISC and organoids. Related to FIG. 6. FIG. 13A, body weight, FIG. 13B, plasma β-hydroxybutyate levels, FIG. 13C, small intestine length, FIG. 13D, intestinal crypt depth, FIG. 13E, Quantification and representative images of OLFM4+ cells in proximal jejunal crypts by IHC. FIG. 13F, Nuclear NICD, a measure of Notch activation, by IF. Data represents n>25 crypts per measurement, n>3 measurements per mouse and n>3 mice per group. FIG. 13G, Organoid per crypt from KTD and Ctrl mice. n=6 mice per group. Representative images: day 3 organoids. Scale bar: 500 μm. For (FIGS. 13H-13K), proliferating (BrdU+) cells in the stem cell zone (CBC) and progenitor (TA) zone (FIG. 13H), LYZ+ Paneth cells (FIG. 13I), AB/PAS+ goblet cells (FIG. 13J), CHGA+ enteroendocrine cells (FIG. 13K) in the intestinal crypts were determined in mice fed a ketogenic diet (KTD) or a chow for 4-to-6 weeks (Methods). FIG. 13L, AB+ (goblet cells) cells normalized to organoid area in wild-type (i.e. naïve) organoids with or without the addition of βOHB. For box-and-whisker plots (FIG. 13B, FIG. 13F and FIG. 13L), the data are expressed as 10 to 90 percentiles. For dot plots, the data are expressed as mean+/−s.e.m. *p<0.05, ****p<0.001. Scale bars for histology images: 50 μm. Data represents n>25 crypts per measurement, n>3 measurements per mouse and n>3 mice per group. 13M, Schematic of Hmgcs2 deletion in Lgr5-IRES-creERT2 mice (Lgr5-iKO) on KTD (left). Number of AB/PAS+ goblet cells (middle) and organoid-forming capacity (right) of crypts from indicated group. WT, WT chow-fed mice. KO, Hmgcs2 Lgr5-iKO chow-fed mice. KO:KTD, Hmgcs2 Lgr5-iKO KTD-fed mice.

FIG. 14A, body weight, For (FIGS. 14B-14D), Quantification and representative images of FIG. 14B, OLFM4+ cells in proximal jejunal crypts by IHC. FIG. 14C, LYSOZYME+ (LYZ+) Paneth cells in proximal jejunal crypts by IHC and FIG. 14D, MUCIN+ goblet cells in proximal jejunal crypts by Alcian Blue (AB) and Periodic Acid Schiff's (PAS) staining. n>25 crypts per measurement, n>3 measurements per mouse and n>5 mice per group. Scale bar, 50 um.

DETAILED DESCRIPTION

A description of example embodiments follows.

Although significant progress has been made in deciphering how transcription factors or interactions with the niche exert executive control on Lgr5+ ISC identity, more investigation is needed to delineate how changes in the ISC microenvironment interplay with stem cell metabolism to control stemness programs. Furthermore, while recent studies suggest that exogenous nutrients couple diet to adult stem cell activity, little is known about how systemic or stem cell generated endogenous metabolites that become highly enriched in Lgr5+ ISCs coordinate cell fate decisions.

The studies disclosed herein demonstrate that the ketone body, β-hydroxybutyrate (βOHB), governs a diet responsive metabolite signaling axis in Lgr5+ intestinal stem cells (ISCs) that modulates the Notch program to sustain intestinal stemness in homeostasis and regenerative adaptation.

Figure 20:
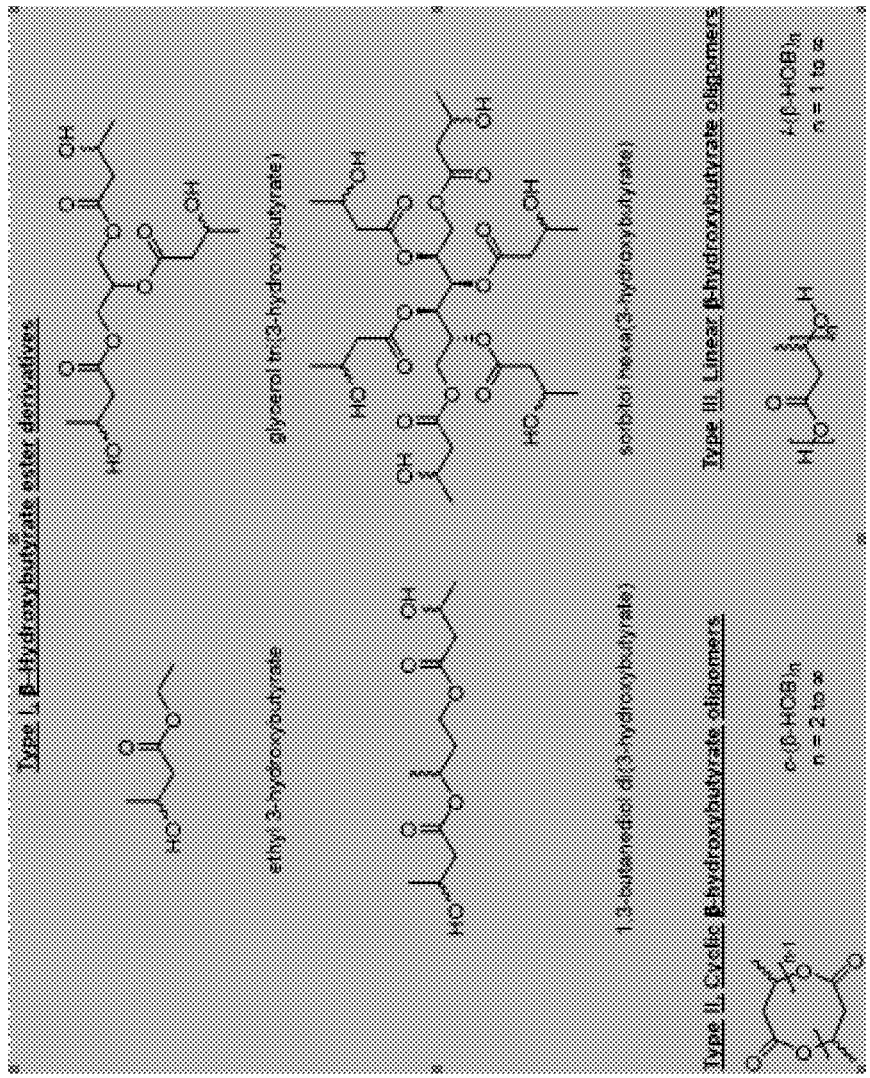
FIG. 20 shows the chemical structure of various β-hydroxybutyrate oligomers and ester derivatives.

Accordingly, in one aspect, the present disclosure provides compositions, e.g., a pharmaceutical composition(s), comprising β-hydroxybutyrate, or a pharmaceutically-acceptable salt thereof, encapsulated by a nanoparticle. The β-hydroxybutyrate can be monomeric β-hydroxybutyrate, β-hydroxybutyrate linear oligomers (e.g., FIG. 20—Type III compounds) or cyclic oligomers (e.g., FIG. 20—Type II compounds), as described further herein.

When β-hydroxybutyrate is provided in linear polymeric or oligomeric form, the β-hydroxybutyrate polymer can comprise 2 or more β-hydroxybutyrate monomers, such as about 5 or more (e.g., 2, 3, 4, 5, 6, 7, 8, 9, 10 or more) β-hydroxybutyrate monomers.

When β-hydroxybutyrate is provided in cyclic oligomeric form, the β-hydroxybutyrate oligomer can comprise between 2 and about 200 β-hydroxybutyrate monomers (e.g., 2 monomers, 3 monomers, 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, 20 monomers). In some embodiments, the compositions disclosed herein include cyclic oligomers of β-hydroxybutyrate consisting of 2 (diolide), 3 (triolide), 4 (tetraolide), 5 (pentolide), 6 (hexolide), or 7 (heptolide) β-hydroxybutyrate monomers.

In a further aspect, the present disclosure provides compositions, e.g., a pharmaceutical composition(s), comprising a 3-hydroxybutyrate ester derivative, or a pharmaceutically-acceptable salt thereof, encapsulated by a nanoparticle. In a particular embodiment, the a 3-hydroxybutyrate ester derivative is glycerol-tri((R)-3-hydroxybutyrate).

Release of β-hydroxybutyrate (e.g., in monomeric, polymeric or oligomeric form) or β-hydroxybutyrate ester derivatives from the nanoparticles in the compositions disclosed herein is a function of overall surface area, molecular weight of the polymer, the block co-polymer substituents and other non-modifiable variables such as temperature and solvent. Thus, β-hydroxybutyrate release kinetics can be tuned by modifying the non-constant variables.

For example, increasing the lactic to glycolic ratio from 50:50 to 75:25 with all other properties equal, will lead to a slower hydrolysis rate, and lead to a more extended release profile. Polymer materials ranging from 95:5 to 5:95 lactic to glycolic acid ratios are readily available, and provide a simple means to greatly alter the release kinetics.

The nanoparticles in the compositions disclosed herein can range in size from about 1 nm to about 1,000 nm. In some embodiments, the nanoparticles in the compositions disclosed herein range in size from about 50 nm to about 100 nm. The nanoparticles used in the Cheng et al [PMID: 31442404] had an average diameter of 100 nm. Modifying the sonication energy input can lead to alterations in nanoparticle size. Therefore, for the same amount of PLGA with encapsulated βOHB, the aggregate surface area would be greatly decreased if the average diameter of particle were increased, also leading to a prolonged release profile. The average molecular weight of the bulk polymer, even for a specific lactic to glycolic ratio can also be altered. Increasing the average molecular weight from what was used 5,000 Da to 45,000 Da would also prolong the release kinetics.

In some embodiments, the nanoparticles in the compositions disclosed herein comprise poly(lactic-co-glycolic acid) (PLGA). However, the substituent block co-polymer materials used in the nanoparticles can be varied. Other readily applicable polymeric substituents include, e.g., polycaprolactone, polyethylene glycol, and polyhydroxybutyrate itself. These can each be used to modify the final polymer composition to alter degradation rates, bioavailability and circulation times. PEGylation, for example, is often used to increase circulation times of bound molecules due to decreased enzymatic activity on the conjugate molecule.

The compositions disclosed herein can include lyophilized nanoparticles. The lyophilized particles are generally shelf stable for an extended period of time, typically ranging from months to years. They are compatible with almost any biocompatible excipient and are be able to return to colloidal suspension in most aqueous solutions. The nanoparticles are typically a colloidal suspension, similar to propofol, and thus can have special handling parameters, such as limited exposure to high shear stress, high heat ~100 degrees Celsius, or very small filters.

In some embodiments, the compositions of the present disclosure are pharmaceutical compositions comprising at least one active ingredient (e.g., β-hydroxybutyrate, or a pharmaceutically-acceptable salt thereof, or a 3-hydroxybutyrate ester derivative, such as glycerol-tri((R)-3-hydroxybutyrate), or a pharmaceutically acceptable salt thereof), in combination with one or more pharmaceutically or physiologically acceptable carriers, excipients or diluents. A "pharmaceutically acceptable carrier" or "pharmaceutically acceptable excipient" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like, and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012). Generally, a pharmaceutically acceptable carrier is an ingredient in a pharmaceutical composition, other than an active ingredient, which is nontoxic to the subject.

A pharmaceutically acceptable carrier can include, but is not limited to, a buffer, excipient, stabilizer, or preservative. Examples of pharmaceutically acceptable carriers include solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation Such pharmaceutical compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

As used herein, "pharmaceutically acceptable salts" refers to salts derived from suitable inorganic and organic acids and bases that are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable acid addition salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate and xinafoate salts.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, or copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Examples of organic amines include, but are not limited to, isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., Remington: The Science and Practice of Pharmacy, 22nd Edition, Pharmaceutical Press, London, UK (2012), the relevant disclosure of which is hereby incorporated by reference in its entirety.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., Remington: The Science and Practice of Pharmacy, 22nd Edition, Pharmaceutical Press, London, UK (2012), the relevant disclosure of which is hereby incorporated by reference in its entirety.

Compositions of the present disclosure can be formulated for a variety of means of parenteral or non-parenteral administration. In one embodiment, the compositions can be formulated for oral administration. Formulations suitable for oral administration can include liquid solutions, capsules, sachets, tablets, lozenges, and troches, powders liquid suspensions in an appropriate liquid and emulsions.

In one embodiment, the compositions can be formulated for infusion or intravenous administration. Compositions disclosed herein can be provided, for example, as sterile liquid preparations, e.g., isotonic aqueous solutions, emulsions, suspensions, dispersions, or viscous compositions, which may be buffered to a desirable pH.

The compositions disclosed herein can include, or be used in conjunction with, one or more additional therapeutic agents or therapies. In some embodiments, the compositions disclosed herein further comprise one or more histone deacetylase (HDAC) inhibitors. Examples of HDAC inhibitors suitable for use in this invention are known in the art and include, for example, disclosed in U.S. Pat. No. 9,238,028, the relevant contents of which are incorporated herein by reference. In some embodiments, the HDAC inhibitor is selective for class I HDACs. In other embodiments, the HDAC inhibitor is selective for class II HDACs.

In some embodiments, the compositions disclosed herein further comprise one or more PPAR-δ agonists. Examples of PPAR-δ agonists suitable for use in this invention are known in the art, and include, for example, PPAR-δ agonists disclosed in Mihaylova, M. M., et al., *Cell Stem Cell.* 2018 May 3; 22(5): 769-778.e4, the relevant contents of which are incorporated herein by reference.

In certain embodiments, the one or more additional therapeutic agents (e.g., HDAC inhibitor) are encapsulated in a nanoparticle, as described herein, with the β-hydroxybutyrate, 3-hydroxybutyrate ester derivative (e.g., glycerol-tri((R)-3-hydroxybutyrate)), or pharmaceutically-acceptable salt thereof. In other embodiments, the one or more additional therapeutic agents (e.g., HDAC inhibitor) are present in the same composition as the β-hydroxybutyrate, 3-hydroxybutyrate ester derivative (e.g., glycerol-tri((R)-3-hydroxybutyrate)), or pharmaceutically-acceptable salt thereof, but are not encapsulated in nanoparticles.

In another aspect, the present disclosure provides methods of inducing intestinal stem cell regeneration in a subject in need thereof, comprising administering an effective amount (a therapeutically effective amount) of β-hydroxybutyrate (e.g., in monomeric, polymeric or oligomeric form), or a pharmaceutically-acceptable salt thereof, to the subject. In some embodiments, the β-hydroxybutyrate (e.g., in monomeric, polymeric or oligomeric form), or pharmaceutically-acceptable salt thereof, is encapsulated in a nanoparticle, as described herein.

In a further aspect, the present disclosure provides methods of inducing intestinal stem cell regeneration in a subject in need thereof, comprising administering an effective amount (a therapeutically effective amount) of a 3-hydroxybutyrate ester derivative (e.g., glycerol-tri((R)-3-hydroxybutyrate)), or a pharmaceutically-acceptable salt thereof, to the subject. In some embodiments, the 3-hydroxybutyrate ester derivative, or pharmaceutically-acceptable salt thereof, is encapsulated in a nanoparticle, as described herein. In some embodiments, the 3-hydroxybutyrate ester derivative is glycerol-tri((R)-3-hydroxybutyrate).

In another aspect, the present disclosure provides methods of treating radiation-induced intestinal damage in a subject in need thereof, comprising administering an effective amount (a therapeutically effective amount) of β-hydroxybutyrate (e.g., in monomeric, polymeric or oligomeric form), or a pharmaceutically-acceptable salt thereof, to the subject. In some embodiments, the β-hydroxybutyrate (e.g., in monomeric, polymeric or oligomeric form), or pharmaceutically-acceptable salt thereof, is encapsulated in a nanoparticle, as described herein.

"Radiation-induced intestinal damage" is a well-known condition that includes radiation enteritis, radiation enteropathy, radiation mucositis, pelvic radiation disease, and radiation-induced bowel (e.g., small bowel) disease, any of which can be readily diagnosed by a skilled medical professional. Causes and symptoms of radiation-induced intestinal damage are disclosed in Stacey and Green, Radiation-induced small bowel disease: latest developments and clinical guidance, *Ther Adv Chronic Dis.* 2014 January; 5(1): 15-29, and Ashburn and Kalady, Radiation-Induced Problems in Colorectal Surgery, *Clin. Colon Rectal Surg.* 2016 June; 29(2): 85-91, the relevant contents of which references are incorporated herein by reference.

In a further aspect, the present disclosure provides methods of treating radiation-induced intestinal damage in a subject in need thereof, comprising administering an effective amount (a therapeutically effective amount) of 3-hydroxybutyrate ester derivative (e.g., glycerol-tri((R)-3-hydroxybutyrate)), or a pharmaceutically-acceptable salt thereof, to the subject. In some embodiments, the 3-hydroxybutyrate ester derivative (e.g., glycerol-tri((R)-3-hydroxybutyrate)), or pharmaceutically-acceptable salt thereof, is encapsulated in a nanoparticle, as described herein. In some embodiments, the 3-hydroxybutyrate ester derivative is glycerol-tri((R)-3-hydroxybutyrate).

In yet another aspect, the present disclosure provides methods of treating radiation-induced intestinal damage in a subject in need thereof, comprising administering an effective amount (a therapeutically effective amount) of a histone deacetylase (HDAC) inhibitor to the subject. In some embodiments, the HDAC inhibitor is administered with an effective amount (a therapeutically effective amount) of β-hydroxybutyrate (e.g., in monomeric, polymeric or oligomeric form), or a pharmaceutically-acceptable salt thereof, or an effective amount of glycerol-tri((R)-3-hydroxybutyrate) or other 3-hydroxybutyrate ester derivatives, or pharmaceutically-acceptable salt thereof, is encapsulated in a nanoparticle, as described herein. When an HDAC inhibitor and other active agent are administered in combination, the administration can be sequential (in either order) or concurrent (in separate compositions or in the same composition).

The terms "treat" or "treatment" or "treating" refer to therapeutic treatment wherein the object is to slow down (lessen) an undesired physiological change, or provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if a subject was not receiving treatment. Those in need of treatment include those subjects already with the undesired physiological change or disease as well as those subjects prone to have the physiological change or disease, e.g., intestinal damage.

A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved well-being of the patient or increase/regeneration of intestinal stem cells.

When a therapeutically effective amount is indicated, the precise amount of the compositions of the present disclosure to be administered can be determined by a physician with consideration of individual differences in age, weight, extent of intestinal damage, and condition of the subject.

As used herein, the term "subject" refers to an animal (e.g., a human). The terms "subject" and "patient" may be used interchangeably herein in reference to a subject. As such, a "subject" includes a human that is being treated for a condition or disease (e.g., radiation-induced intestinal damage), or prevention of a condition or disease, as a patient. As used herein, a subject (e.g., a human) is "in need of" a treatment if such subject would benefit biologically, medically or in quality of life from such treatment.

The methods described herein may be used to treat an animal subject belonging to any classification. Examples of such animals include mammals. Mammals, include, but are not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). In one embodiment, the mammal is a human.

Delivery systems useful in the context of embodiments of the invention may include time-released, delayed release, and sustained release delivery systems such that the delivery of the compositions occurs prior to, and with sufficient time to cause, sensitization of the site to be treated. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775; 4,667,014; 4,748,034; and 5,239,660 and (b) diffusional systems in which an active component permeates at a controlled rate from a polymer such as described in U.S. Pat. Nos. 3,854,480 and 3,832,253. In addition, pump-based hardware delivery systems can be used, some of which are adapted for implantation.

The administration of the compositions may be carried out in any manner, e.g., by parenteral or nonparenteral administration, including by aerosol inhalation, injection, infusions, ingestion, transfusion, implantation or transplantation. For example, the compositions described herein may be administered to a patient orally, trans-arterially, intradermally, subcutaneously, intranodally, intramuscularly, by intravenous (i.v.) injection, or intraperitoneally.

In one aspect, the compositions are administered orally. In one aspect, the compositions of the present disclosure are administered by i.v. injection. In one aspect, the compositions of the present disclosure are administered to a subject by intradermal or subcutaneous injection.

The dosage administered to a patient having irradiation induced intestinal damage is sufficient to alleviate or at least partially arrest the damage being treated ("therapeutically effective amount"). The dosage of the above treatments to be administered to a subject will vary with the precise nature of the condition being treated and the recipient of the treatment. The scaling of dosages for human administration can be performed according to practices generally accepted in the art.

In one embodiment, the subject (e.g., human) receives an initial administration of composition of the disclosure, and one or more subsequent administrations, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the composition is administered to the subject (e.g., human) per week, e.g., 2, 3, or 4 administrations of the compositions are administered per week. In one embodiment, the subject receives more than one administration of the composition per week (e.g., 2, 3 or 4 administrations per week) (also referred to herein as a cycle), followed by a week of no administrations, and then one or more additional administration of the composition (e.g., more than one administration of the composition per week) is administered to the subject. In another embodiment, the subject receives more than one cycle of the composition, and the time between each cycle is less than 10, 9, 8, 7, 6, 5, 4, or 3 days. In one embodiment, the composition is administered every other day for 3 administrations per week. In one embodiment, the composition is administered for at least two, three, four, five, six, seven, eight or more weeks.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The composition may be administered in the methods of the invention by maintenance therapy, such as, e.g., once a week for a period of 6 months or more.

EXEMPLIFICATION

Materials:
Animal

Figure 2K:
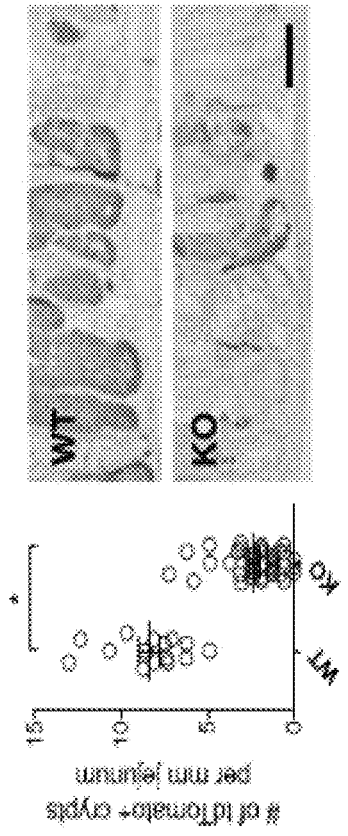
Figure 9A:
Figure 9B:
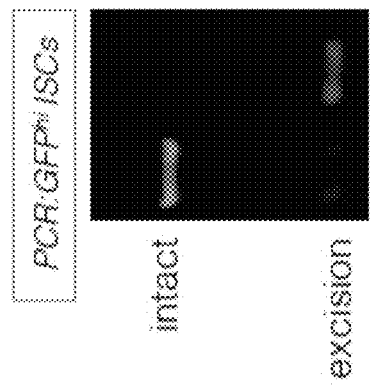
Figure 9C:
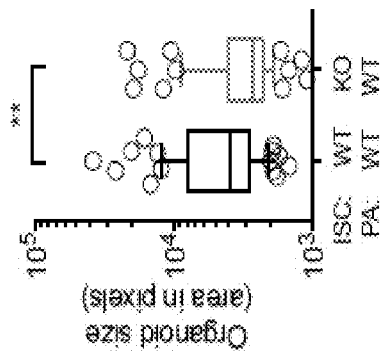
Figure 9D:
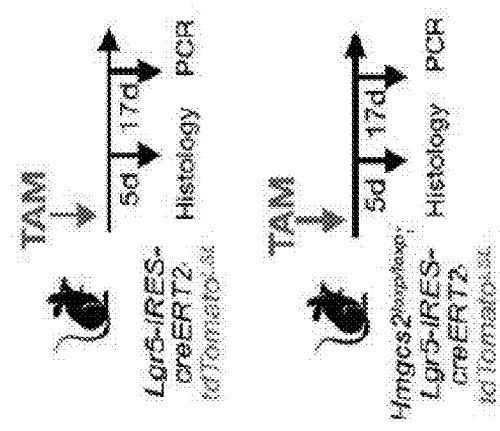
Figure 9E:
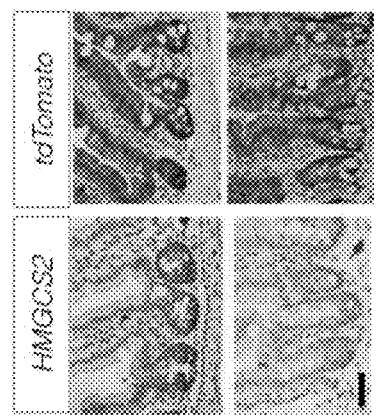

Mouse strains. Hmgcs2-lacZ reporter and conditional loxp mice were generated using a knockout-first strategy (Skarnes et al., 2011) to functionally validate whether Hmgcs2-expressing cells harbor function ISC activity and whether Hmgcs2 is necessary for ISC maintenance. The knockout-first combines the advantage of both a reporter-tagged and a conditional mutation. Briefly, a cassette containing mouse En2 splicing acceptor (SA), LacZ, and promoter-driven neomycin resistant gene (Neo) is inserted in introns of target genes. The initial allele (Hmgcs2-Vector, V) (KOMP: PG00052_Z_4_A06) is predicted to generate a null allele through splicing to the LacZ trapping element. Targeted clones therefore report endogenous gene expression and carry null mutation (FIGS. 2A and 9A). Successful targeting was validated by Southern blotting and PCR analysis (FIG. 9B). Conditional alleles (Hmgcs2-loxP, L) can be generated by removal of the gene trap cassette using Flp recombinase. To investigate the necessity of Hmgcs2 in maintaining ISC functions, Hmgcs2$^{loxp/loxp}$ mice were generated and crossed them to Lgr5-eGFP-IRES-CreERT2 (Barker et al., 2007) and to Lgr5-CreERT2; tdTomatoLSL (Huch et al., 2013) reporter mice separately. CRE-mediated excisions in sorted GFP+ cells and in tdTomato+ crypt cells were both confirmed by PCR (FIGS. 9B and 9E). Lgr5-CreERT2; tdTomatoLSL were generated by crossing Lgr5-IRES-CreERT2 mice (a gift from Dr. Hans Clevers) (Huch et al., 2013) to tdTomatoLSL mice (Jackson Laboratory, #007909). Hmgcs2$^{loxp/loxp}$; Villin-CreERT2 mice were generated by crossing Hmgcs2$^{loxp/loxp}$ mice to Villin-CreERT2 mice (el Marjou et al., 2004). Atoh1(Math1)$^{L/L}$; Villin-CreERT2 mice were generated by crossing Atoh1(Math1)$^{L/L}$ mice to Villin-CreERT2 mice (Shroyer et al., 2007). Hes1-GFP reporter mice were previously described (Lim et al., 2017). In this study, both male and female mice were used at the ages of 3-5 months unless otherwise specified in the figure legends.

Organoids

Hes1-GFP organoids were generated from adult male and female Hes1-GFP reporter mice (Lim et al., 2017). Primary NICD-GFP$^{LSL}$ organoids were generated from adult male Rosa$^{N1-IC}$ mice (Jackson Laboratory, #008159). Primary organoids were cultured in the CO2 incubator (37° C., 5% CO2) using the complete crypt culture medium, as described in METHOD DETAILS: Crypt Isolation and culturing) (Mihaylova et al., 2018).

Human Intestinal Samples

Human duodenal biopsies that were diagnosed as normal were obtained from 10 patients (n=4 19-to-20-year-old females, n=3 81-to-84-year-old females and n=3 19-to-20-year-old males). The MGH Institutional Review Board committee approved the study protocol.

Method Details
In Vivo Treatments

Tamoxifen treatment. Tamoxifen injections were achieved by intraperitoneal (i.p.) tamoxifen injection suspended in sunflower seed oil (Spectrum S1929) at a concentration of 10 mg/ml, 250 ul per 25 g of body weight, and administered at the time points indicated in figures and figure legends. Irradiation experiments. Mice were challenged by a lethal dose of irradiation (7.5 Gy×2, 6 hours apart). Intestine tissues were collected for histology 5 days after ionizing radiation-induced (XRT). Exogenous βOHB treatments: Mice received a single oral dose of βOHB-encapsulated PLGA nanoparticles (16.67 mg/25 g in 500 ul) or βOHB oligomers (15 mg/25 g in 500 ul) 16 hrs prior to irradiation. See also supplemental methods for preparation of βOHB nanoparticles and oligomers. HDAC inhibitor treatments. Mice received up to 5 injections (i.p.) of vehicle (2% DMSO+30% PEG 300+ddH2O) or Quisinostat (JNJ-26481585) 2HCl (1 mg/kg per injection). Ketogenic diet (KTD). Per-calorie macronutrient content: 15 kcal protein, 5 kcal carbohydrate and 80 kcal fat per 100 kcal KTD (Research diet, Inc. D0604601). See Supplemental Table 4 of Cheng, C.-W., Ketone Body Signaling Mediates Intestinal Stem Cell Homeostasis and Adaptation to Diet, Cell 178, 1115-1131, Aug. 22, 2019, the contents of which are incorporated herein by reference in their entirety, for the ingredient composition. Food was provided ad libitum at all times. The fat sources are Crisco, cocoa butter, and corn oil. Glucose solution. Glucose supplement was prepared by adding 13 g D-(+)-Glucose (Sigma, Cat. #G8270) into 100 ml drinking water of mice. Unless otherwise specified in figure legends, all experiments involving mice were carried out using adult male and female mice (n>3 per group), with approval from the Committee for Animal Care at MIT and under supervision of the Department of Comparative Medicine at MIT. See also QUANTIFICATION AND STATISTICAL ANALYSIS for general information related to experimental design.

β-Hydroxybutyrate (βOHB) Measurements

Serum βOHB. Blood was obtained via submandibular vein bleed (10-40 uL). Blood was collected into an Eppendorf tube and allowed to clot for 15-30 minutes at room temperature. Serum was separated by centrifugation at 1500×g for 15 min at 4° C. Serum samples were frozen at −80° C. until thawed for assay. Crypts βOHB. Intestinal crypts freshly isolated in PBS were aliquoted into two samples. Samples were pelleted (centrifuged at 300×g for 5 minutes) and re-suspended in lysis buffer of BCA assay (Thermofisher, #23225) for measuring total proteins and that for β-hydroxybutyrate measurements (Cayman, #700190). Level of crypts βOHB was normalized to total proteins of each sample.

Crypt Isolation and Culturing

As previously reported and briefly summarized here (Mihaylova et al., 2018), small intestines were removed, washed with cold PBS, opened longitudinally and then incubated on ice with PBS plus EDTA (10 mM) for 30-45 min. Tissues were then moved to PBS. Crypts were then mechanically separated from the connective tissue by shaking or by scraping, and then filtered through a 70-μm mesh into a 50-mL conical tube to remove villus material and tissue fragments. Isolated crypts for cultures were counted and embedded in Matrigel™ (Corning 356231 growth factor reduced) at 5-10 crypts per μL and cultured in a modified form of medium as described previously (Sato et al., 2009; Yilmaz et al., 2012). Unless otherwise noted, crypt culture media consists of Advanced DMEM (Gibco) that was supplemented with EGF 40 ng mL$^{-1}$ (PeproTech), Noggin 200 ng mL$^{-1}$ (PeproTech), R-spondin 500 ng mL$^{-1}$ (R&D, Sino Bioscience or (Ootani et al., 2009)), N-acetyl-L-cysteine 1 μM (Sigma-Aldrich), N2 1× (Life Technologies), B27 1× (Life Technologies), CHIR99021 3 μM (LC laboratories), and Y-27632 dihydrochloride monohydrate 10 μM (Sigma-Aldrich). Intestinal crypts were cultured in the above-mentioned media in 20-25 μL droplets of Matrigel™ were plated onto a flat bottom 48-well plate (Corning 3548) and allowed to solidify for 20-30 minutes in a 37° C. incubator. Three hundred microliters of crypt culture medium was then overlaid onto the Matrigel™, changed every three days, and maintained at 37° C. in fully humidified chambers containing 5% $CO_2$. Clonogenicity (colony-forming efficiency) was calculated by plating 50-300 crypts and assessing organoid formation 3-7 days or as specified after initiation of cultures. β-Hydroxybutyrate (Sigma, 54965), Quisinostat (JNJ-26481585) 2HCl (Selleckchem, S1096), Entinostat (MS-275) (Selleckchem, S1053), Trichostatin A (Selleckchem, 51045) and γ-secretase inhibitor MK-0752 (Cayman Chemical Company, 471905-41-6) were added into cultures as indicated in the figure legends. Plasmids for Hdac1 CRISPR-deletion (sc-436647), Cre-expression (sc-418923), Cre-expression and Hmgcs2 CRISPR-deletion (VB180615-1103gue) were used for organoid transfection according to manufacturers' instructions.

If not directly used for cultures, crypts were then dissociated into single cells and sorted by flow cytometry. Isolated ISCs or progenitor cells were centrifuged at 300 g for 5 minutes, re-suspended in the appropriate volume of crypt culture medium and seeded onto 20-25 μl Matrigel™ (Corning 356231 growth factor reduced) containing 1 μM JAG-1 protein (AnaSpec, AS-61298) in a flat bottom 48-well plate (Corning 3548). Alternatively, ISCs and Paneth cells were mixed after sorting in a 1:1 ratio, centrifuged, and then seeded onto Matrigel™. The Matrigel™ and cells were allowed to solidify before adding 300 μL of crypt culture medium. The crypt media was changed every third day.

RT-PCR and In Situ Hybridization 25,000 cells were sorted into Tri Reagent (Life Technologies), and total RNA was purified according to the manufacturer's instructions with following modification: the aqueous phase containing total RNA was purified using RNeasy plus kit (Qiagen). RNA was converted to cDNA with cDNA synthesis kit (Bio-Rad). qRT-PCR was performed with diluted cDNA (1:5) in 3 wells for each primer and SYBR green master mix on Roche LightCycler® 480 detection system. Primers used are previously described[6]. Single-molecule in situ hybridization was performed using Advanced Cell Diagnostics RNAscope 2.0 HD Detection Kit (Fast Red dye) for the following probes: Mm-Hmgcs2, Mm-Hes1, Mm-Atoh1, Mm-Lgr5. For IHC and ISH co-staining, after signal detection of Lgr5 ISH, slides were dried and proceeded with regular IHC for HMGCS2 staining.

Immunostaining and Immunoblotting

As previously described (Beyaz et al., 2016; Rickelt and Hynes, 2018; Yilmaz et al., 2012), tissues were fixed in 10% formalin, paraffin embedded and sectioned. Antigen retrieval was performed with Borg Decloaker RTU solution (Biocare Medical) in a pressurized Decloaking Chamber (Biocare Medical) for 3 minutes. Antibodies used for immunohistochemistry: rabbit anti-HMGCS2 (1:500, Abcam ab137043), rat anti-BrdU (1:2000, Abcam 6326), rabbit monoclonal anti-OLFM4 (1:10,000, gift from CST, clone PP7), rabbit polyclonal anti-lysozyme (1:250, Thermo RB-372-A1), rabbit anti-chromogranin A (1:4,000, Abcam 15160), rabbit Cleaved Caspase-3 (1:500, CST #9664), rabbit polyclonal anti-RFP (1:500, Rockland 600-401-379), goat polyclonal anti-Chromogranin A (1:100, Santa Cruz sc-1488). Biotin-conjugated secondary donkey anti-rabbit or anti-rat antibodies were used from Jackson ImmunoResearch. The Vectastain Elite ABC immunoperoxidase detection kit (Vector Labs PK-6101) followed by Dako Liquid DAB+ Substrate (Dako) was used for visualization. Antibodies used for immunofluorescence: tdTomato and Lysozyme immunofluorescence costaining, Alexa Fluor 488 and 568 secondary antibody (Invitrogen). For NICD and H3K27ac staining, antibodies rabbit anti-Cleaved Notch1 (CST, #4147), rabbit anti-H3K27ac (CST, #8173) and TSA™ Alexa Fluor 488 tyramide signal amplification kit (Life Technologies, T20948) was used. Slides were stained with DAPI (2 μg/mL) for 1 min and covered with Prolong Gold (Life Technologies) mounting media. All antibody incubations involving tissue or sorted cells were performed with Common Antibody Diluent (Biogenex). The following antibodies were used for western blotting: anti-HMGCS2 (1:500, Sigma AV41562) and anti-alpha tubulin (1:3000, Santa Cruz sc-8035). Single cell western blotting was performed using Proteinsimple Milo™ system according to manufacturer's instructions. Anti-HDAC1 antibody (1:200, ab53091) was used to detect HDAC1 levels by flow cytometry and analyzed using FlowJo.

$^{13}C$-Palmitate Labeling and LC/MS Methods

13C-Palmitate labeling assay were performed as previously described in (Mihaylova et al., 2018). Briefly, intestinal crypts were isolated from mice and incubated in RPMI media containing above mentioned crypt components and 30 mM $^{13}C$-Palmitate for 60 minutes and metabolites were extracted for LC/MS analysis.

Population RNA-Seq Analysis

Reads were aligned against the mm10 murine genome assembly, with ENSEMBL 88 annotation, using v. STAR 2.5.3a, with flags --runThreadN 8 --runMode alignReads --outFilterType BySJout --outFilterMultimapN-max 20 --alignSJoverhangMin 8 --alignSJDBoverhangMin 1 --outFilterMismatchNmax 999 --alignIntronMin 10 --alignIntronMax 1000000 --alignMatesGapMax 1000000 --outSAMtype BAM SortedByCoordinate --quant-Mode TranscriptomeSAM pointing to a 75 nt-junction STAR genome suffix array (Dobin et al., 2013). Quantification was performed using RSEM with flags --forward-prob 0 --calc-pme --alignments -p 8 (Li and Dewey, 2011). The resulting posterior mean estimates of read counts were retrieved and used for differential expression analysis using the edgeR package, in the R 3.4.0 statistical framework (McCarthy et al., 2012). In the absence of replicates, pair-wise comparisons of samples/conditions were performed using an exact test with a dispersion set to bcv-squared, where bcv value was set to 0.3. For pooled analyses (with samples pooled by their ISC, Progenitor or Paneth cell status), exact tests were similarly performed, with dispersions estimated from the data using the estimateDisp function. Benjamini-Hochberg adjusted p-values and log 2-fold-changes were retrieved and used for downstream analyses.

GSEA Analysis of Bulk RNA-Seq

The command-line version of the GSEA tool (Subramanian et al., 2005) was used to analyze potential enrichment of interesting gene sets affected by age, diet, etc. Genes were ranked according to their log 2(FoldChange) values and analyzed using the "pre-ranked" mode of the GSEA software using the following parameters: -norm meandiv -nperm 5000 -scoring_scheme weighted -set_max 2000 -set_min 1 -rnd_seed timestamp. The MSigDB C2 collection was analyzed and the c2 dataset was plotted using GSEA.

Droplet scRNA-Seq

Cells were sorted with the same parameters as described above for flow-cytometry into an Eppendorf tube containing 50 μl of 0.4% BSA-PBS and stored on ice until proceeding to the Chromium Single Cell Platform. Single cells were processed through the Chromium Single Cell Platform using the Chromium Single Cell 3' Library, Gel Bead and Chip Kits (10× Genomics, Pleasanton, Calif.), following the manufacturer's protocol. Briefly, an input of 7,000 cells was added to each channel of a chip with a recovery rate of 1,500-2,500 cells. The cells were then partitioned into Gel Beads in Emulsion (GEMs) in the Chromium instrument, where cell lysis and barcoded reverse transcription of RNA occurred, followed by amplification, tagmentation and 5' adaptor attachment. Libraries were sequenced on an Illumina NextSeq 500.

Droplet scRNA-Seq Data Processing

Alignment to the mm10 mouse genome and unique molecular identifier (UMI) collapsing was performing using the Cellranger toolkit (version 1.3.1, 10× Genomics). For each cell, the number of genes were quantified for which at least one UMI was mapped, and then excluded all cells with fewer than 1,000 detected genes. Highly variable genes were then identified. Variable gene selection. A logistic regression was fit to the cellular detection fraction (often referred to as a), using the total number of UMIs per cell as a predictor. Outliers from this curve are genes that are expressed in a lower fraction of cells than would be expected given the total number of UMIs mapping to that gene, i.e., cell-type- or state-specific genes. Mouse-to-mouse variation was controlled for by providing mouse labels as a covariate and selecting only genes that were significant in all mice, and used a threshold of deviance $<-0.1$, producing a set of 806 variable genes. Known cell-cycle genes (either part of a cell-cycle signature (Kowalczyk et al., 2015) or in the Gene Ontology term 'Cell-Cycle': GO:0007049) were excluded, resulting in a set of 672 variable genes. Dimensionality reduction. The expression matrix was restricted to the subsets of variable genes and high-quality cells noted above, and then centered and scaled values before inputting them into principal component analysis (PCA), which was implemented using the R package 'Seurat' version 2.3.4. Given that many principal components explain very little of the variance, the signal-to-noise ratio can be improved substantially by selecting a subset of n top principal components, 13 principal components were selected by inspection of the 'knee' in a scree plot. Scores from only these principal components were used as the input to further analysis. Batch correction and clustering. Both prior knowledge and our data show that different cell types have differing proportions in the small intestine. This makes conventional batch correction difficult, as, due to random sampling effects, some batches may have very few of the rarest cells. To avoid this problem, an initial round of unsupervised clustering was performed using k-nearest neighbor (kNN) graph-based clustering, implemented in Seurat using the 'FindClusters' function, using a resolution parameter of 1. Next batch correction was performed within each identified cluster (which contained only transcriptionally similar cells) ameliorating problems with differences in abundance. Batch correction was performed (only on the 672 variable genes) using ComBat (Johnson et al., 2007) as implemented in the R package sva (Leek et al., 2012) using the default parametric adjustment mode. Following this batch correction step, PCA and kNN-based clustering was re-run to identify the final clusters (resolution parameter=0.25). Visualization. For visualization, the dimensionality of the datasets was further reduced using the 'Barnes-hut' approximate version of t-SNE (Haber et al., 2017) as implemented in the Rtsne function from the 'Rtsne' R package using 1,000 iterations and a perplexity setting of 60. Testing for changes in cell-type proportions. To assess the significance of changes in the proportions of cells in different clusters, a negative binomial regression model was used to model the counts of cells in each cluster, while controlling for any mouse-to-mouse variability amongst our biological replicates. For each cluster, the number of cells detected was modeled in each analyzed mouse as a random count variable using a negative binomial distribution. The frequency of detection is then modeled by using the natural log of the total number of cells profiled in a given mouse as an offset. The condition of each mouse (i.e., knock-out or wild-type) is then provided as a covariate. The negative binomial model was fit using the R command 'glm.nb' from the 'MASS' package. The p-value for the significance of the effect produced by the knock-out was then assessed using a likelihood-ratio test, computing using the R function 'anova'. Scoring cells using signature gene sets. To obtain a score for a specific set of n genes in a given cell, a 'background' gene set was defined to control for differences in sequencing coverage and library complexity. The background gene set was selected to be similar to the genes of interest in terms of expression level. Specifically, the 10n nearest neighbors in the 2-D space defined by mean expression and detection frequency across all cells were selected. The signature score for that cell was then defined as the mean expression of the n signature genes in that cell, minus the mean expression of the 10n background genes in that cell. Violin plots to visualize the distribution of these scores were generated using the R package 'ggplot2'. Cells were scored in this manner for Paneth cell markers (Haber et al., 2017), proliferation (Kowalczyk et al., 2015), apoptosis (Dixit et al., 2016), and intestinal stem cell markers (Munoz et al., 2012b). Enrichment analysis. Enrichment analysis was performed using the hypergeometric probability computed in R using 'phyper'. Differential expression and cell-type signatures. To identify maximally specific genes for cell-types, differential expression tests were performed between each pair of clusters for all possible pairwise comparisons. Then, for a given cluster, putative signature genes were filtered using the maximum FDR Q-value and ranked by the minimum $\log_2$ fold-change of means (across the comparisons). This is a stringent criterion because the minimum fold-change and maximum Q-value represent the weakest effect-size across all pairwise comparisons. Cell-type signature genes for the initial droplet based scRNA-seq data were obtained using a maximum FDR of 0.001 and a minimum $\log_2$ fold-change of 0.1. Differential expression tests were carried using a two part 'hurdle' model to control for both technical quality and mouse-to-mouse variation. This was implemented using the R package MAST (Finak et al., 2015), and p-values for differential expression were computed using the likelihood-ratio test. Multiple hypothesis testing correction was performed by controlling the false discovery rate (FDR) using the R function 'p.adjust', and results were visualized using 'volcano' plots constructed using 'ggplot2'. Code availability. R scripts enabling the main steps of the analysis to be reproduced are available from the corresponding authors upon request.

ChIP-Sequencing Analysis

Small intestine crypt isolation. Crypt isolation followed previously published protocols with minor modifications (Guo et al., 2009; Tinkum et al., 2015). Briefly fed or fasted mice were euthanized by CO2, the whole SI was collected, flushed with PBS ($Ca^{2+}$- and $Mg^{2+}$-free, 2 mM EDTA, 100 nM TSA) to remove feces, and the mesentery was removed. The SI sample was cut longitudinally then cut transversely into 4 equal pieces. Each sample was placed on ice in PBS ($Ca^{2+}$- and $Mg^{2+}$-free, 100 nM TSA) while the remaining samples were collected. After collection of all samples, SI were incubated in PBS ($Ca^{2+}$- and $Mg^{2+}$-free, 2 mM EDTA, 100 nM TSA) for 10 min then transferred to HBSS ($Ca^{2+}$- and $Mg^{2+}$-free, 2 mM EDTA, 100 nM TSA). Crypts were released through a series of vortex washes at 1,600 rpm in HBSS ($Ca^{2+}$- and $Mg^{2+}$-free, 2 mM EDTA, 100 nM TSA) at 4° C. Supernatants from all vortex washes were filtered through 70-μm mesh and pooled into 50 ml conical tubes to remove villus material and tissue fragments. Isolated crypts were pelleted at 1000 rpm at 4° C. After this step, whole crypts were utilized for flow cytometry (detailed below), spheroid cell line establishment (de la Cruz Bonilla et al., 2018) and treatment (detailed below), or ChIP-seq (detailed below). For ChIP-seq, crypts were first suspended in ADMEM/F12 (D6421, Millipore Sigma) supplemented with 10 U/mL penicillin, 10 μg/mL streptomycin, 2 mM L-glutamine, 10 mM HEPES, 10 μM TGF-β RI Kinase Inhibitor VI (SB431542, Calbiochem), 10 μM Y-27632 dihydrochloride (Millipore Sigma), 0.5 mM N-acetylcysteine amide (Millipore Sigma), and 100 nM TSA.

Chromatin Immunoprecipitation. Chromatin immunoprecipitations were performed using a previously published protocol with modifications for SI crypts (Garber et al., 2012). Briefly, whole isolated crypts from 4 animals were pooled per treatment per replicate and cross-linked for 10 min at 37° C. with 1% formaldehyde in supplemented media and quenched with 0.125 M glycine for 5 min at 37° C.

Crypts were washed with PBS with 1× protease inhibitor cocktail (Millipore Sigma-Aldrich) and stored at −80° C. Pellets were thawed and then lysed for 30 min on ice with I-ChIP buffer (12 mM Tris-HCl pH 8.0, 6 mM EDTA pH 8.0, 0.1×PBS, 0.5% SDS) plus cOmplete mini protease inhibitors. Sonication conditions were optimized (60 cycles; 30 s on/off) for SI crypt cells using a Bioruptor (Diagnode) to achieve shear length of 250-500 bp. 10% total chromatin was reserved as an input control. Chromatin was diluted 5 fold and immunoprecipitation was performed overnight by incubation of the sonicated cell lysate with 30 μL of protein G magnetic dynabeads (Invitrogen) previously coupled to target antibody for a minimum of 1 h at 4° C. Immune complexes were then washed five times with cold RIPA buffer (10 mM Tris-HCl, pH 8.0, 1 mM EDTA, pH 8.0, 140 mM NaCl, 1% Triton X-100, 0.1% SDS, 0.1% DOC), twice with cold high-salt RIPA buffer (10 mM Tris-HCl, pH 8.0, 1 mM EDTA, pH 8.0, 500 mM NaCl, 1% Triton X-100, 0.1% SDS, 0.1% DOC), and twice with cold LiCl buffer (10 mM Tris-HCl, pH 8.0, 1 mM EDTA, pH 8.0, 250 mM LiCl, 0.5% NP-40, 0.5% DOC). Elution and reverse cross-linking was performed in 50 ul direct elution buffer (10 mM Tris-HCl, pH 8.0, 5 mM EDTA, pH 8.0, 300 mM NaCl and 0.5% SDS) with Proteinase K and RNaseA at 65° C. overnight. Eluted DNA was cleaned up with solid-phase reversible immobilization (SPRI) beads (Beckman-Coulter). Antibody details are listed in the key resources table.

ChIP-sequencing library preparation. Library preparation was performed as described in (Garber et al., 2012). Briefly, enzymes from New England Biolabs were used for the following library construction processes: DNA end-repair, A-base addition, adaptor ligation, U Excision, and PCR enrichment. ChIP libraries were barcoded using TruSeq DNA LT Adapters, multiplexed together, and sequencing was performed on HiSeq 2000 (Illumina) or NextSeq 500 (Illumina).

ChIP-seq data processing. Raw fastq reads for all ChIP-seq experiments were processed using a snakemake based pipeline (Blecher-Gonen et al., 2013). Briefly, raw reads were first processed using FastQC (http://www.bioinformatics.babraham.ac.uk/projects/fastqc/) and uniquely mapped reads were aligned to the mm9 reference genome using Bowtie version 1.1.2 (Langmead et al., 2009). Duplicate reads were removed using SAMBLASTER (Faust and Hall, 2014) before compression to bam files. To directly compare fed and fasted ChIP-seq samples uniquely mapped reads for each mark were downsampled per condition to 20 million, sorted and indexed using samtools version 1.5 (Li et al., 2009). To visualize ChIP-seq libraries on the IGV genome browser, deepTools version 2.4.0 (Ramirez et al., 2016) was used to generate bigWig files by scaling the bam files to reads per kilobase per million (RPKM). Super ChIP-seq tracks were generated by merging, sorting and indexing replicate bam files using samtools and scaled to RPKM using deepTools.

Identification of ChIP-seq binding sites. Model-based analysis of ChIP-seq (MACS) version 1.4.2 (Zhang et al., 2008) peak calling algorithm was used with a p-value threshold of 1e-5 to identify H3K27ac enrichment over "input" background. Consensus replicate sites and unique fed and fasted sites for H3K27ac were identified using the concatenate, cluster and subtract tools from the Galaxy/Cistrome web based platform (Liu et al., 2011). Briefly, a consensus peak set was first generated by clustering intervals of replicate peaks that directly overlapped by a minimum of 1 bp. Next, a shared peak set was generated by clustering intervals of fed consensus peaks that directly overlapped fasted consensus peaks by a minimum of 1 bp. Unique peaks were then identified by subtracting the total number of peaks in each condition by the shared peak set.

Assigning binding sites to genes. A list of Ensembl genes was obtained from the UCSC Table browser (genome.ucsc.edu/). Proximal promoters were defined as ±5 kb from the transcription start site (TSS) and the gene body was defined as all genic regions outside of the +5 kb promoter region. Intergenic regions were defined as all regions outside of both the proximal promoter and gene body. H3K27ac peaks were assigned to genes if they overlapped the promoter by a minimum of 1 bp. H3K27ac enhancers were identified defined as all sites outside of the proximal promoter.

Preparation of Nanoparticle PLGA Encapsulated βOHB

Poly(lactic-co-glycolic acid) (PLGA) nanoparticles loaded with β-hydroxybutyrate (βOHB) were generated via a double emulsion technique. Briefly, 0.5 g of PLGA (LG 50:50 Mn 5,000-10,000 Da acid endcap) was dissolved in 2.5 mL of dichloromethane, and a βOHB solution (500 mg/mL) 1 mL was added to the solution and sonicated for 30 sec (Hanchen Instrument 300 w 3 mm probe). The emulsion was then transferred to 50 mL of cold soy lecithin (Alfa Aesar) (10 mg/mL in PBS) and was sonicated for 30 s twice, with a 30 sec wait interval. The dichloromethane was then removed from the solution via stirring for 12 hrs at 4° C. The particles were isolated and washed via centrifugation (5,000 g for 30 m×3 times) and frozen for long term storage.

Preparation of Cyclic βOHB Oligomers

General

Reagents were purchased from commercial sources and used as received. Anhydrous solvents were saturated with argon and purified by passage through two columns of activated alumina. Air-sensitive reactions and compounds were handled with standard Schlenk techniques. Column chromatography was performed on silica gel (230-400 mesh, 60 Å). NMR spectra were acquired on a 400 MHz Bruker AVANCE-400 spectrometer. $^{1}$H NMR and $^{13}$C NMR chemical shifts are reported in ppm relative to that of SiMe$_4$ (δ=0.00) and were referenced internally to residual solvent peaks.

(R)-3-Hydroxybutanoic acid

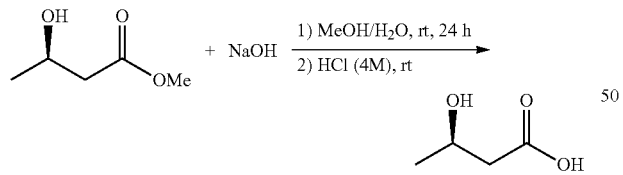

Figure 15:
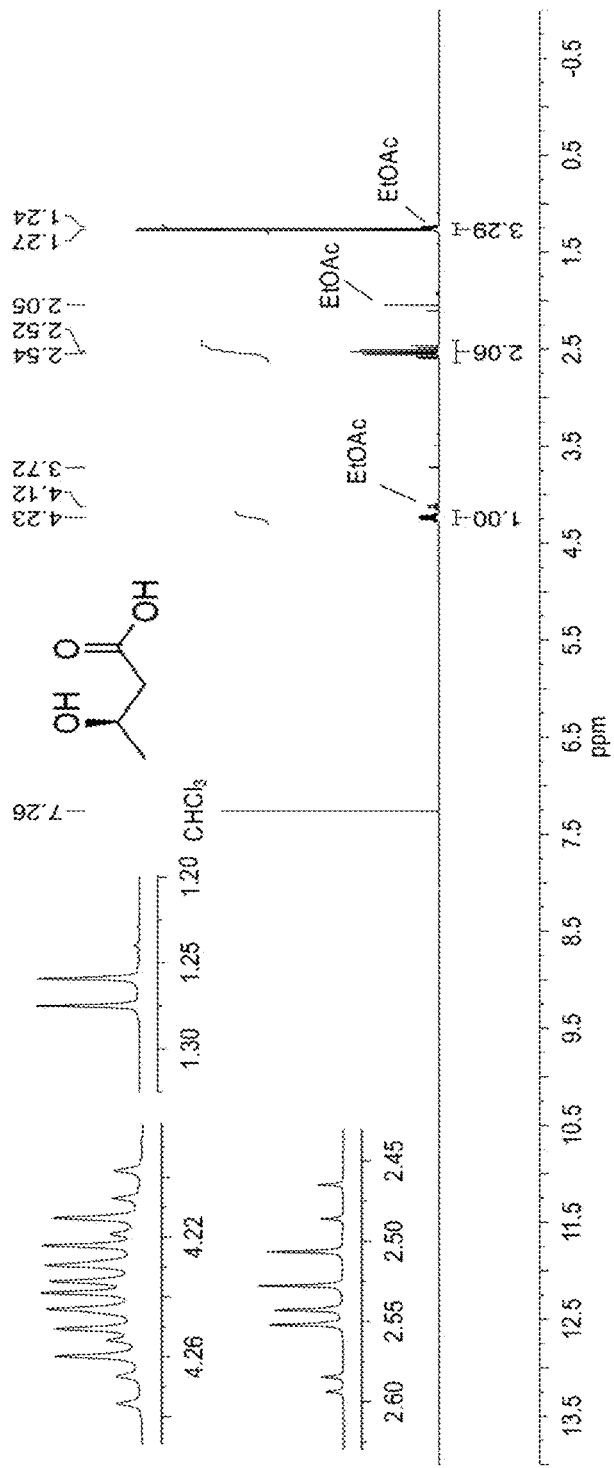
FIG. 15 shows $^1$H NMR spectrum of (R)-3-hydroxybutanoic acid.

To a solution of methyl (R)-3-hydroxybutyrate (9.45 g, 80 mmol) in MeOH (10 mL) was slowly added NaOH (3.52 g, 88 mmol) in water (20 mL). The reaction was exothermic. The reaction was stirred at rt for 24 h. The reaction mixture was acidified using 4 M HCl to pH=1 (pH paper). The acidified mixture was concentrated under vacuum to about 30 mL. NaCl was then added to this solution until saturation. The mixture was extracted with EtOAc (40 mL×5). The combined organic phase was dried over MgSO$_4$. The solvent was removed under vacuum to give a colorless liquid (6.86 g, 82% yield). The material is stored at −80° C. and was used in the next step without further purification. $^{1}$H NMR (400 MHz, CDCl$_3$) δ 4.23 (ddq, J=8.5, 6.3, 3.7 Hz, 1H), 2.57 (dd, J=16.7, 3.7 Hz, 1H), 2.50 (dd, J=16.7, 8.5 Hz, 1H), 1.27 (d, J=6.3 Hz, 3H). FIG. 15). The $^{1}$H NMR chemical shifts are consistent with the values reported in the literature (Juarez-Hernandez, et al., 2012).

Pentolide, Hexolide, and Heptolide of (R)-3-hydroxybutyric Acid

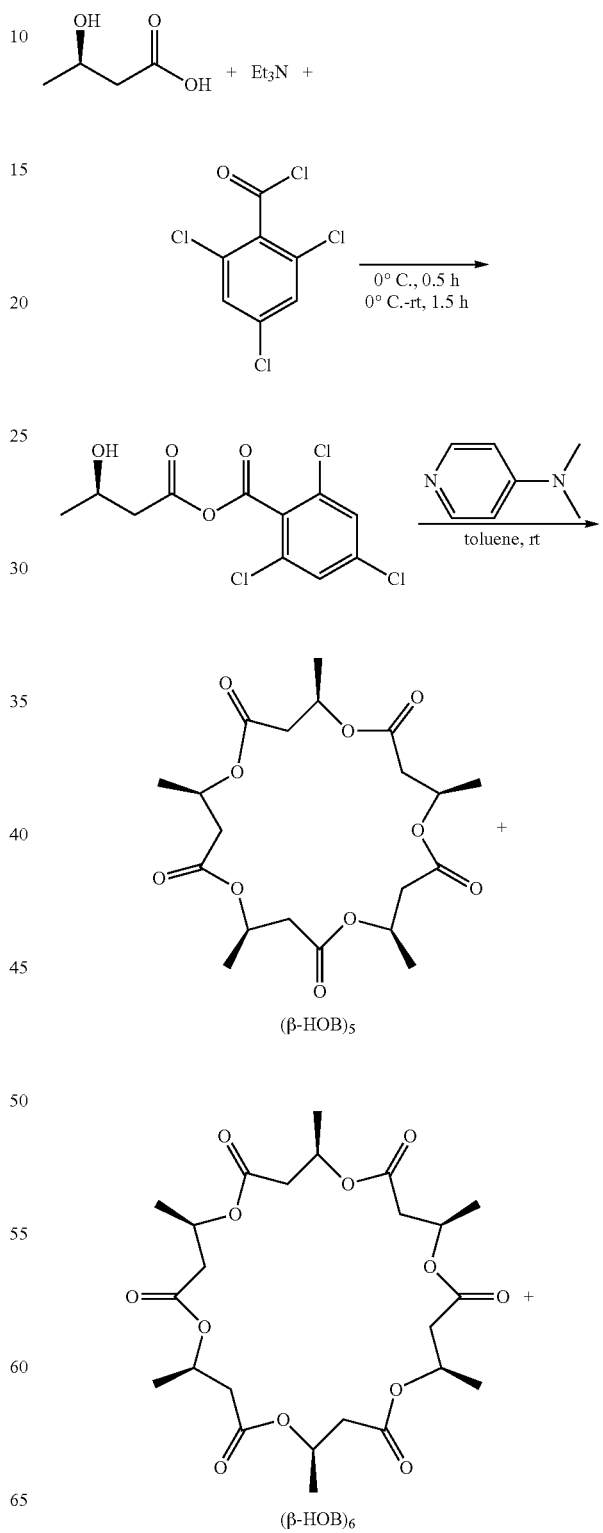

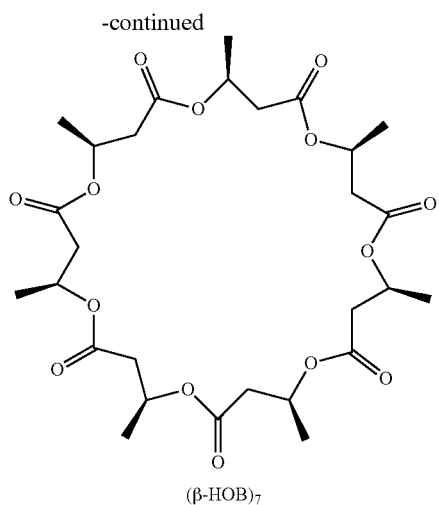

(β-HOB)₇

Figure 16:
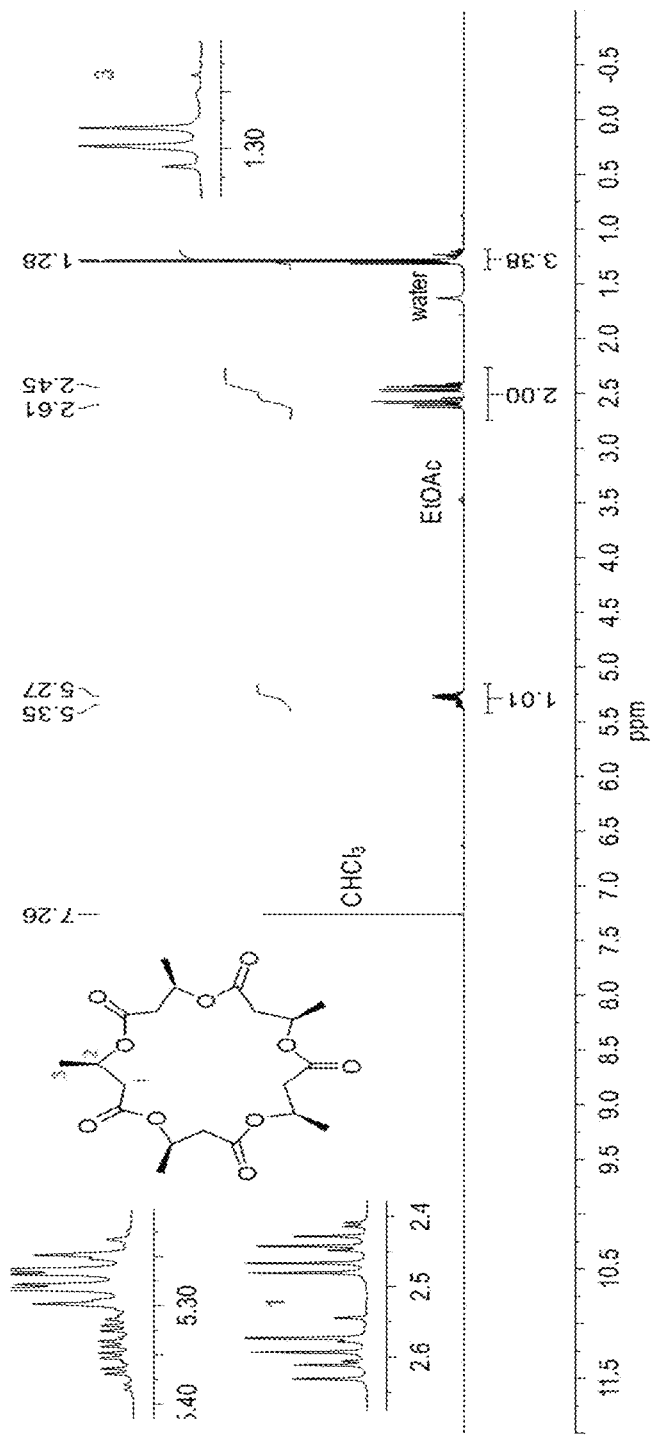
FIG. 16 shows $^1$H NMR spectrum of the pentolide of (R)-3-hydroxybutanoic acid.
Figure 17:
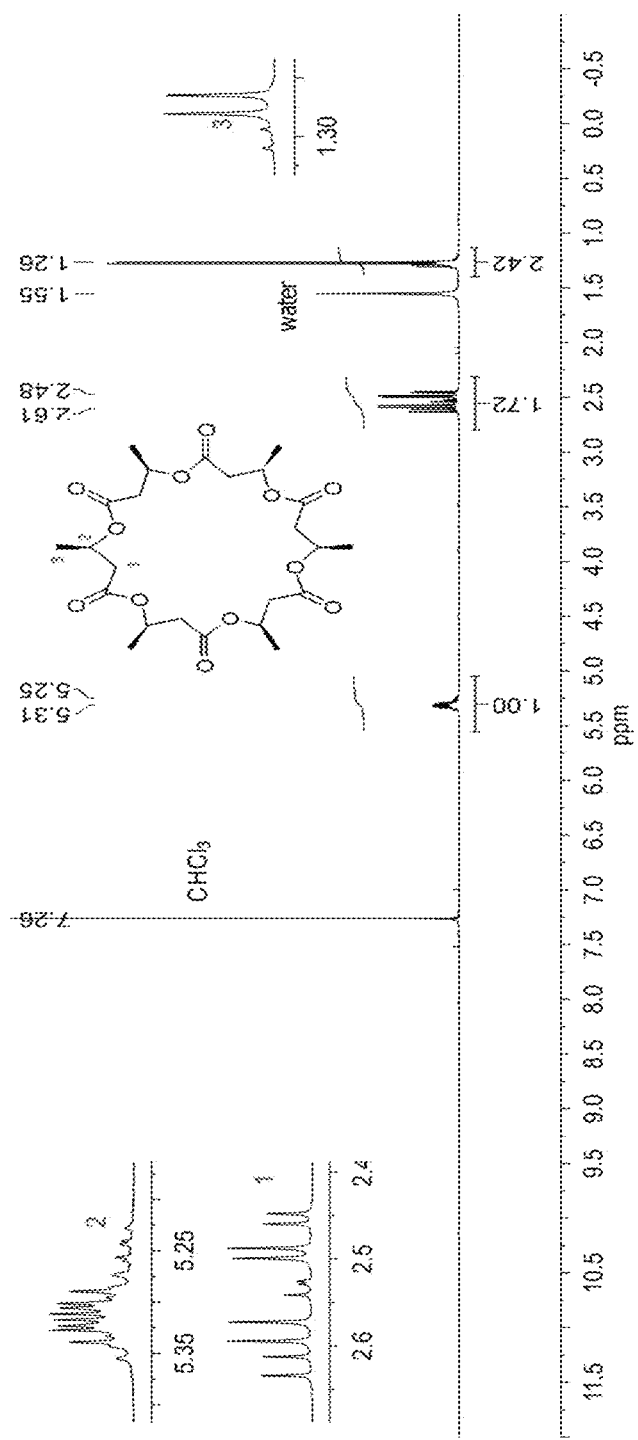
FIG. 17 shows $^1$H NMR spectrum of the hexolide of (R)-3-hydroxybutanoic acid.
Figure 18:
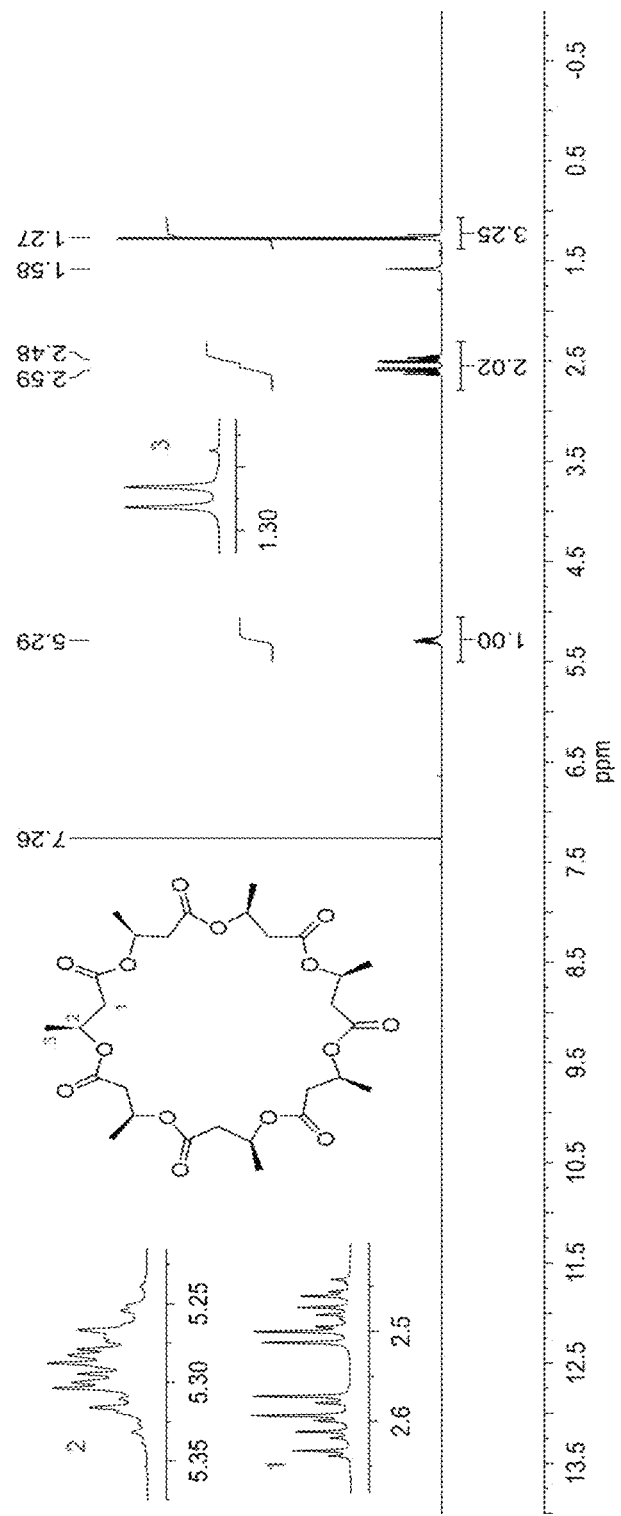
FIG. 18 shows $^1$H NMR spectrum of the heptolide of (R)-3-hydroxybutanoic acid.
Figure 19:
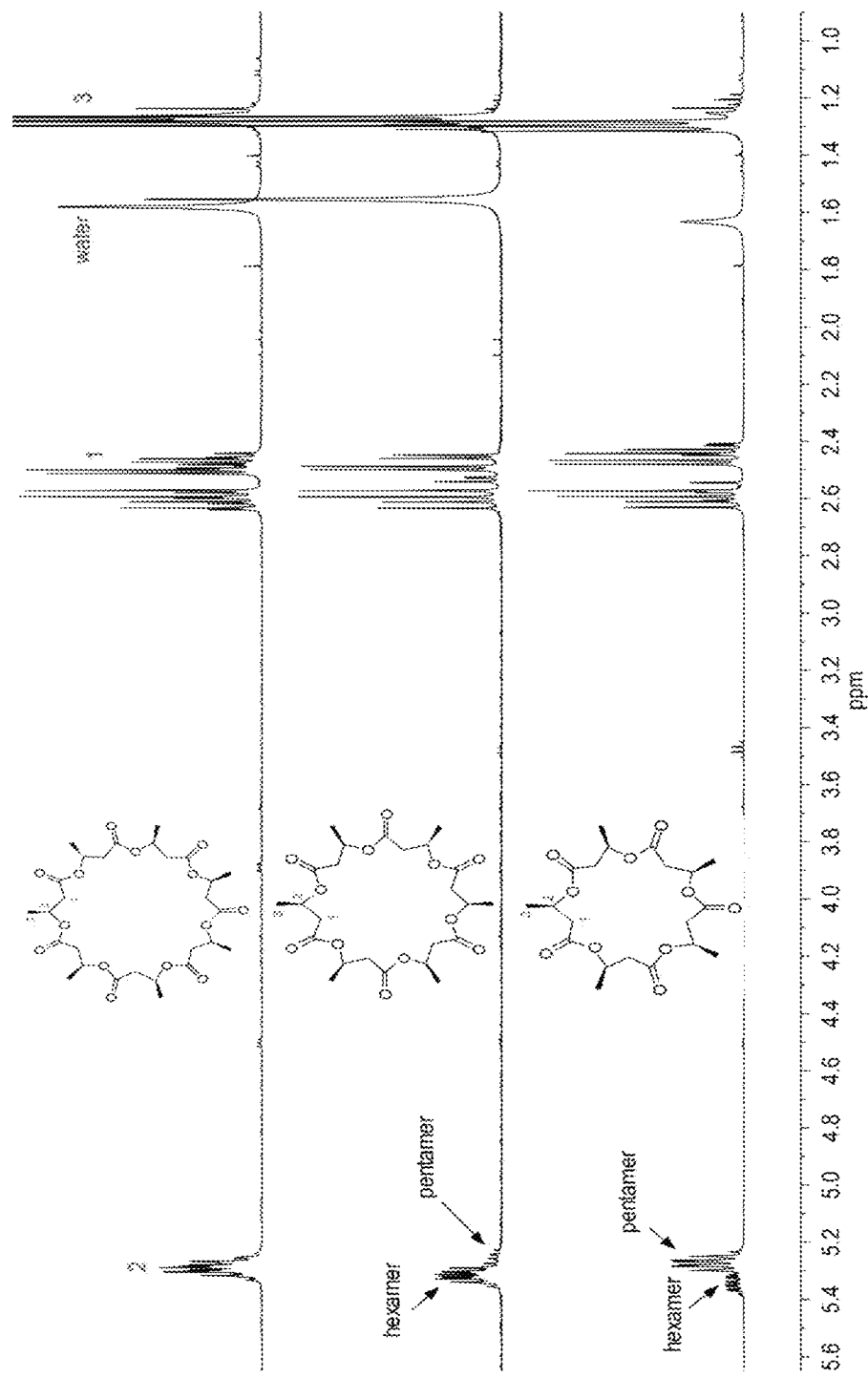
FIG. 19 shows comparison of the $^1$H NMR spectrum of the pentolide, hexolide, and heptolide of (R)-3-hydroxybutanoic acid.

The pentolide, hexolide, and heptolide of (R)-3-hydroxybutyric acid were synthesized according to a procedure reported by Seebach and co-workers (Seebach et al., 1988). To a solution of (R)-3-hydroxybutanoic acid (1.00 g, 9.6 mmol) in anhydrous THF (1.6 mL) was added Et₃N (1.26 g, 1.73 mL, 12.4 mmol) and then 2,4,6-trichlorobenzoyl chloride (2.34 g, 1.50 mL, 9.6 mmol) at 0° C., during which a large amount of precipitate formed. The reaction was stirred at 0° C. for 30 min and gradually warmed to rt over a period of 1.5 h. The thick white slurry was diluted with toluene (10 mL) and suction-filtered. The solid was then washed with another portion of toluene (10 mL). The filtrate (20 mL) was then added by a syringe pump to a solution of DMAP (122 mg, 1.0 mmol) in anhydrous toluene (400 mL) over 4 h. The reaction mixture was diluted with Et₂O (200 mL) and washed with HCl (1 M, 100 mL×2). The organic phase was then washed with sat. NaHCO₃ aq. (100 mL) and brine (100 mL). The organic phase was dried over MgSO₄. The solvents were removed under vacuum to give a slightly yellow mixture of oil and white crystalline solid. The crude product was purified by column chromatography (silica gel, Et₂O: hexanes=7:3). The product was visualized on TLC using KMnO₄ stain. Three fractions were collected as pentolide ($R_f$=0.42, 71 mg, 8.6%), hexolide ($R_f$=0.31, 58 mg, 7.0%), and heptolide ($R_f$=0.23, 40 mg, 4.8%). According to $^1$H NMR spectroscopic studies, the pentolide contained 20 wt % of the hexolide, and the hexolide contained about 7 wt % of the pentolide. The heptolide contained about 24 wt % an unidentified oligolide. $^1$H NMR of pentolide (400 MHz, CDCl₃) δ 5.31-5.23 (m, 1H), 2.60 (dd, J=15.2, 7.9 Hz, 1H), 2.45 (dd, J=15.2, 5.6 Hz, 1H), 1.29 (d, J=6.4 Hz, 3H). (FIG. 16). $^1$H NMR of hexolide (400 MHz, CDCl₃) δ 5.36-5.27 (m, 1H), 2.60 (dd, J=15.9, 8.7 Hz, 1H), 2.47 (dd, J=15.9, 4.7 Hz, 1H), 1.27 (d, J=6.3 Hz, 3H). (FIG. 17). $^1$H NMR of heptolide (400 MHz, CDCl₃) δ 5.35-5.23 (m, 1H), 2.60 (dd, J=15.7, 8.5 Hz, 1H), 2.49 (dd, J=15.7, 4.9 Hz, 1H), 1.27 (d, J=6.3 Hz, 3H). (FIG. 18). The $^1$H NMR chemical shifts are consistent with the reported values (Seebach et al., 1988). (FIG. 19).

Preparation of glycerol-tri((R)-3-hydroxybutyrate)

Synthesis of Glycerol tri((R)-3-hydroxybutyrate)

Figure 21:
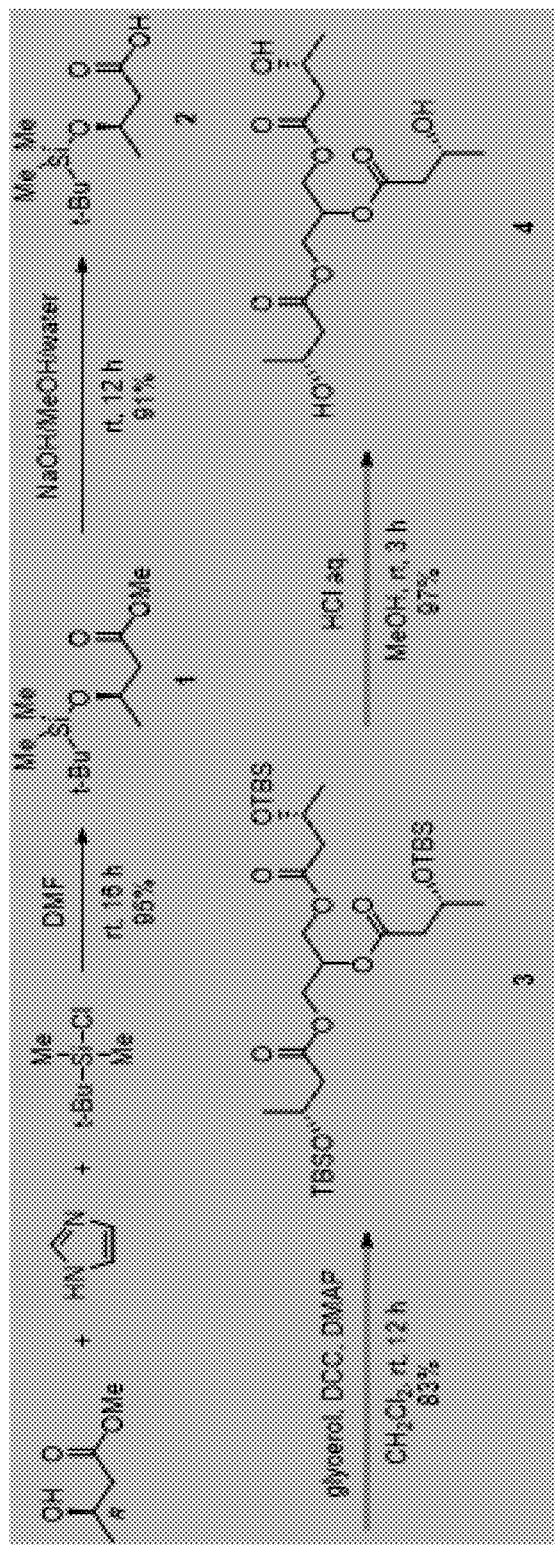
FIG. 21 shows the synthetic route of glycerol tri((R)-3-hydroxybutyrate).
Figure 22:
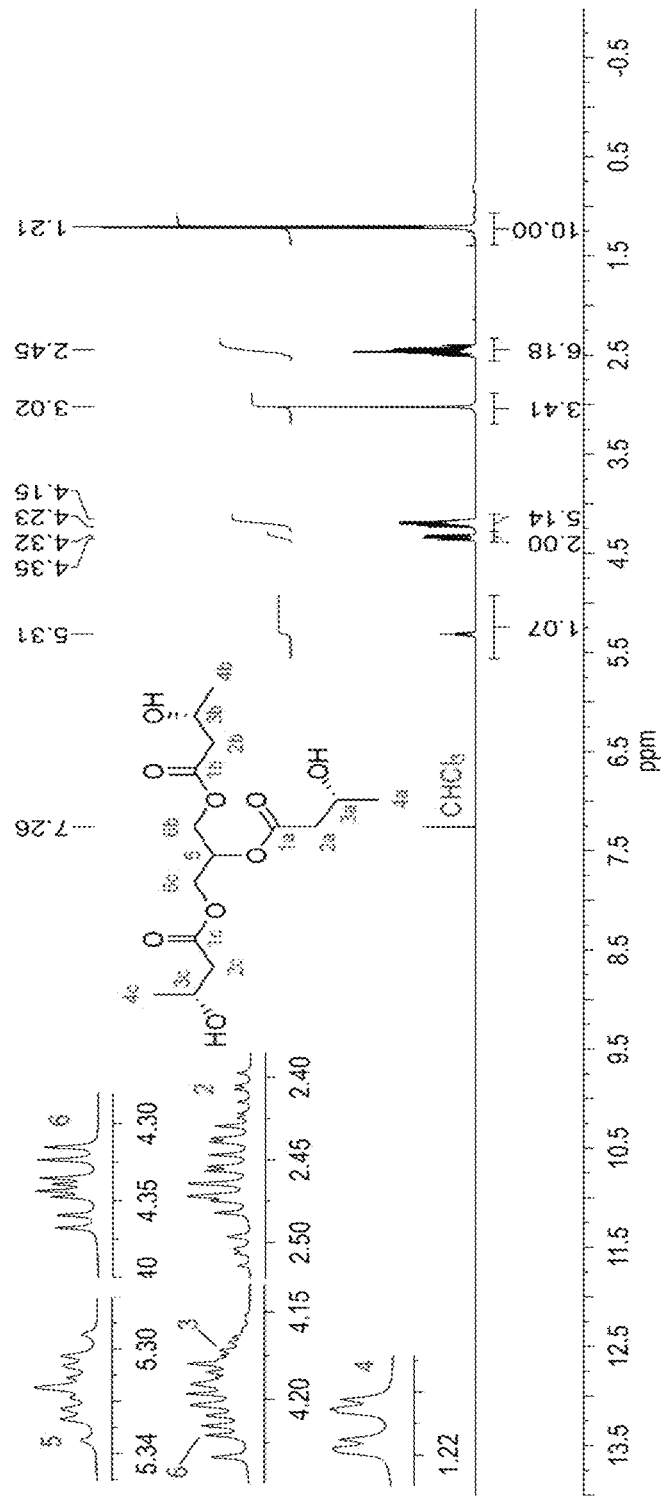
FIG. 22 shows the $^1$H NMR spectrum of glycerol tri((R)-3-hydroxybutyrate).
Figure 23:
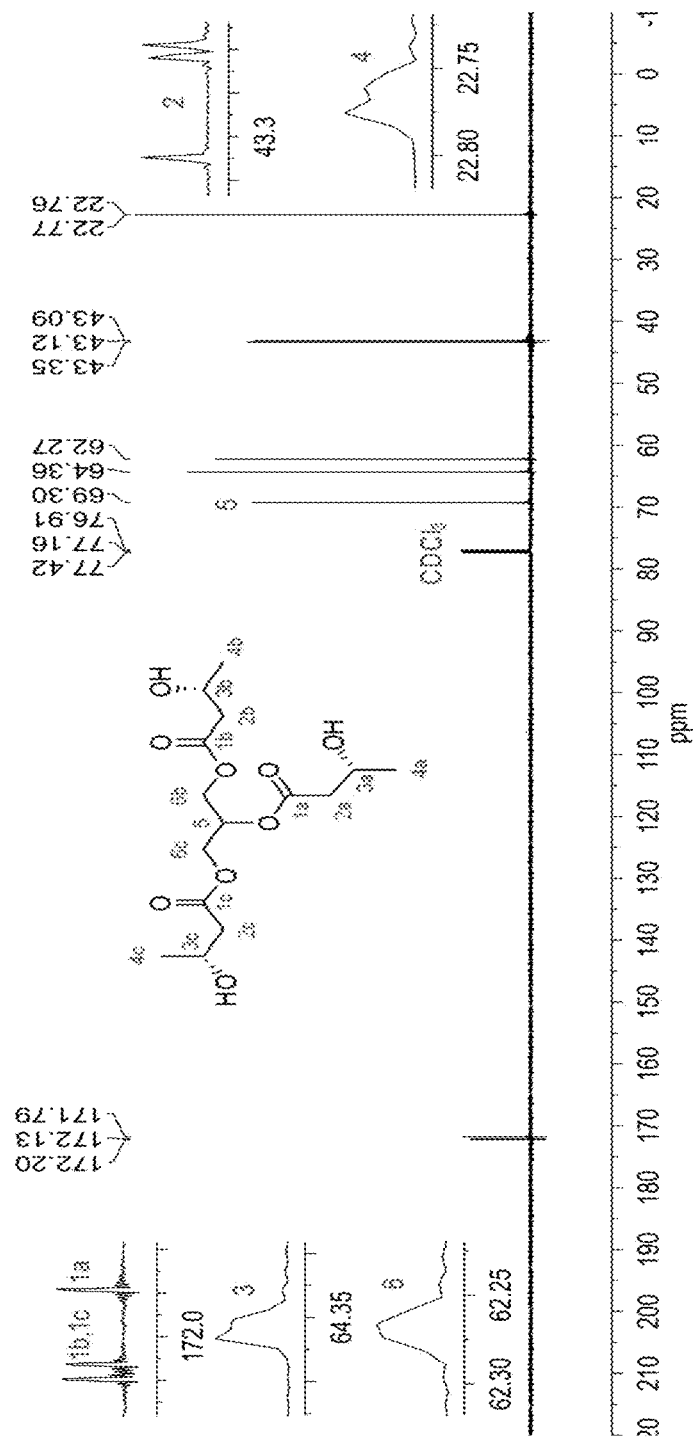
FIG. 23 shows the $^{13}$C NMR spectrum of glycerol tri((R)-3-hydroxybutyrate).

See FIG. 21 for the synthetic scheme used to prepare glycerol tri((R)-3-hydroxybutyrate).

General

Reagents were purchased from commercial sources and used as received. Anhydrous solvents were saturated with argon and purified by passage through two columns of activated alumina. Air-sensitive reactions and compounds were handled with standard Schlenk techniques. Column chromatography was performed on silica gel (230-400 mesh, 60 Å). NMR spectra were acquired on a 400 MHz Bruker AVANCE-400 spectrometer. $^1$H NMR and $^{13}$C NMR chemical shifts are reported in ppm relative to that of SiMe₄ (δ=0.00) and were referenced internally to residual solvent peaks.

Step One: Preparation of methyl (R)-3-((tert-butyldimethylsilyl)oxy)butanoate

To a solution of methyl (R)-3-hydroxybutyrate (11.8 g, 100 mmol) and tert-butyldimethylsilyl chloride (18.1 g, 150 mmol) in anhydrous DMF was added imidazole (10.2 g, 150 mmol) in small portions. The reaction was slightly exothermic. The reaction was stirred overnight. The reaction mixture was quenched with saturated aqueous NaHCO₃ (100 mL) and ether (100 mL). The mixture was stirred for 30 min and further diluted with water (500 mL). The mixture was then extracted with Et₂O (100 mL×3). The combined organic layer was washed with brine (200 mL) and dried over MgSO₄. The solvent was removed under vacuum. The crude product was purified by column chromatography (hexanes/ethyl acetate=10:0 to 10:1, visualized using KMnO₄ stain). $R_f$=0.45 (hexanes/ethyl acetate=10:1). A colorless liquid was obtained (22.1 g, 95% yield). EI-MS(+) m/z calcd for [M-Me]⁺ 217, found 217; calcd for [M-t-Bu]⁺ 175, found 175.

Step Two: Preparation of (R)-3-((tert-butyldimethylsilyl)oxy)butanoic Acid

To a solution of (R)-3-((tert-butyldimethylsilyl)oxy)butanoate (22.1 g, 95 mmol) in MeOH (450 mL) was added an aqueous solution of NaOH (1 M, 450 mL). The reaction was stirred at room temperature overnight. The reaction mixture was concentrated to approximately 300 mL. The solution was washed with Et₂O (100 mL×2). The aqueous layer was acidified to pH 4 by adding HCl (0.5 M, ~1000 mL) dropwise, which resulted in a milky mixture. The mixture was extracted with Et₂O (75 mL×4). The combined organic layer was dried over MgSO₄. The solvent was removed under vacuum to give a colorless liquid (18.8 g, 91% yield). The product was used in the next step without further purification. $^1$H NMR (500 MHz, CDCl₃) δ 4.28 (sextet, J=6.0 Hz, 1H), 2.50 (pseudo d, J=6.0 Hz, 2H), 1.24 (d, J=6.2 Hz, 3H), 0.88 (s, 9H), 0.10 (s, 3H), 0.08 (s, 3H). EI-MS(+) m/z calcd for [M-t-Bu]⁺ 161, found 161.

Step Three: Preparation of propane-1,2,3-triyl (3R, 3'R,3"R)-tris(3-((tert-butyldimethylsilyl)oxy)butanoate)

To a solution of (R)-3-((tert-butyldimethylsilyl)oxy)butanoic acid (18.8 g, 86 mmol) in CH₂Cl₂ (344 mL) was added DCC (26.6 g, 129 mmol). Glycerol (2.11 g, 22.9 mmol) and DMAP (1.58 g, 12.9 mmol) were then added. A large amount of white precipitate formed. The reaction was stirred at room temperature overnight. The reaction mixture was filtered. The solid was washed with CH₂Cl₂ (100 mL). The solvent was removed under vacuum. The crude product was purified by column chromatography (hexanes/ethyl acetate=100:5 to 100:10). $R_f$=0.30 (hexanes/ethyl acetate=100:10, visualized using $KMnO_4$ stain). A colorless viscous liquid was obtained (13.2 g, 83%). $^1$H NMR (500 MHz, $CDCl_3$) δ 5.26-5.21 (m, 1H), 4.30-4.21 (m, 5H), 4.16 (dd, J=5.7, 2.8 Hz, 1H), 4.14 (dd, J=5.7, 2.8 Hz, 1H), 2.55-2.45 (m, 3H), 2.42-2.35 (m, 3H), 1.21-1.18 (m, 9H), 0.86 (s, 9H), 0.86 (s, 18H), 0.07 (s, 3H), 0.06 (s, 6H), 0.05 (s, 3H), 0.03 (s, 6H). $^{13}$C NMR (126 MHz, $CDCl_3$) δ 171.20, 171.13, 170.70, 69.05, 65.81, 65.80, 65.61, 62.28, 44.67, 44.65, 25.91, 25.87, 24.01, 23.99, 23.89, 18.12, 18.09, 18.08, −4.38, −4.40, −4.77, −4.86. ESI-MS(+) m/z calcd for [M+Na]$^+$ 715.4, found 715.3. DART-Q-TOF HRMS(−) m/z calculated for $C_{33}H_{68}ClO_9Si_3^-$ [M+Cl]$^-$ 727.3865, found 727.3875.

Step Four: Preparation of glycerol-tri((R)-3-hydroxybutyrate)

To a solution of HCl (2 wt %, 13.0 mL) in MeOH (250 mL) was added propane-1,2,3-triyl (3R,3'R,3''R)-tris(3-((tert-butyldimethylsilyl)oxy)butanoate) (3.62 g, 5.22 mmol). The reaction was stirred at rt for 3 h and quenched with $NaHCO_3$ aq. (600 mg, 7.1 mmol, in 20 mL of water). The solvents were removed under vacuum. The crude product was purified by column chromatography (EtOAc: MeOH=100:0 to 100:5, $R_f$=0.50 with EtOAc:MeOH=100:5, visualized using $KMnO_4$ stain). A slight yellow viscous liquid was obtained (1.78 g, 97%). $^1$H NMR (500 MHz, $CDCl_3$) δ 5.34 (tt, J=6.1, 4.1 Hz, 1H), 4.38 (dd, J=10.1, 4.1 Hz, 1H), 4.35 (dd, J=10.0, 4.1 Hz, 1H), 4.26-4.17 (m, 5H), 3.05 (br, 3H), 2.55-2.41 (m, 6H), 1.25-1.22 (m, 9H). $^{13}$C NMR (126 MHz, $CDCl_3$) δ 172.20, 172.13, 171.79, 69.30, 64.36 (m), 62.27, 43.35, 43.12, 43.09, 22.77, 22.76. ESI-MS(−) m/z calcd for [M+$HCO_2$]$^-$ 395.2, found 394.9. DART-Q-TOF HRMS(+) m/z calculated for $C_{15}H_{27}O_9^+$ [M+H]$^+$ 351.1650, found 351.1635; and $C_{15}H_{30}NO_9^+$ [M+$NH_4$]$^+$ 368.1915, found 368.1913.

Quantification and Statistical Analysis

Unless otherwise specified in the figure legends or Method Details, all experiments reported in this study were repeated at least three independent times. For murine organoid assays 2-4 wells per group with at least 3 different mice were analyzed. All sample number (n) of biological replicates and technical replicates, definition of center, and dispersion and precision measures can be found in the figure legends. The center values shown in box and whisker plots refer to the median while that in other graphs indicate mean. For analysis of the statistical significance of differences between groups, GraphPad Prism was used to perform nonparametric Mann-Whitney U (Wilcoxon rank-sum) test that allows two groups or conditions or treatments to be compared without making the assumption that values are normally distributed. No samples or animals were excluded from analysis. Unless otherwise specified in the figure legends, n>3 young adult (3 to 5 months old) male and female mice were used for in vivo experiments. Age- and sex-matched mice were assigned to groups without randomization and sample size estimation. Studies were not conducted blind with the exception of all histological analyses.

Data and Code Availability

Datasets generated in this study are available at GEO repository: including population RNA sequencing data (GSE89568 and GSE67324), single-cell RNA-seq data (GSE112205) and CHIP-seq data (GSE134044). All relevant data supporting the findings of this study are also available upon request.

Example 1

Ketogenic Enzyme HMGCS2 is Enriched in Lgr5+ Intestinal Stem Cells (ISCs)

Figures 1A, 1B:
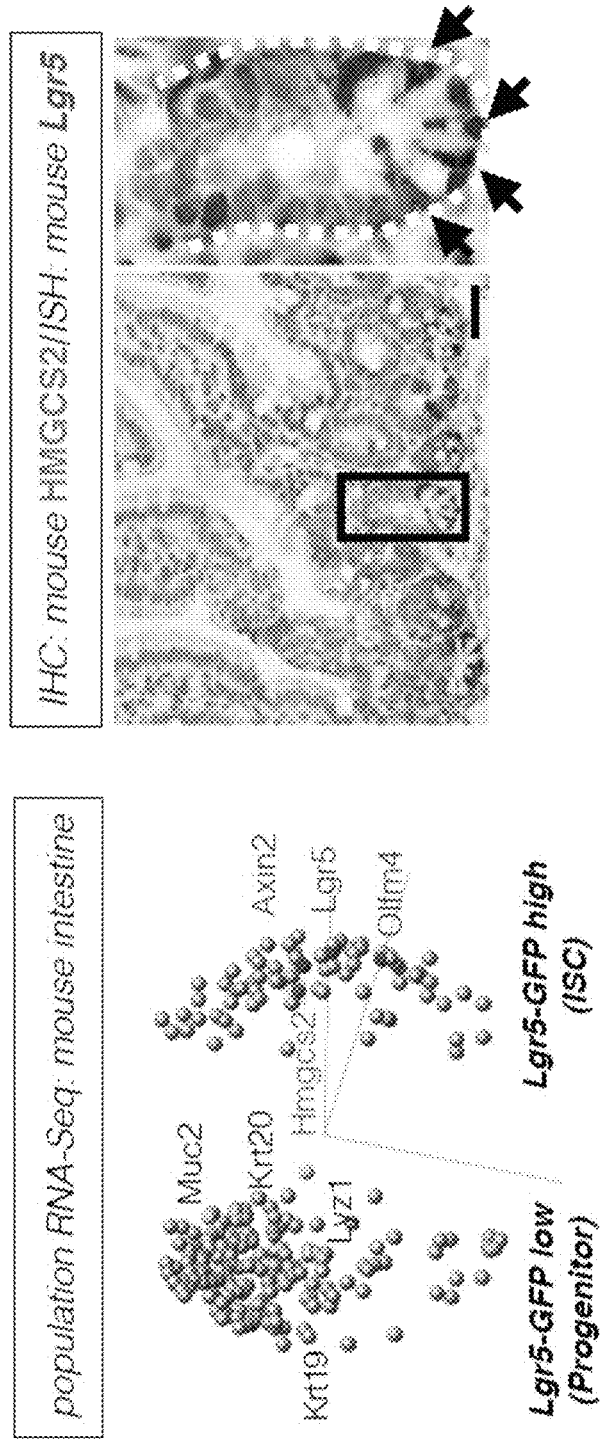
FIGS. 1A-1F show HMGCS2 enriches for Lgr5+ intestinal stem cells (ISCs).
Figure 1D:
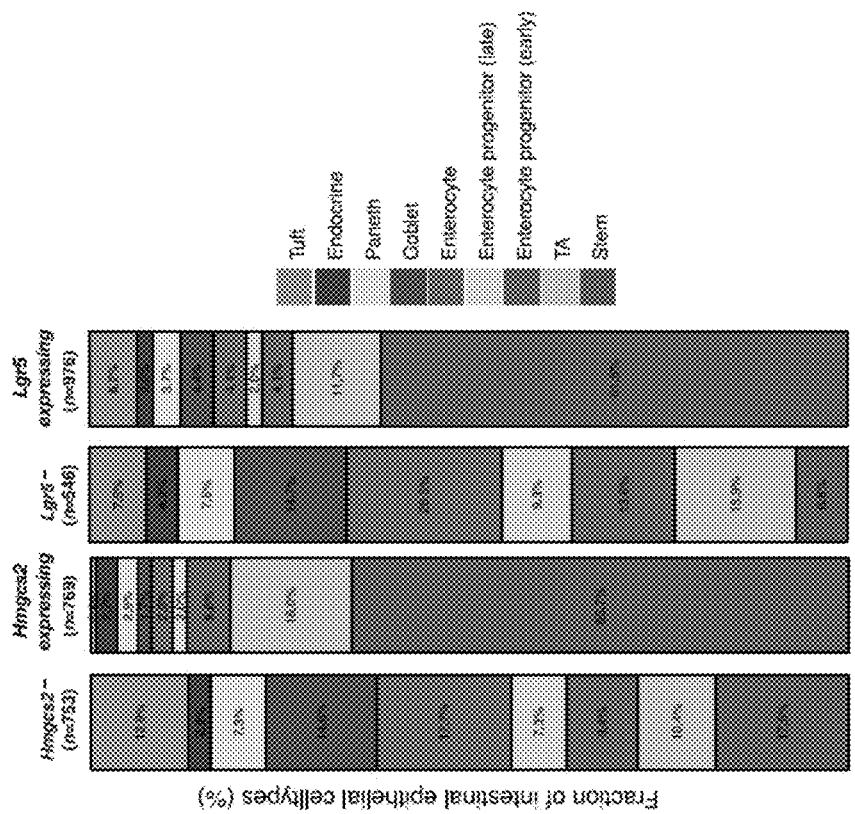
Figure 8A:
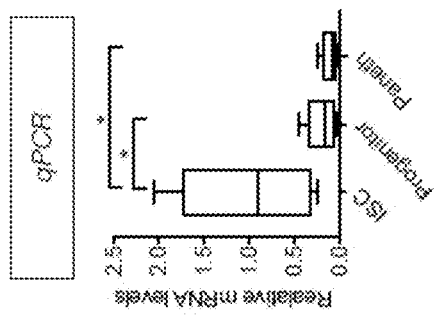

To identify the metabolic pathways enriched in ISCs, RNA-Seq data was analyzed (Beyaz et al., 2016; Mihaylova et al., 2018) from populations of flow sorted Lgr5-GFP$^{hi}$ ISCs (Sato et al., 2009), Lgr5-GFP$^{low}$ progenitors (Sato et al., 2009) and CD24+c-Kit+ Paneth cells (Beyaz et al., 2016; Sato et al., 2011) from Lgr5-eGFP-IRES-CreERT2 knock-in mice (Barker et al., 2007) (Data Availability). Because Paneth cells are metabolically distinct from ISCs and progenitors (Rodriguez-Colman et al., 2017), the focus was on genes differentially expressed between ISCs and progenitors (filtered by two group comparison ρ/ρmax=5e-4; p<0.14, q<0.28). 3-Hydroxy-3-Methylglutaryl-CoA Synthase 2 (Hmgcs2), the gene encoding the rate-limiting step for ketogenesis (schematic, FIG. 8A), was a metabolic enzyme with significant differential expression (p=0.002; q=0.046) between Lgr5$^+$ ISCs (GFP$^{hi}$ cells) and progenitors (GFP$^{low}$ cells) (FIG. 2A; see also Table S1 of Cheng, C.-W., Ketone Body Signaling Mediates Intestinal Stem Cell Homeostasis and Adaptation to Diet, Cell 178, 1115-1131, Aug. 22, 2019, the contents of which are incorporated herein by reference in their entirety), which was also in agreement with the published Lgr5 ISC signature (Munoz et al., 2012a). Lastly, re-analysis of single-cell transcriptome data from the small intestine (Haber et al., 2017) demonstrated that 65.7% of Hmgcs2-expressing cells were stem cells and 16% were transit-amplifying progenitors, which is similar to the distribution observed for Lgr5-expressing cells (FIG. 1D).

Figure 1C:
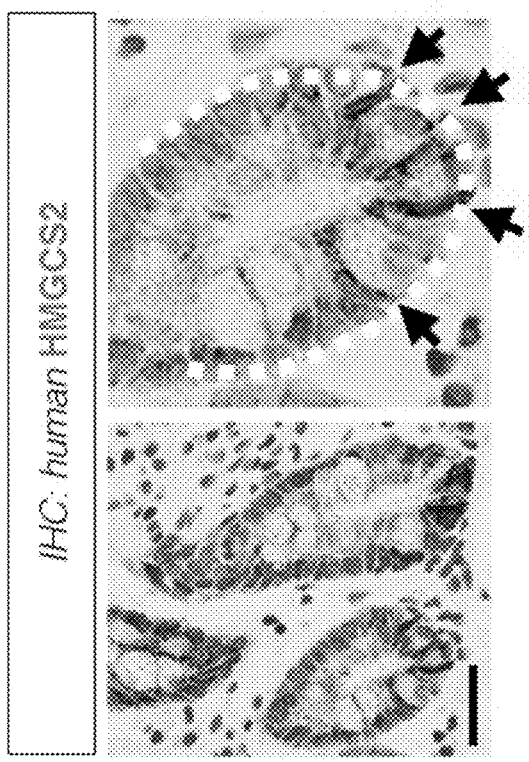
Figure 8B:
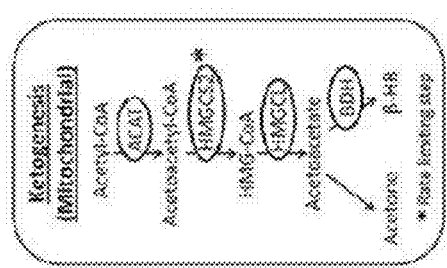
Figure 8C:
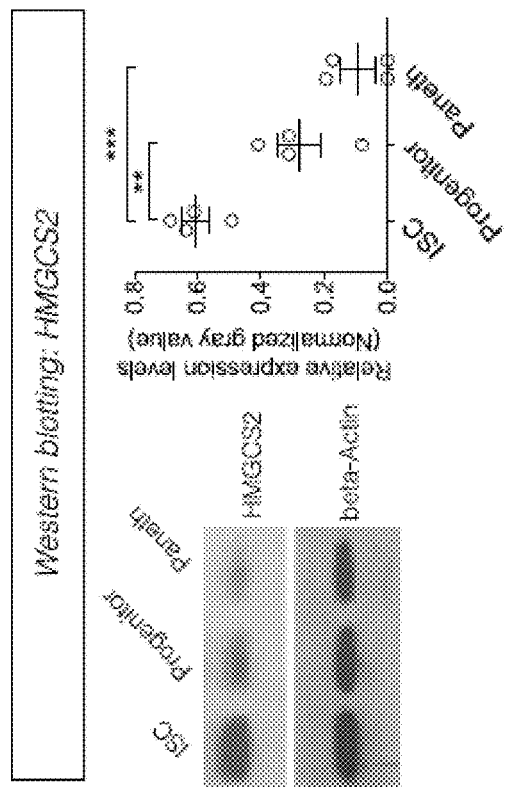
Figure 8D:
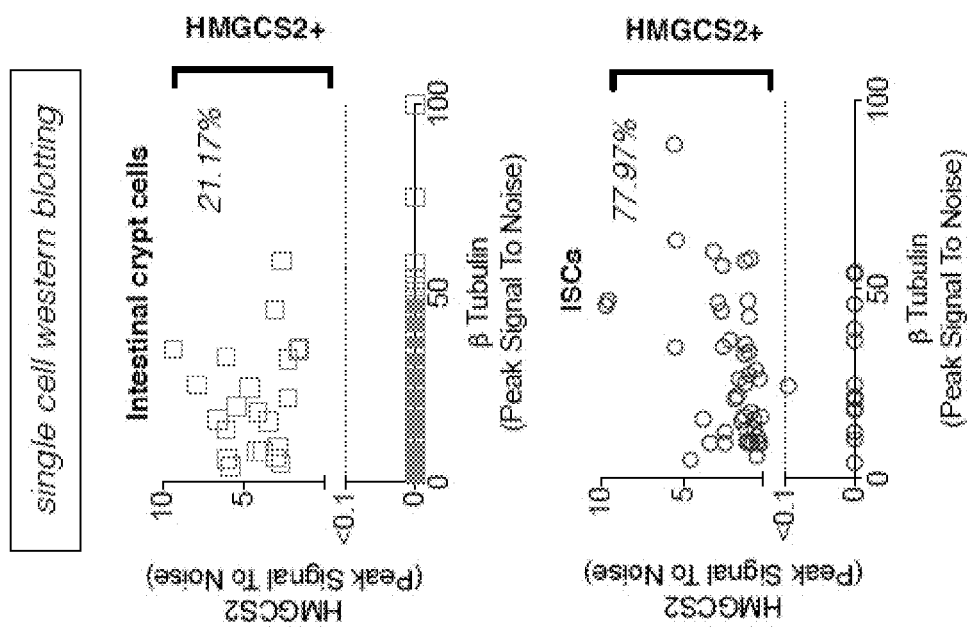
Figure 8E:
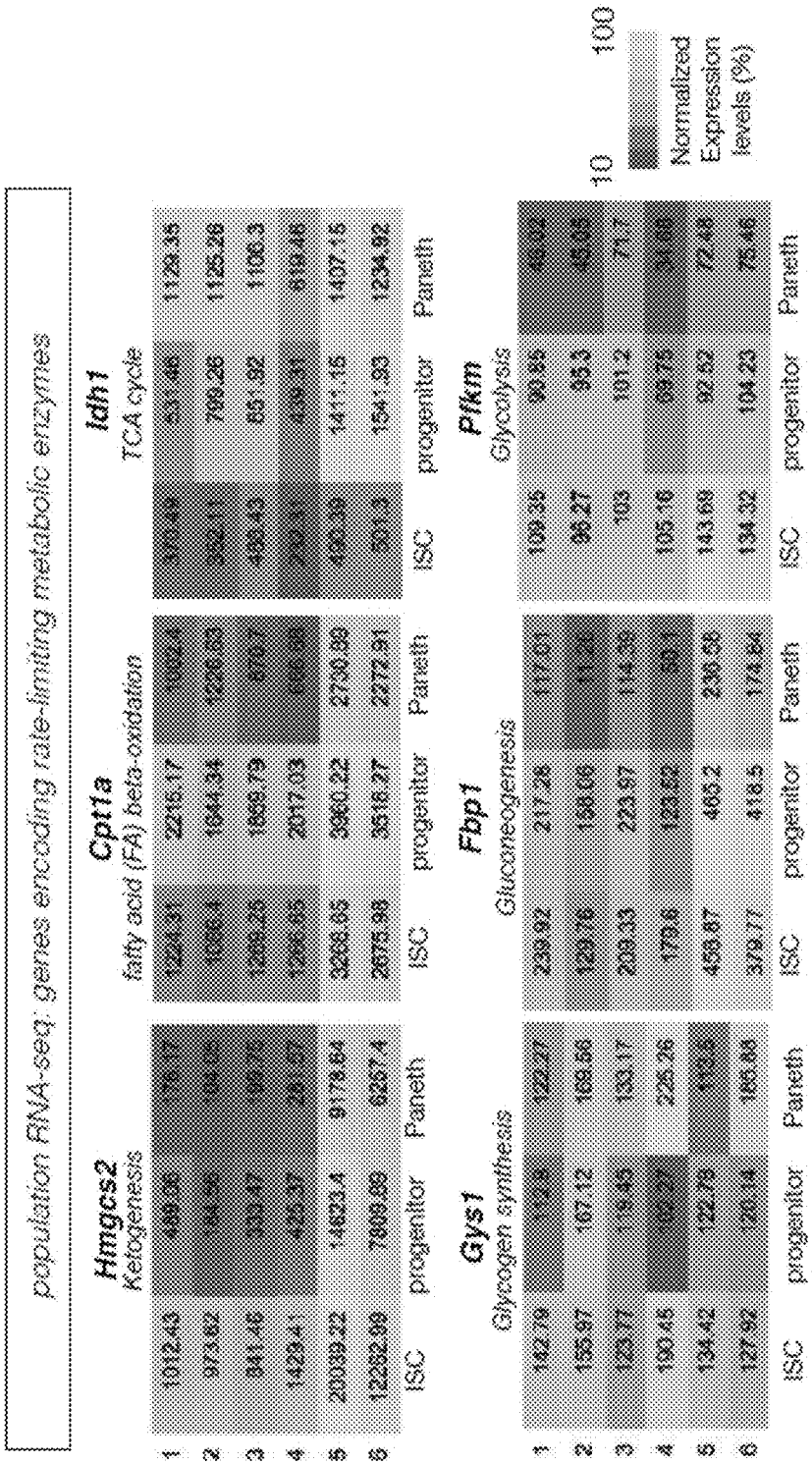
Figures 8J, 8K, 8L:
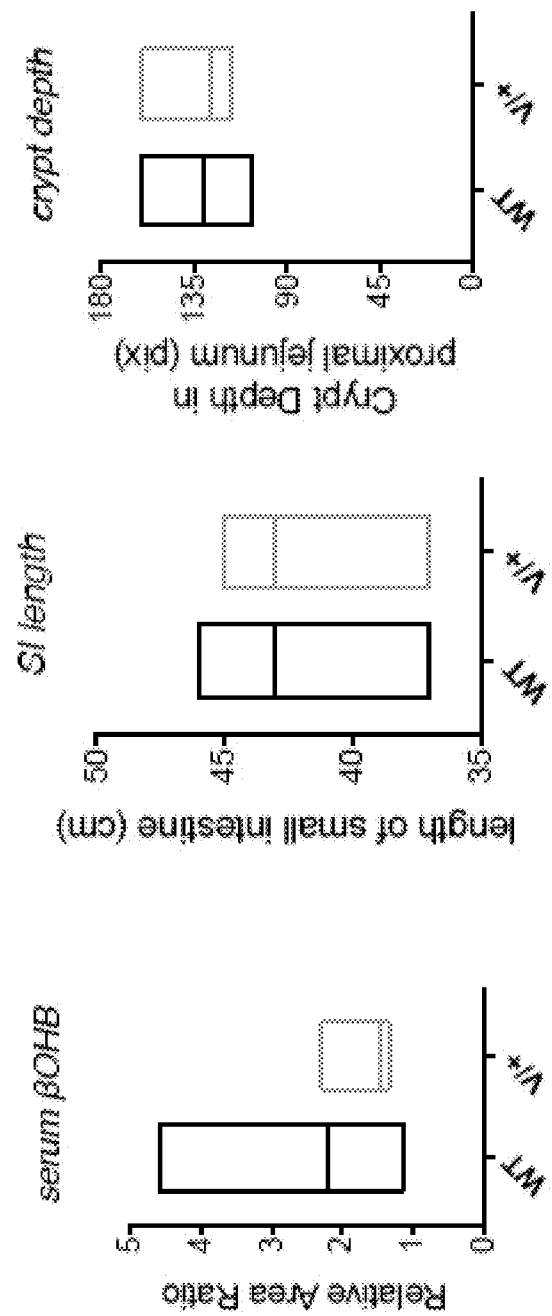

The enrichment of Hmgcs2 expression in Lgr5$^+$ ISCs was verified at both the mRNA and protein levels, by qRT-PCR and immunoblots of flow sorted ISCs, progenitors and Paneth cells (FIGS. 8B and 8C). Single cell immunoblots also illustrated that HMGCS2-expressing cells (HMGCS2$^+$) were highly enriched in the flow sorted Lgr5$^+$ ISCs (77.97%) but less frequent in total intestinal crypt cells (21.17%) (FIG. 8D). Moreover, dual ISH and IHC confirmed the concordance between Lgr5 and Hmgcs2 expression in the intestine (FIG. 1B). Selectively high HMGCS2 expression in the crypt base cells (CBCs) was also observed in human duodenum (FIG. 1C). Expression levels of metabolic genes often fluctuate depending on nutrient availability in diverse dietary regimens (Beyaz et al., 2016; Rodriguez-Colman et al., 2017; Wang et al., 2018; Yilmaz et al., 2012). Notably, unlike the metabolic rate-limiting enzymes of glucose metabolism, TCA cycle, and fatty acid oxidation, Hmgcs2 mRNA expression is robustly enriched in Lgr5$^+$ ISCs compared to progenitors across a range of physiological states (e.g., fed, fasted and old age), even in fasting where it is strongly induced (FIGS. 8E and 8F), raising the possibility that Hmgcs2 plays a key role in the maintenance of Lgr5$^+$ ISCs.

Figures 1E, 1F:
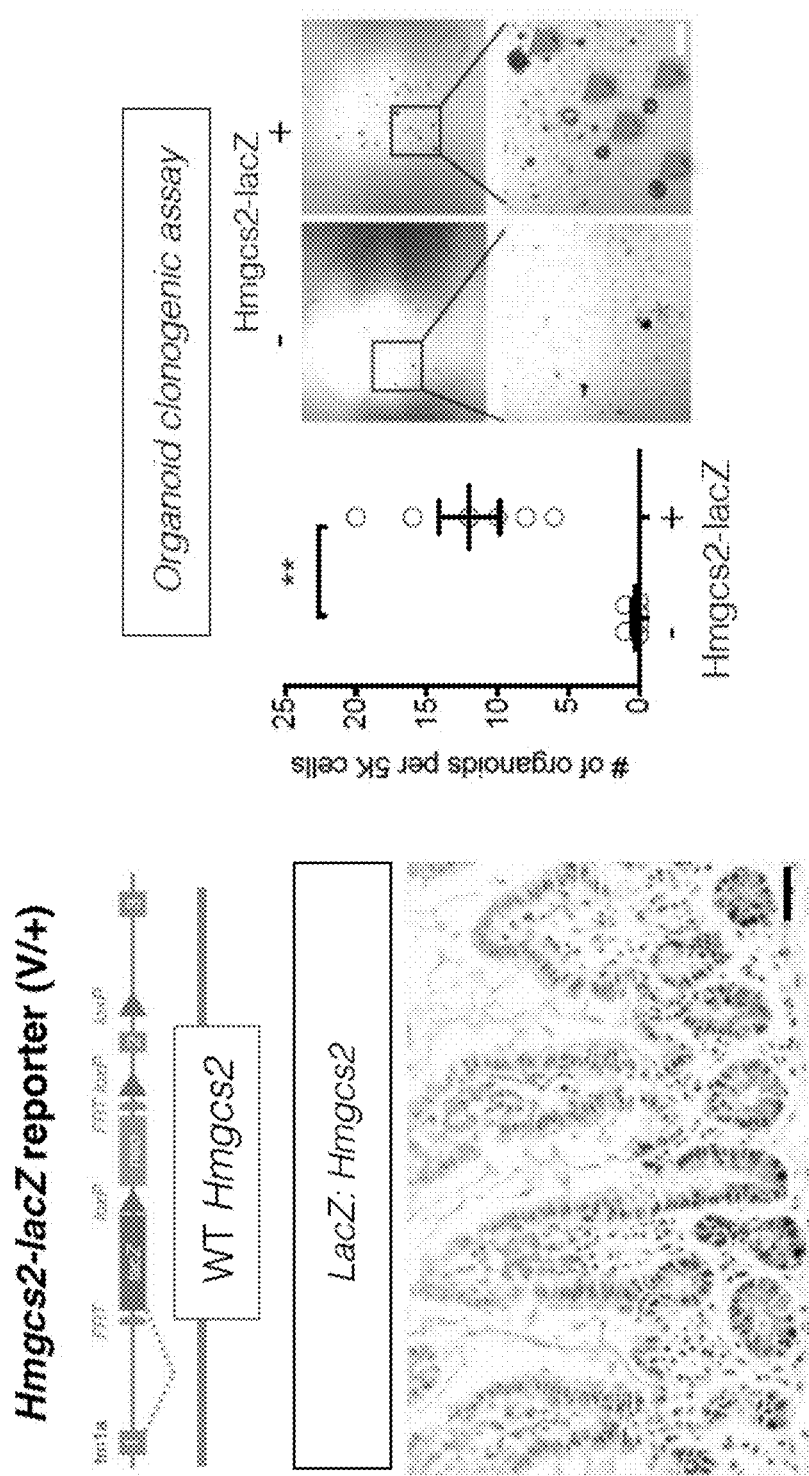

Next, heterozygous Hmgcs2-lacZ (i.e. Hmgcs2$^{V/+}$) reporter mice were engineered (FIGS. 1E and 8G, Methods) to ascertain whether Hmgcs2 expressing (Hmgcs2$^+$) crypt cells possessed functional stem-cell activity in organoid assays. Hmgcs2$^{V/+}$ reporter mice were phenotypically indistinguishable from controls in body mass, causal blood glucose, serum βOHB, small intestinal length and crypt depth (FIGS. 8H-8L). Consistent with ISH and IHC for Hmgcs2 (FIGS. 1B and 1C), β-galactosidase (lacZ) staining of the small intestine from Hmgcs2$^{V/+}$ mice predominantly highlighted CBC cells (FIG. 1E). Functionally, using a fluorescein di-β-D-galactopyranoside (FDG) substrate of lacZ, it was found that the Hmgcs2-lacZ$^+$ fraction of crypt cells possessed nearly all of the organoid propagating activity compared to the LacZ$^-$ fraction (FIG. 1F). This finding together with the strong co-expression of Hmgcs2 in Lgr5+ ISCs (FIGS. 1A-1D, 8B-8D) affirms Hmgcs2 expressing crypt cells as functional stem cells.

Example 2

Loss of Hmgcs2 Compromises Intestinal Stemness and Regeneration

Figure 9F:
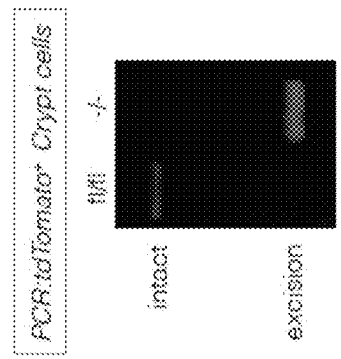

In addition to validating that Hmgcs2 marks Lgr5$^+$ ISCs, Hmgcs2 was conditionally ablated in the entire intestine and specifically in Lgr5$^+$ ISCs to decipher how its loss impacts stem cell maintenance. Three separate tamoxifen-inducible conditional alleles were engineered (Methods): The first model is the Hmgcs2$^{loxp/loxp}$; Villin-CreERT2 conditional intestinal knockout model that disrupts Hmgcs2 in all intestinal epithelial cell types upon tamoxifen administration (FIG. 2A, termed iKO). The second model is the Hmgcs2$^{loxp/loxp}$; Lgr5-EGFP-IRES-CreERT2 reporter mouse, where the Lgr5 knock-in allele has mosaic expression in the intestine and permits the enumeration and isolation of Lgr5-GFP$^{hi}$ ISCs by flow cytometry as well as the deletion of Hmgcs2 in the GFP$^{hi}$ subset of ISCs upon tamoxifen administration (FIGS. 9A and 9B), termed Lgr5-GFP reporter). This model is often used to quantify GFP$^{hi}$ ISCs and GFP$^{low}$ progenitors (Beyaz et al., 2016; Mihaylova et al., 2018; Sato et al., 2009; Yilmaz et al., 2012). The third model is the Hmgcs2$^{loxp/loxp}$; Lgr5-IRES-CreERT2; Rosa26$^{LSL-tdTomato}$ reporter mouse (termed, Lgr5 lineage tracer) that enables the deletion of Hmgcs2 upon tamoxifen administration in nearly all Lgr5$^+$ ISCs and the permanent tdtTomato labeling of the stem cells and their progeny over time (FIGS. 9D-9F). Given that this Lgr5-IRES-CreERT2 allele (Huch et al., 2013) is expressed by nearly all Lgr5$^+$ ISCs, this third model (similar to the first iKO model) enables the quantification of how loss of a gene in ISCs, for example, alters the differentiation of stem-cell derived progeny within the entire intestine and also permits fate mapping from Lgr5$^+$ ISCs (FIG. 9M).

In the iKO model, five doses of tamoxifen were administered starting at postnatal day 7 to iKO and control mice (FIG. 2A). Interestingly, intestinal Hmgcs2 loss reduced the survival of iKO mice where no mortality was noted in the control cohort, and 15 days post-tamoxifen iKO mice had a modest but significant reduction in body mass relative to controls (FIGS. 2A-2C). Also, at this same time point, there was a greater than 2-fold reduction in the numbers of Olfactomedin 4 (OLFM4) positive cells, a marker co-expressed by Lgr5$^+$ ISCs and early progenitors (FIG. 2D) and a greater than 2-fold increase in the numbers of Lysozyme 1 (LYZ1)$^+$ Paneth cells and Alcian Blue (AB)$^+$ goblet cells (FIGS. 2E and 2F). These findings indicate that Hmgcs2 plays an essential role in sustaining ISC numbers and lineage balanced differentiation in the juvenile intestine.

To specifically interrogate the role of Hmgcs2 in adult ISC maintenance, Hmgcs2 was ablated in 12-week-old adult Lgr5-GFP reporter mice for 3 weeks (FIGS. 2G and 9A-9B), which decreased the frequencies of Lgr5-GFP$^{hi}$ ISCs and Lgr5-GFP$^{low}$ progenitors by 50% (FIG. 2H). When co-cultured with WT Paneth cells, flow sorted Hmgcs2-null ISCs engendered 42.9% fewer and 34.6% smaller organoids compared to WT ISCs, indicating that Hmgcs2 loss in ISCs cell-autonomously attenuates organoid-initiating capacity (FIGS. 2I and 9C). Similarly, in the Lgr5-tdTomato lineage tracer mice, Hmgcs2 loss gradually reduced the numbers of OLFM4$^+$ ISCs with no change in the proliferation or apoptosis of ISCs and progenitors (FIGS. 9G, 9J and 9K), small intestinal length (FIG. 9H) or crypt depth (FIG. 9I). As observed in the iKO model, the reduction in the numbers of OLFM4$^+$ ISCs was accompanied by increases in the numbers of Paneth cells and goblet cells (FIG. 9G); however, the numbers of chromogranin A+ enteroendocrine cells in the crypts were not affected (FIG. 9L). Loss of Hmgcs2 in adult intestines not only dampens ISC self-renewal (i.e., fewer ISC numbers with less organoid-forming potential) but also shifts early differentiation within the crypt towards the secretory lineage (i.e., greater numbers of Paneth and goblet cells).

Figure 2L:
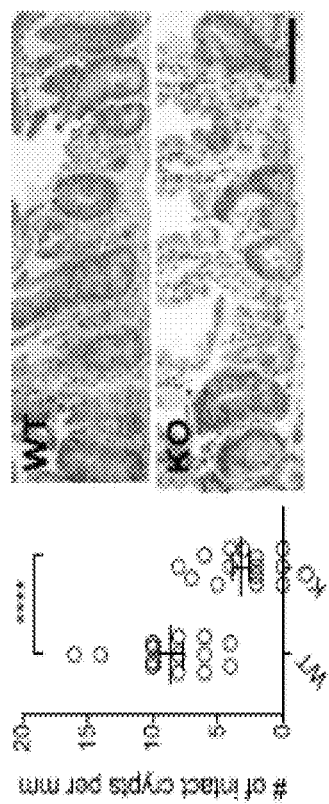
Figure 2J:
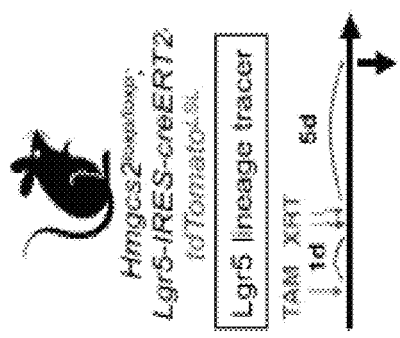

Lgr5$^+$ ISCs drive intestinal maintenance in homeostasis and regeneration in response to injury such as from radiation-induced damage (Beumer and Clevers, 2016; Metcalfe et al., 2014). tdTomato expression and Hmgcs2 excision were induced in the Lgr5$^+$ ISCs with tamoxifen one day prior to radiation-induced intestinal epithelial injury to ascertain whether Hmgcs2 affected the in vivo ability of these ISCs to regenerate the intestinal lining (FIG. 2J). The efficiency of regeneration was assessed by quantifying the number of tdTomato+ clonal progeny generated from the Lgr5$^+$ ISCs 5 days post-radiation exposure and the number of intact crypt units per length of intestine: First, Hmgcs2-null ISCs generated 5-fold fewer labeled tdTomato+ crypts (FIGS. 2J and 2K) with fewer labeled progeny extending up crypt-villous units as was observed in controls (FIG. 9M). Second, loss of Hmgcs2 also diminished the overall number of surviving intact crypts by 2-fold compared to controls (FIG. 2L). Thus, these data demonstrate that Hmgc2 is critical for Lgr5+ ISC-mediated repair in vivo after injury.

Example 3

HMGCS2 Regulates Secretory Differentiation Through NOTCH Signaling

To gain mechanistic insight into how Hmgcs2 impacts the differentiation of ISCs, droplet-based scRNA-seq (FIG. 3A, Methods) was performed on the sorted tdTomato$^+$ progeny of WT and Hmgcs2-null ISCs five days after tamoxifen injection, a time point prior to the reduction in the number of Hmgcs2-null ISCs (FIG. 2D) (Haber et al., 2017), chosen to allow to capture early changes in regulatory programs. Cell-type clustering based on the expression of known marker genes partitioned the crypt cells into seven cell types (FIGS. 3B, 3C, 10A-10C, see also Tables S2 and S3 of Cheng, C.-W., Ketone Body Signaling Mediates Intestinal Stem Cell Homeostasis and Adaptation to Diet, Cell 178, 1115-1131, Aug. 22, 2019, the contents of which are incorporated herein by reference in their entirety, and Methods) (Haber et al., 2017).

Figure 3B:
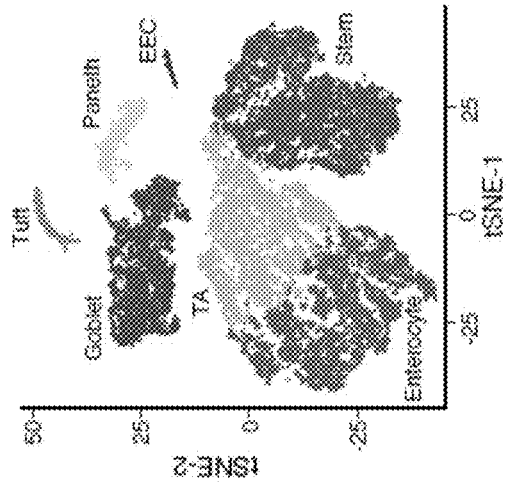
Figure 3D:
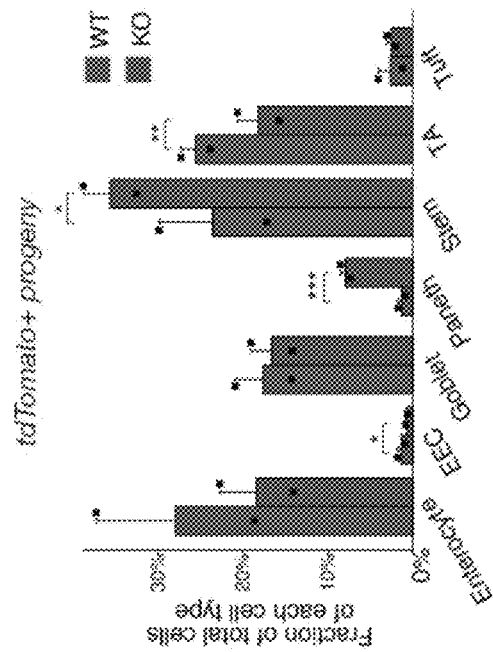
Figure 3A:
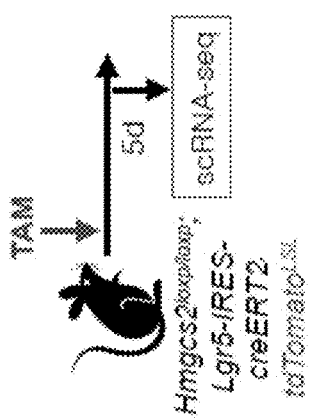
Figure 3C:
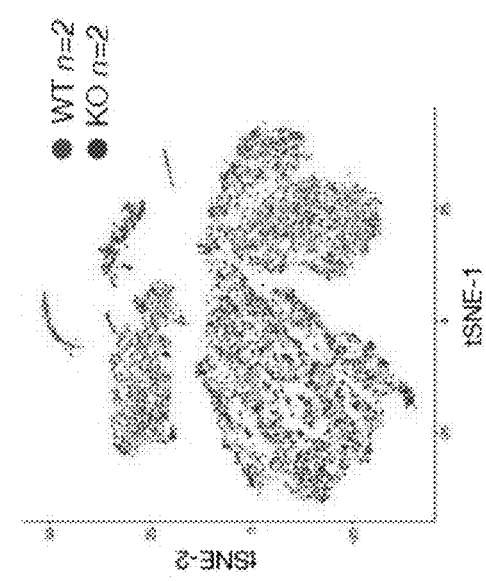
Figure 10A:
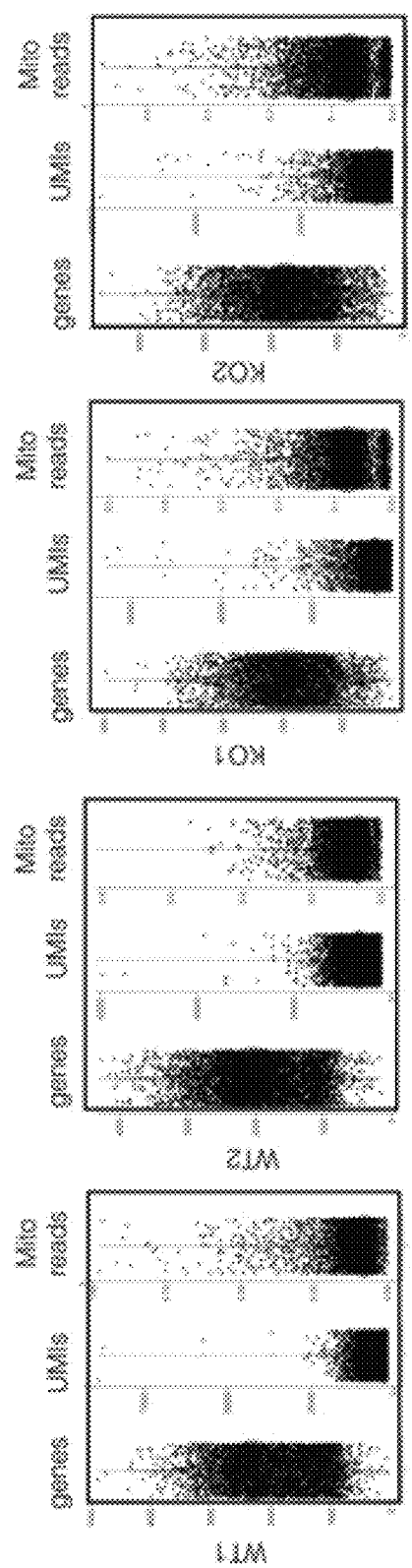
FIGS. 10A-10H show single-cell RNA-seq analysis of WT and Hmgcs2-KO ISCs and early cell progenies. Related to FIG. 3.
Figure 10B:
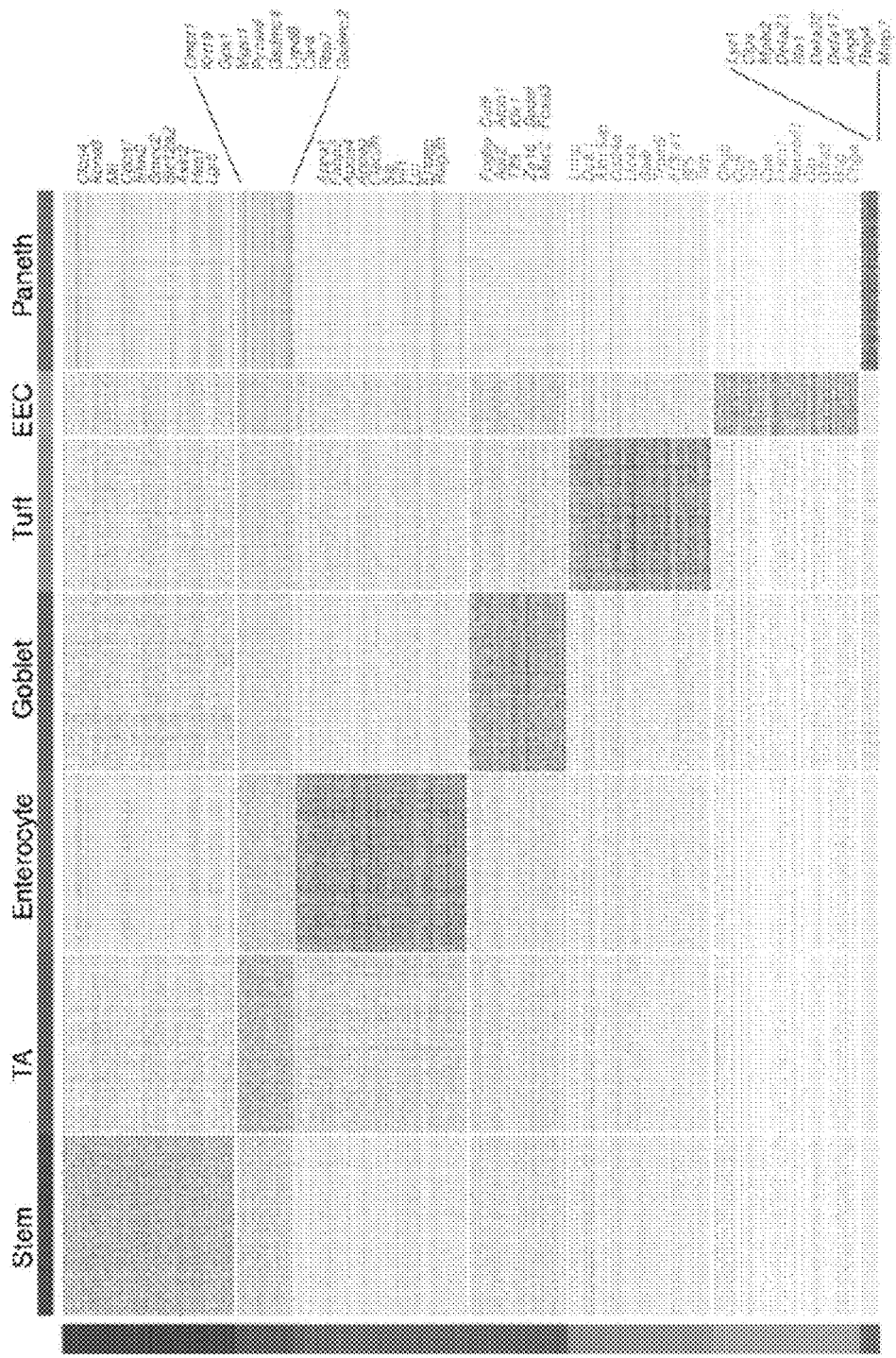
Figure 10C:
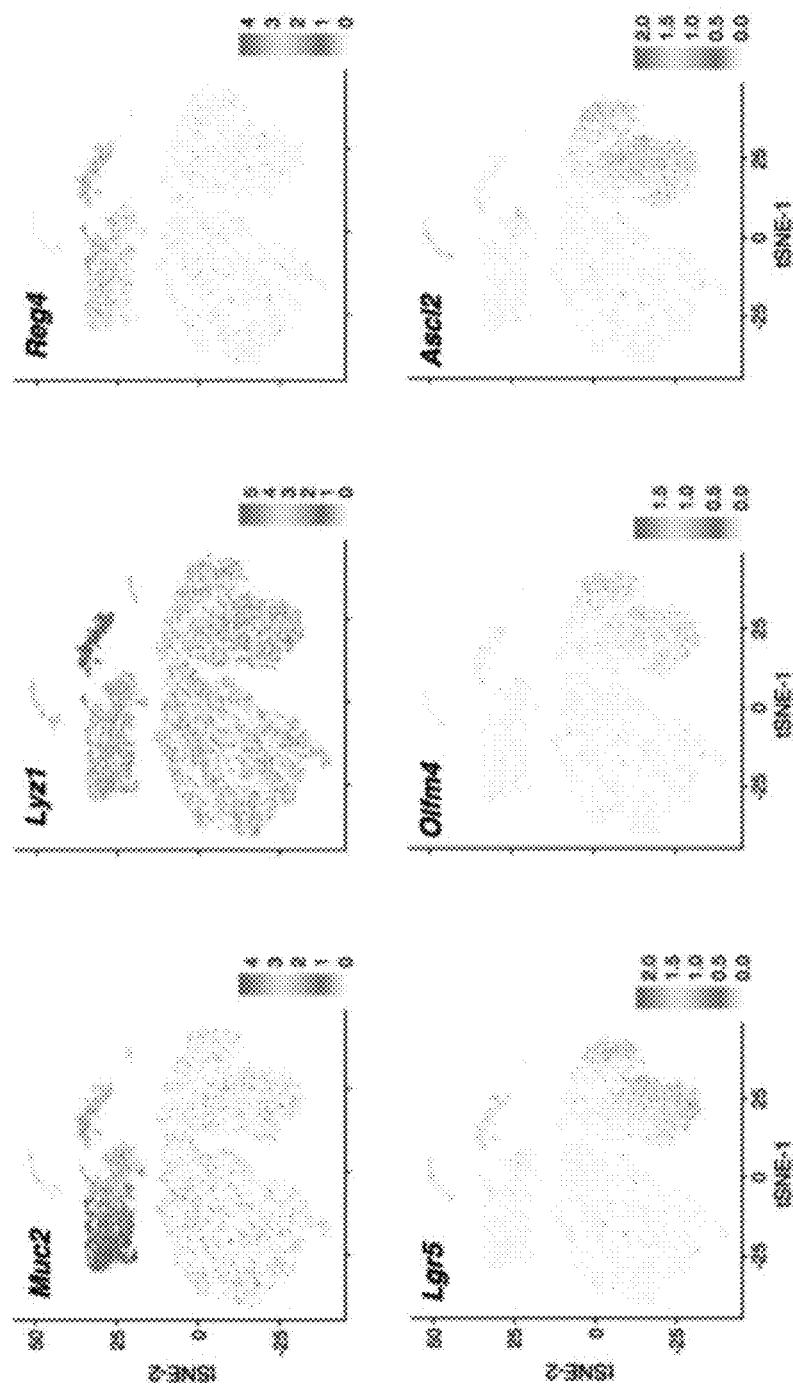
Figures 10D, 10E, 10F:
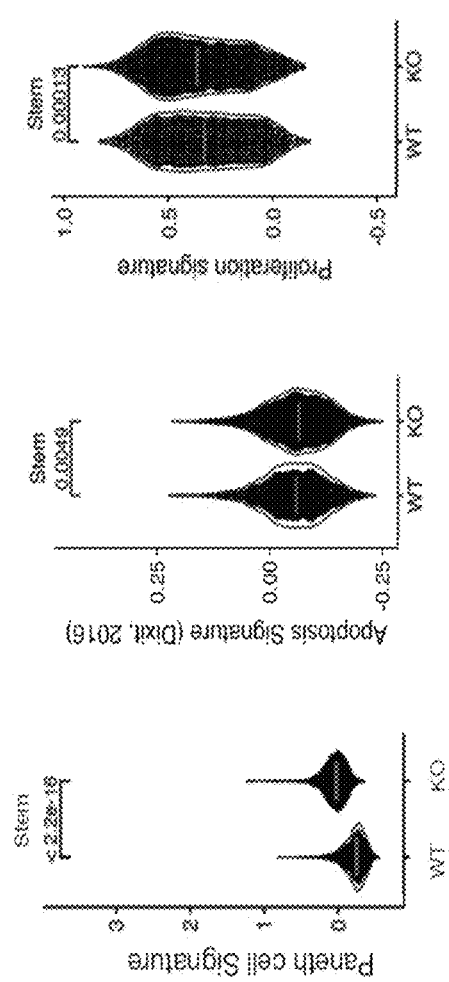

Acute deletion of Hmgcs2 in ISCs led to a modest increase in stem cells (35.34% compared to 22.96% by WT ISCs), fewer transient amplifying/bipotential progenitors (Kim et al., 2016) (TA, 18.40% compared to 25.73% by WT ISCs) and a pronounced 5.8-fold expansion of Paneth cells (7.88% compared to 1.36% by WT ISCs) (FIG. 3D; see also Table S2 of Cheng, C.-W., Ketone Body Signaling Mediates Intestinal Stem Cell Homeostasis and Adaptation to Diet, Cell 178, 1115-1131, Aug. 22, 2019, the contents of which are incorporated herein by reference in their entirety). Further analysis of ISC profiles revealed that while Hmgcs2-loss weakened the Lgr5$^+$ stemness signature (Munoz et al., 2012a) in ISCs (FIG. 3E), it had only minor effects on proliferation and apoptosis signatures (FIGS. 10E and 10F). Together with the progressive loss of ISCs and the shift towards Paneth and goblet cell differentiation observed at the later time points after induction of Hmgcs2 deletion (FIGS. 2B and 2D-2F), these data support the notion that Hmgcs2 loss compromises stemness and skews their differentiation towards the secretory lineage.

These findings prompted investigation for signs of premature differentiation in Hmgcs2-null ISCs, which surprisingly show up-regulation of Paneth cell signature genes (FIG. 3F). While six days after Hmgcs2 loss in ISCs had no effect on the numbers of tdTomato+ stem cells (Lgr5-GFP$^{hi}$) or progenitors (Lgr5-GFP$^{low}$) (FIG. 10H), Hmgcs2-null ISCs engendered substantially greater numbers of tdTomato+ Paneth cells after as few as 24 hours of deletion in jejunal sections (FIGS. 3G and 10G) and after 6 days of deletion by flow cytometry (FIG. 10H).

Figure 3I:
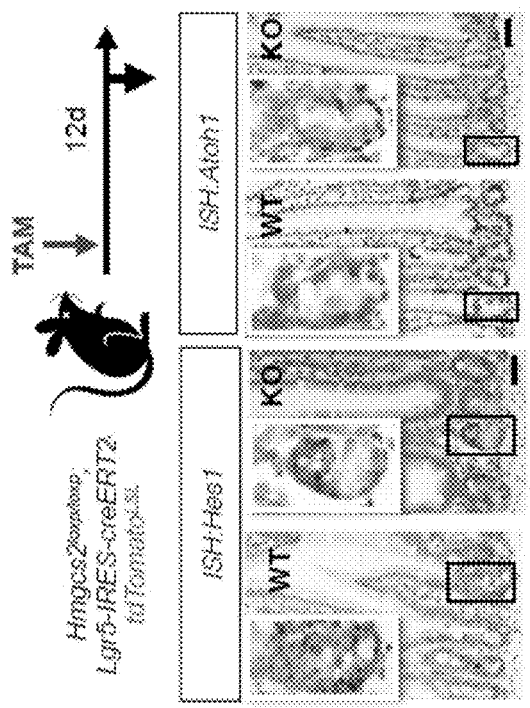
Figure 3H:
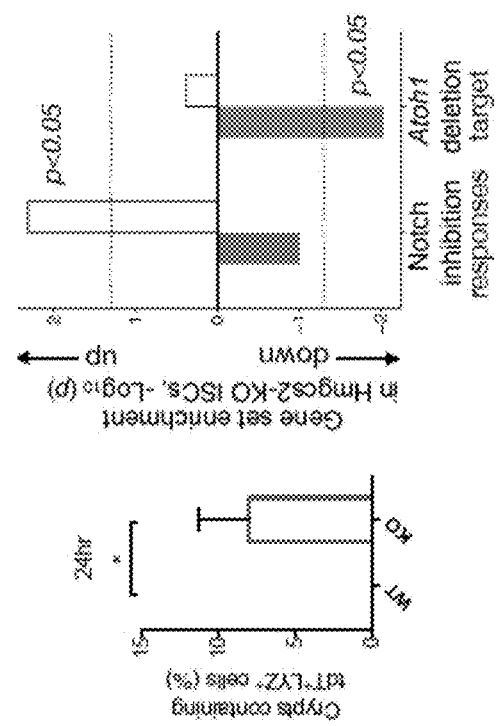

In the mammalian intestine, Notch signaling activates Olfm4 transcription (a co-marker for Lgr5+ ISCs), maintains ISC self-renewal, and skews differentiation towards absorptive cell fates, which involves repressing atonal homolog 1 (Atoh1) transcription by the hairy and enhancer of split 1 (Hes1) transcription factor (Sancho et al., 2015). This sequence of events permits stem cell self-renewal and prevents differentiation to the secretory lineage (Sancho et al., 2015; VanDussen et al., 2012). Indeed, the rapid adoption of early secretory Paneth cell fates by Hmgcs2-null ISCs is compatible with a Notch-deficient phenotype (Sancho et al., 2015; Tian et al., 2015), which is confirmed by gene set enrichment analysis (GSEA) in Hmgcs2-null versus control ISCs: Notch inhibition responsive genes were significantly upregulated, and Atoh1 deletion target genes were significantly down-regulated in Hmgcs2-null ISCs compared to WT ISCs (FIG. 3H) (Kim et al., 2014). The induction of Atoh1 transcripts was validated and the reduction of its negative regulator Hes1 by ISH in Hmgcs2-null intestinal crypt cells compared to controls (FIG. 3I). Lastly, enforced expression of the constitutively active Notch intracellular domain (NICD) rescued the organoid-forming capacity of Hmgcs2-null cells (FIG. 3J), thereby supporting the paradigm that HMGCS2 actuates ISCs function through NOTCH signaling.

Example 4

β-Hydroxybutyrate (βOHB) Compensates for Hmgcs2 Loss in ISCs

Figure 4E:
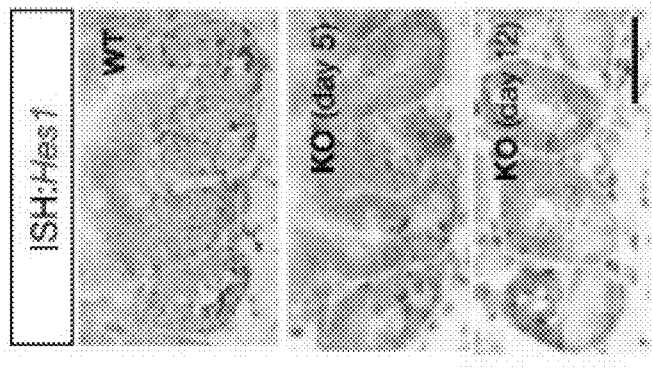
Figure 4D:
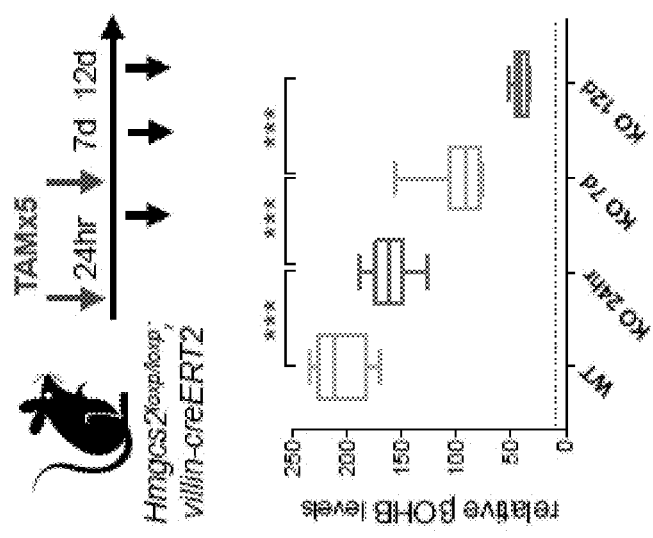
Figure 11A:
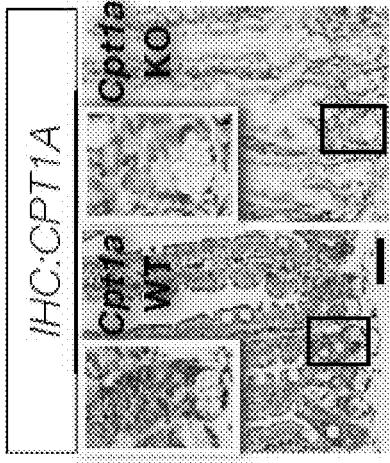
FIGS. 11A-11N. Characterization of fatty acid oxidation (FAO) and ketogenesis in intestinal crypts. Related to FIG. 4.
Figure 11B:
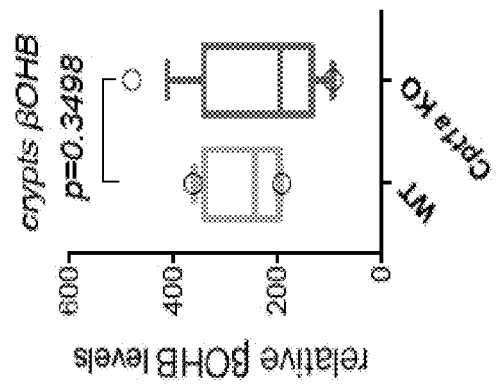
FIG. 11B, Immunohistochemistry (IHC) for CPT1a (rate limiting step of FAO) and FIG. 11C, HMGCS2 levels in WT and intestinal Cpt1a loss. Images represent one of 5 biological replicates per group.
Figure 11C:
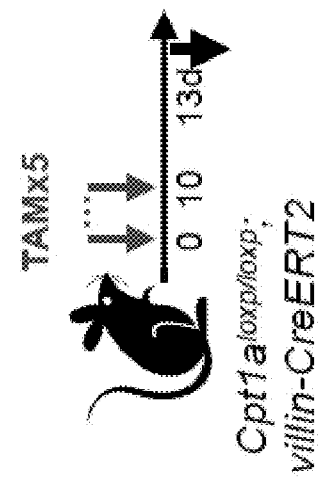
FIG. 11D, βOHB levels in Cpt1a-null intestinal crypts. n=8 measurements for 4 mice per group.
FIG. 11E, IHC for Lysozyme, demonstrating the absence of LYZ+ Paneth cell in Atoh1-KO mice. The image represents one of 8 biological replicates.
FIG. 11F, IHC for HMGCS2, indicating intact HMGCS2 expression in the absence of Paneth cell. The image represents one of 8 biological replicates. For FIGS. 11C-11F, Scale bar: 50 um.
FIG. 11G, Schematic of the mouse model for intestinal Hmgcs2 deletion with the timeline for TAM injections and tissue collection.
FIG. 11H, Hepatic and intestinal HMGCS2 expression by IHC and FIG. 11I, serum βOHB levels in Hmgcs2-KO mice.
FIG. 11J, Intestinal CPT1a expression in mice with conditional intestinal loss of Hmgcs2 by IHC, Scale bar: 100 um. The image represents one of 5 biological replicates.
FIG. 11K, Loss of intestinal HMGCS2 resulted in no change in FAO activity based upon the contribution of [U-13C] palmitate to acetylcarnitine and citrate. n=6 mice per group.
FIG. 11L, Organoid-forming assay for number of organoids per intestinal crypt, numbers of Alcian blue+ goblet cells (black arrows) and percentage of tdTomato+ area per organoid from WT and Hmgcs2-KO (−/−) ISCs, ±βOHB treatments: +, 10 uM and ++50 uM. Representative images: day-5-to-7 organoids. Scale bar: 50 μm. n=5 mice.
FIG. 11M, Lactate treatments at comparable concentrations with β-OHB did not affect the organoid-forming capacity of Hmgcs2-null ISCs. N, Synthesis of glycerol tri((R)-3-hydroxybutyrate).
Figure 11D:
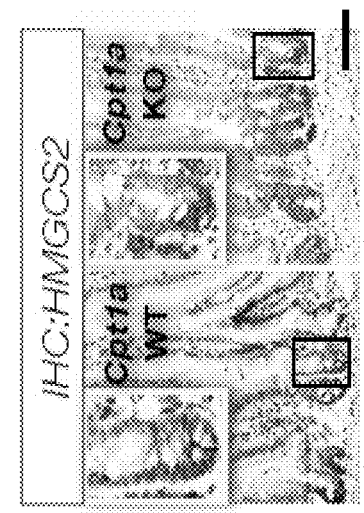
Figure 11E:
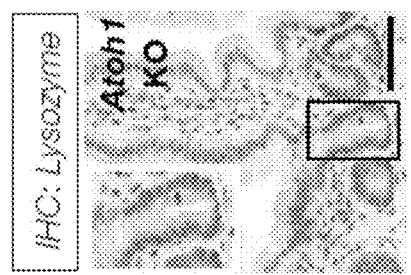
Figure 11F:
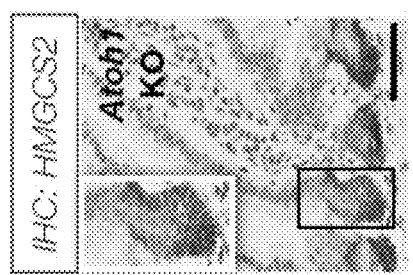
Figure 11G:
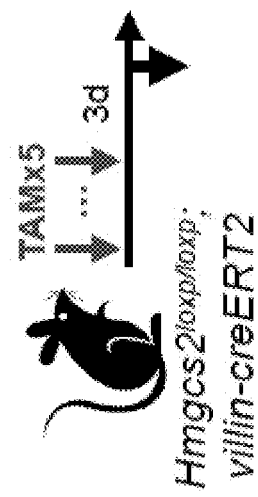
Figure 11H:
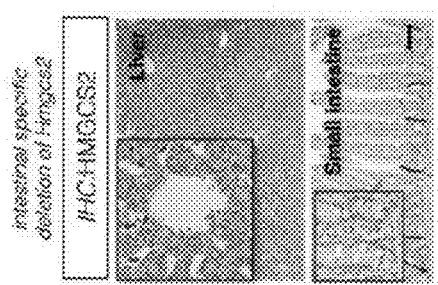
Figure 11I:
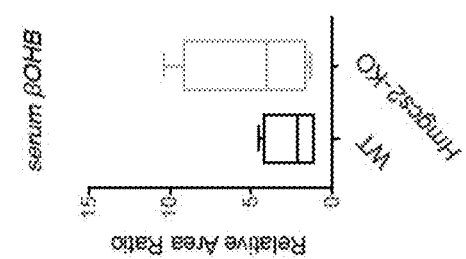

HMGCS2 catalyzes the formation of HMG-CoA from acetoacetyl-CoA and acetyl-CoA, a rate-limiting step of ketone body production (i.e. ketogenesis, FIG. 4A). While Hmgcs2 was selectively expressed in ISCs compared to progenitors and Paneth cells, genes encoding other ketogenic enzymes including Acetyl-CoA acetyltransferase 1 (Acat1), Hmg-CoA lyase (Hmgcl) and 3-Hydroxybutyrate Dehydrogenase 1 (Bdh1) were broadly expressed in both stem and progenitor cells compared to Paneth cells, based on the results of both population and scRNA-Seq (FIG. 4A) (Adijanto et al., 2014). Consistent with these expression patterns, measured βOHB levels were highest in Lgr5-GFP$^{hi}$ ISCs followed by Lgr5-GFP$^{low}$ progenitors and then Paneth cells (FIG. 4B), which was near the detection threshold in sorted intestinal ISCs and progenitors after Hmgcs2 loss (dotted line in FIG. 4B). In addition, genetic ablation of the Paneth cells, which provide paracrine metabolites to ISCs (Rodriguez-Colman et al., 2017), in an intestinal Atoh1-null model (Durand et al., 2012; Kim et al., 2012b) did not alter crypt expression of HMGCS2 protein or βOHB levels (FIGS. 4C, 11E-11F), highlighting that HMGCS2-mediated ketogenesis in crypt cells generate ketone bodies independent of Paneth cells. Finally, genetic ablation of Hmgcs2 in all intestinal epithelial cells using adult iKO mice diminished βOHB levels over time in crypts (FIG. 4D) with no impact on hepatic HMGCS2 protein expression and serum βOHB levels (FIGS. 11H-11I). Interestingly, crypt βOHB levels after Hmgcs2 loss also correlated with a decline in Hes1 ISH expression over time (FIG. 4E), highlighting that maximal reduction in Notch activity is observed at the nadir of βOHB depletion.

Figure 11J:
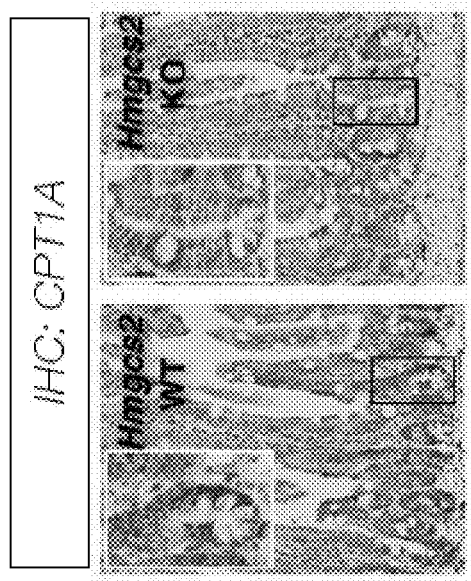
Figure 11K:
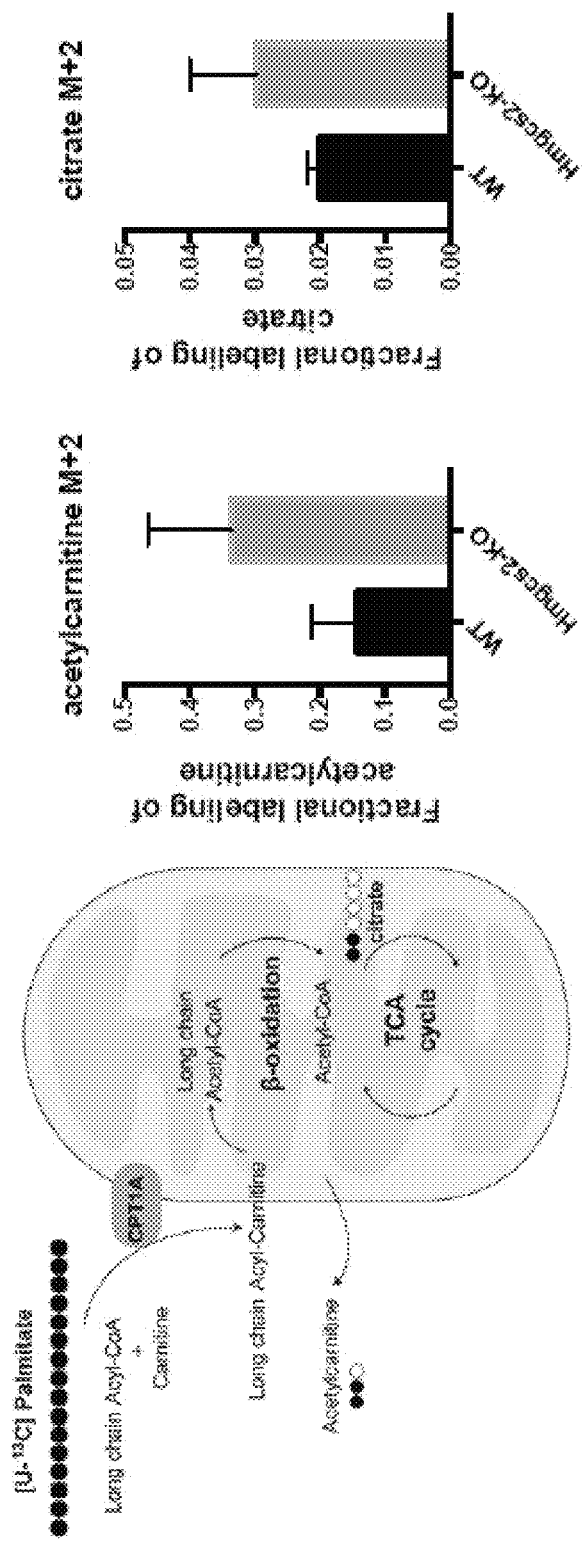

A role for fatty acid oxidation (FAO) in the long-term maintenance of Lgr5+ ISCs was recently described, whose end product acetyl-CoA can feed into ketogenesis and other metabolic pathways. Genetic loss of intestinal Cpt1a (Carnitine palmitoyltransferase I), the rate-limiting step of FAO, resulted in compensatory elevation of HMGCS2 protein expression and in stable crypt βOHB concentrations (FIG. 11A-11D). Conversely, loss of Hmgcs2 in all intestinal epithelial cells had no impact on intestinal CPT1a protein levels or on FAO in Hmgcs2-null crypts (FIGS. 11J-11K). Although intestinal loss of either Cpt1a or Hmgcs2 diminishes Lgr5+ ISC numbers, Cpt1a loss has no effect on intestinal differentiation (Mihaylova et al., 2018) whereas Hmgcs2 loss skews differentiation towards the secretory lineage (FIGS. 2E, 2F and 3G). Taken together, these findings indicate that FAO and ketogenesis maintain intestinal stem and progenitor cell activity partly through independent mechanisms.

Figure 4F:
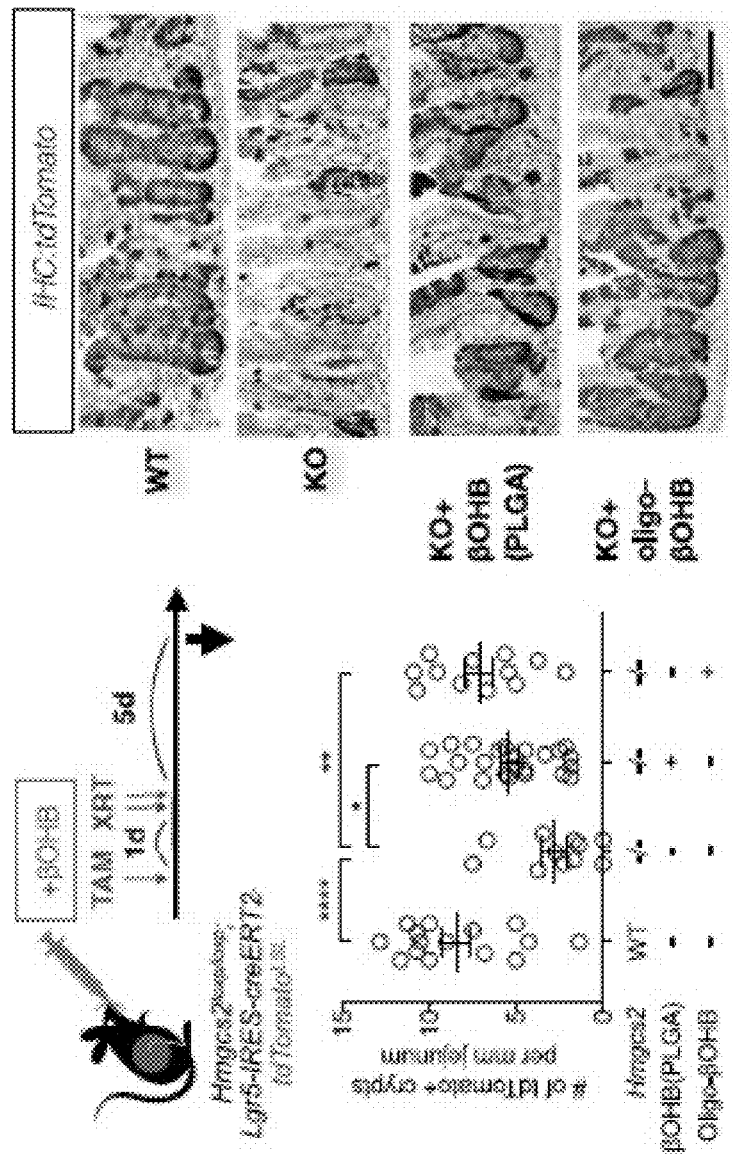
Figure 11L:
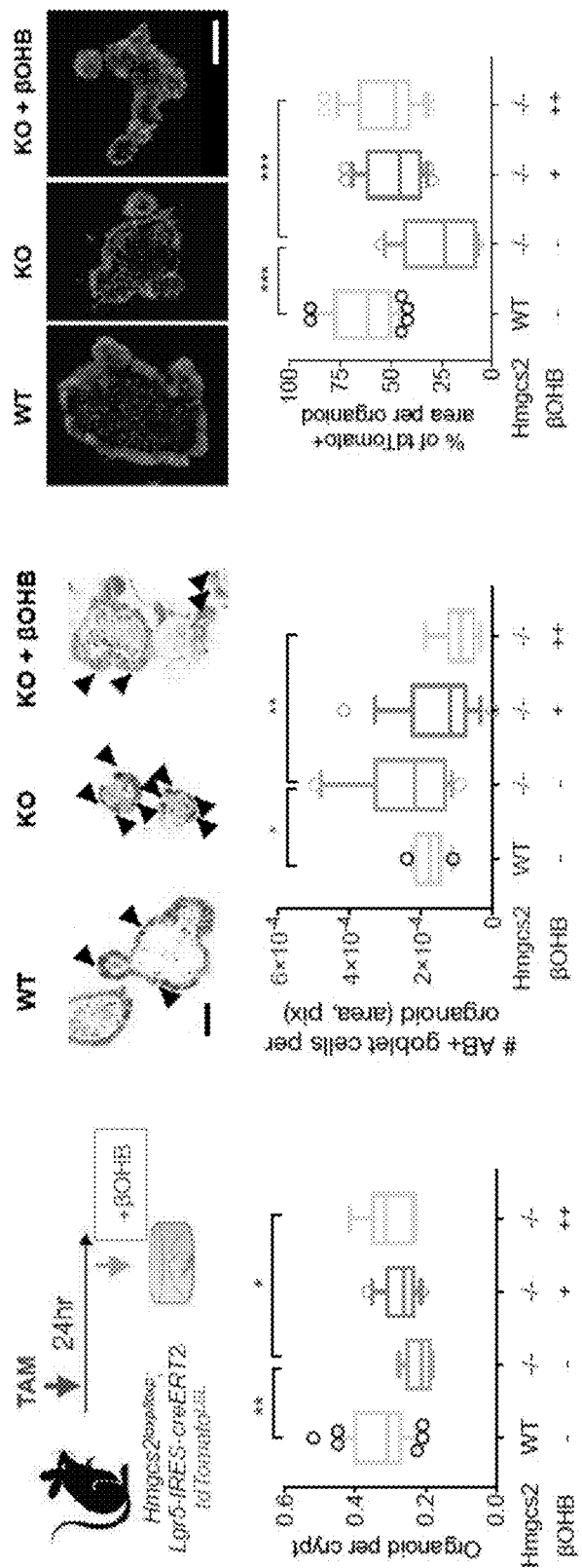
Figure 11M:
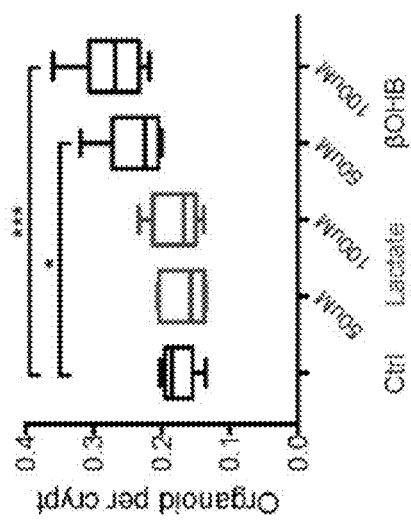
Figure 11N:
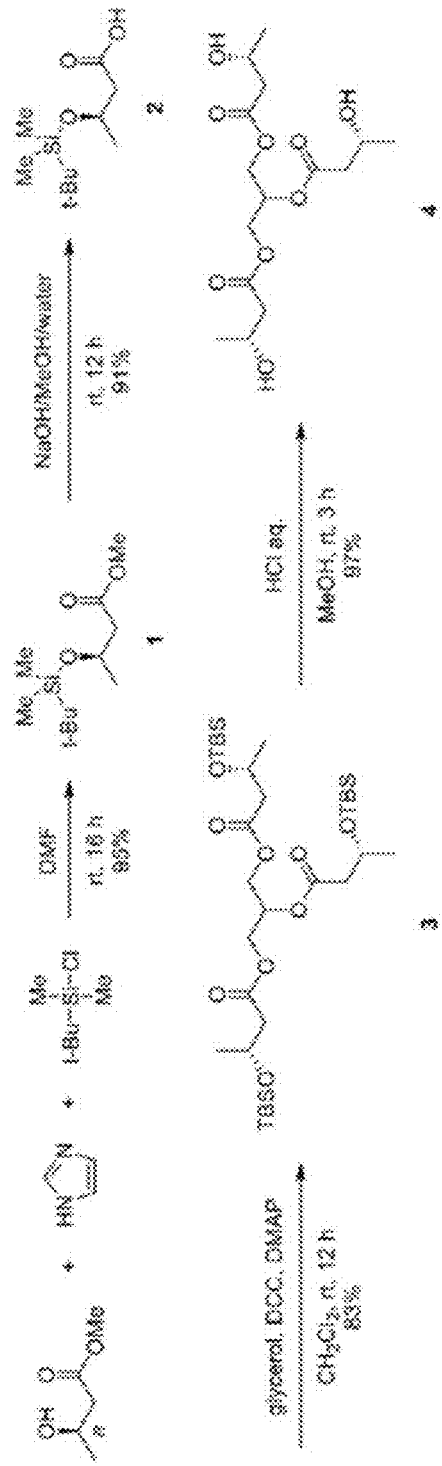

It was next examined whether βOHB rescues the function and secretory differentiation phenotype of Hmgcs2-null organoids. To address this question, tamoxifen was administered to control and Hmgcs2$^{loxp/loxp}$; Lgr5-tdTomato lineage tracer mice 24 hours before crypt isolation (FIG. 11L). Crypts with Hmgcs2-null ISCs were then cultured in standard media, with or without βOHB. Compared to controls, crypts with Hmgcs2-null ISCs were 34.4% less capable of forming organoids and the resulting organoids showed a 40.5% increase in goblet cells and a 64.3% decline in tdTomato+ cells per organoid (FIG. 11L). These results indicate that Hmgcs2-null ISCs in vitro are less functional and are biased towards secretory differentiation as is seen in vivo. Exogenous βOHB but not lactate, a Paneth niche derived metabolite that sustains ISC function (Rodriguez-Colman et al., 2017), rectified these functional deficiencies (i.e., organoid-forming capacity and generation of tdTomato+ clones) and the secretory lineage bias of Hmgcs2-null organoids (FIGS. 11L and 11M). To investigate whether βOHB also compensates for the loss of intestinal HMGCS2 activity in vivo, two modified forms of βOHB were developed and delivered to the gastrointestinal tract of Hmgcs2-KO mice (FIG. 11N). Oral administration of poly(lactic-co-glycolic acid) (PLGA) encapsulated βOHB nanoparticles or βOHB oligomers (FIG. 11N) partially restored intestinal regeneration after radiation-induced damage, which otherwise was severely impaired upon Hmgcs2 intestinal deletion (FIG. 4F). Thus, βOHB is sufficient to substitute for HMGCS2 activity in ISCs and may serve as a biochemical link between the HMGCS2 and the NOTCH signaling pathways.

Example 5

βOHB Mediated Class 1 HDAC Inhibition Enhances NOTCH Signaling

Figures 5A, 5B:
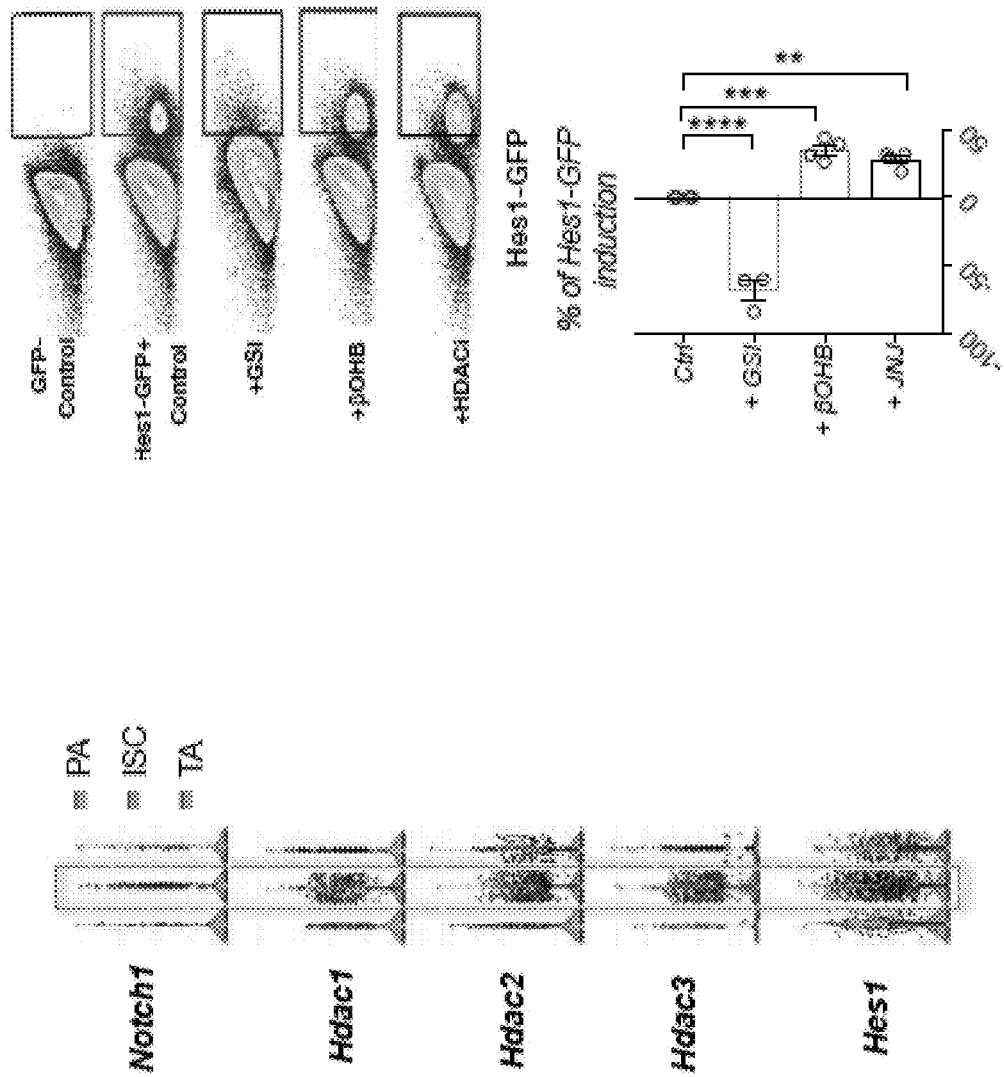
FIGS. 5A-5G show βOHB-mediated HDAC inhibition enhances NOTCH signaling.
Figure 12C:
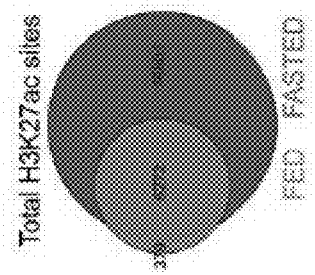
FIGS. 12A-12I show βOHB regulates ISC function via HDAC inhibition. Related to FIG. 5.
Figure 12B:
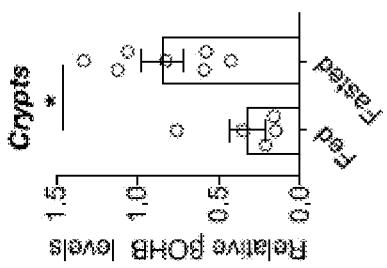
Figure 12E:
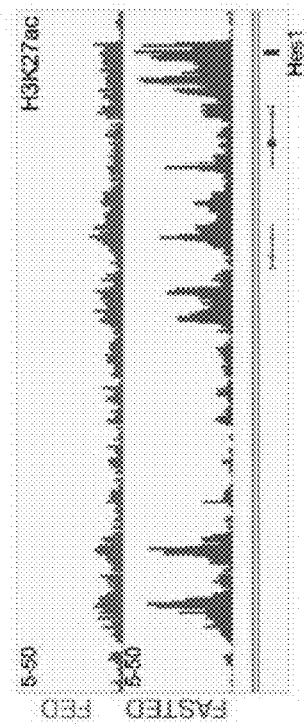
Figure 12A:
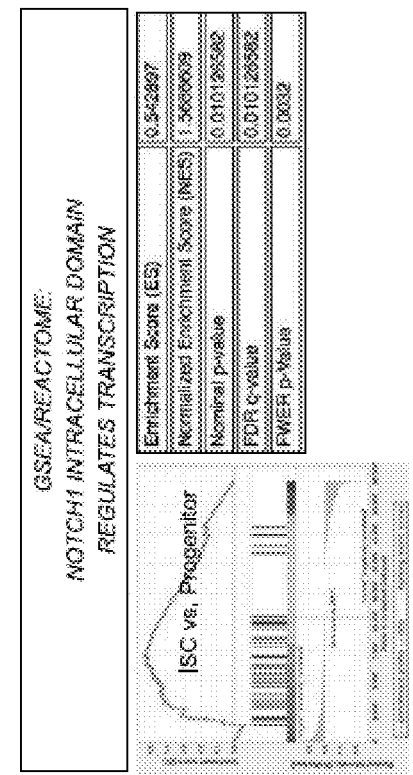

HMGCS2 is a mitochondrial matrix enzyme and unlikely to physically interact with the NOTCH transcriptional machinery, so the regulatory role of its metabolic product βOHB was explored, which has been reported to be an endogenous inhibitor for class I HDACs (Shimazu et al., 2013). Although the link between HDAC and NOTCH is not well delineated in the mammalian intestine, experimental evidence in model organisms (Yamaguchi et al., 2005) and in other tissues (Hsieh et al., 1999; Kao et al., 1998; Oswald et al., 2002) suggest that HDACs can transcriptionally repress NOTCH target genes. Consistent with this possibility, an earlier study found that the addition of HDAC inhibitors to organoid cultures decreases the niche dependency of Lgr5$^+$ ISCs partly through NOTCH activation (Yin et al., 2014). The published population-based RNA-seq and scRNA-Seq dataset (Haber et al., 2017) revealed that Notch receptor (e.g. Notch1), Hdacs (e.g. Hdac1, Hdac2 and Hdac3) and Notch target genes (e.g. Hes1) are enriched in ISCs. Notch and HDACs, ranked as the 2nd highest signature of ISCs from the MSigDB c2 collection of 2864 transcriptional pathways (FIGS. 5A and 12A). These analyses indicate that ISCs display high Notch activity despite enrichment for repressive HDACs. To test whether enzymatic inhibition of HDACs by βOHB activates NOTCH target gene expression such as Hes1, Hes1-GFP organoids were exposed to βOHB and HDAC1 inhibitor Quisinostat (JNJ-26481585, JNJ) (FIG. 5B). Both interventions increased GFP expression compared to control while, as expected, treatment with a γ-secretase inhibitor (GSI, a NOTCH inhibitor) dampened GFP expression.

Figure 5C:
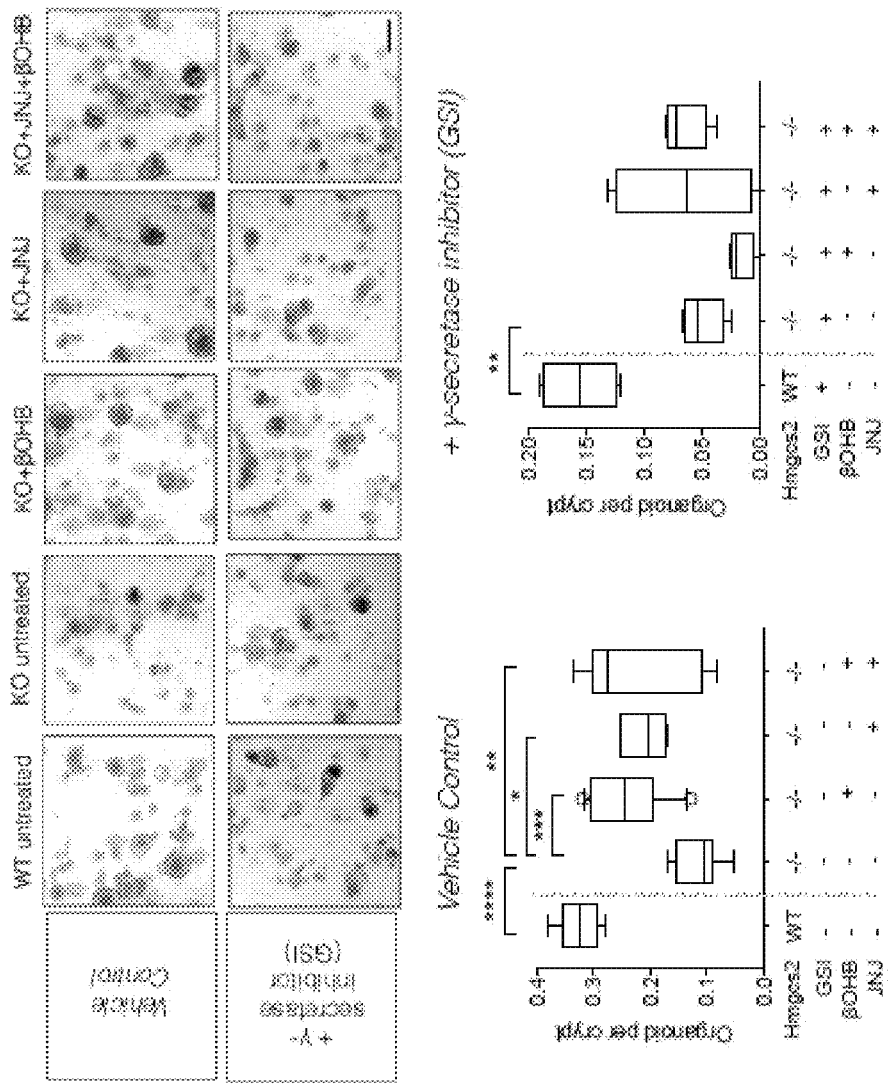
Figure 7A:
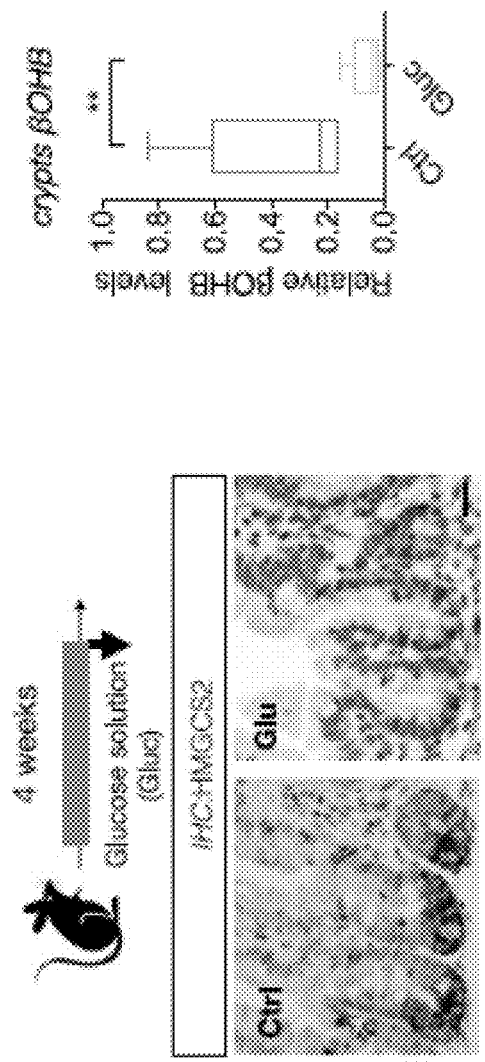
FIGS. 7A-7F show dietary glucose dampens intestinal ketogenesis and stemness.
Figure 7B:
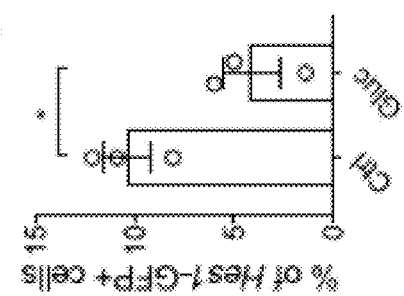
Figure 7C:
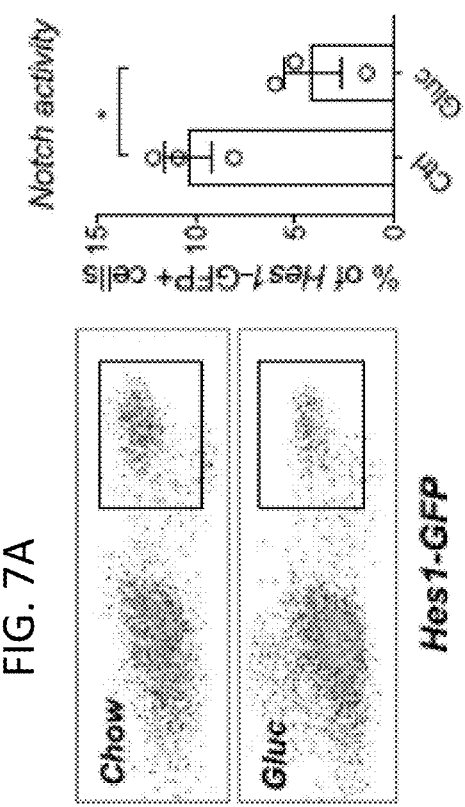
Figure 7E:
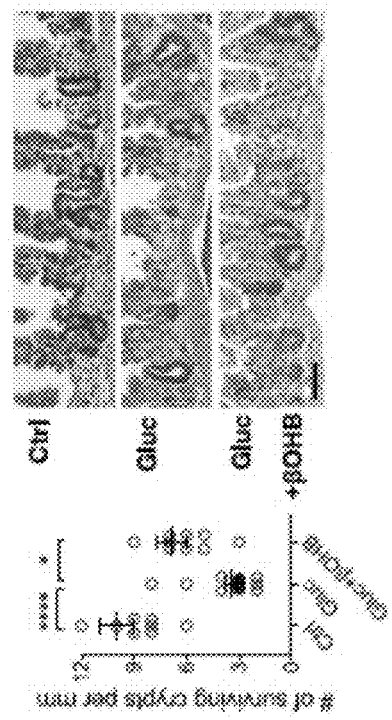
Figure 7D:
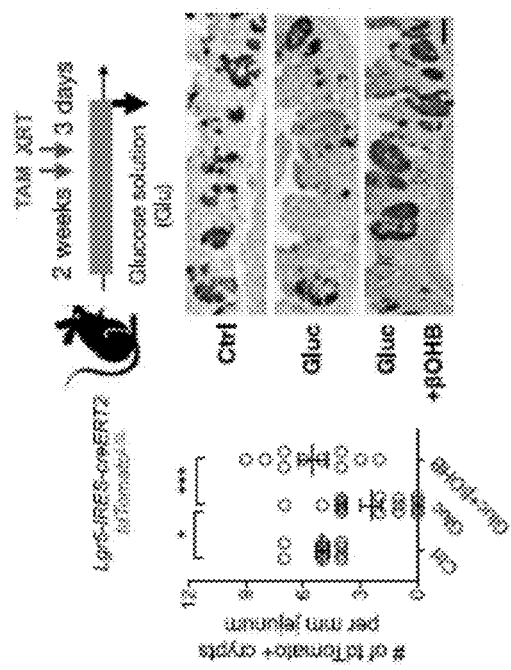
Figure 7F:
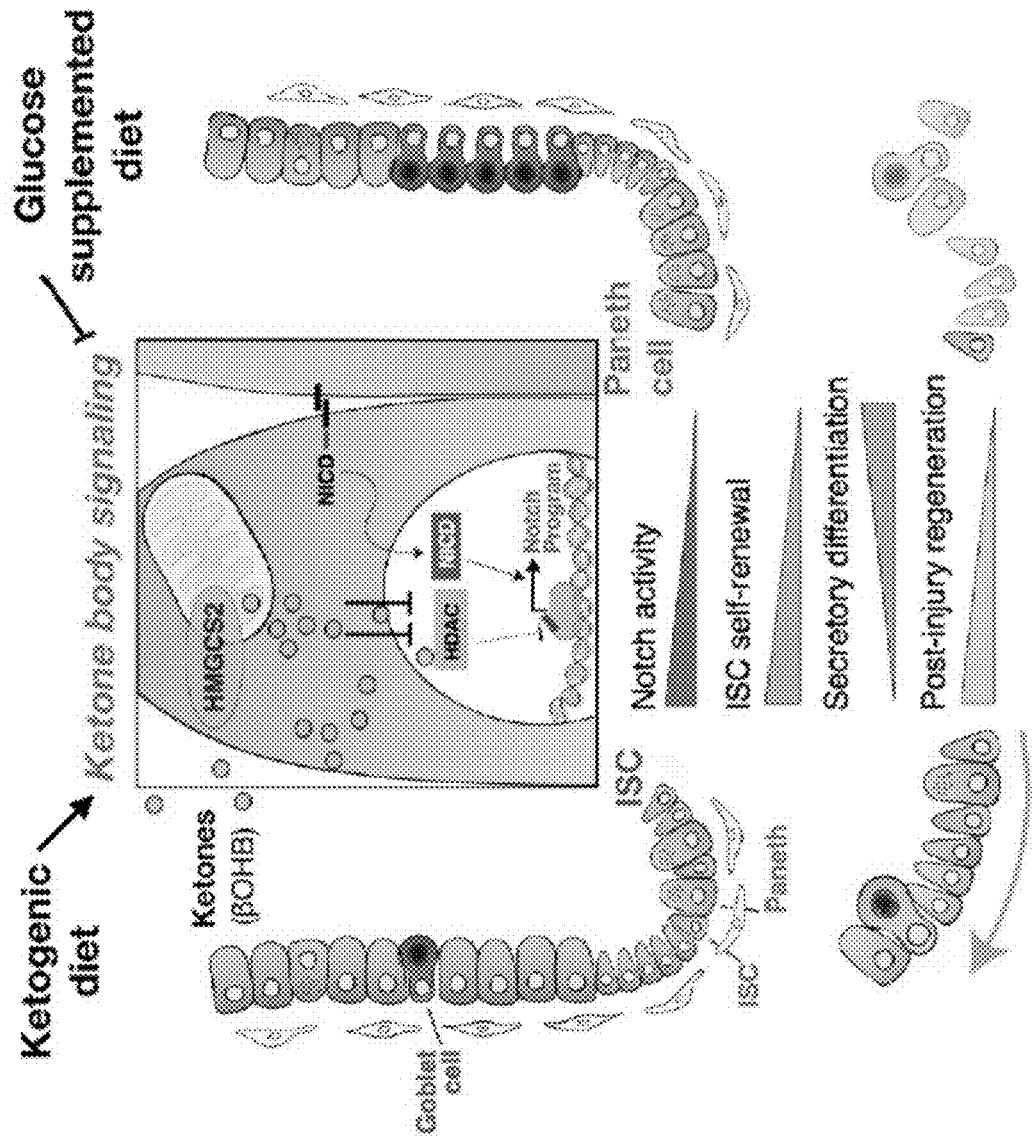
Figure 12D:
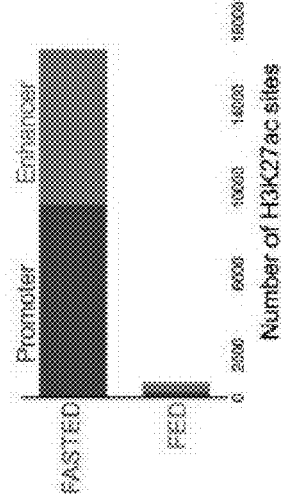
Figure 12G:
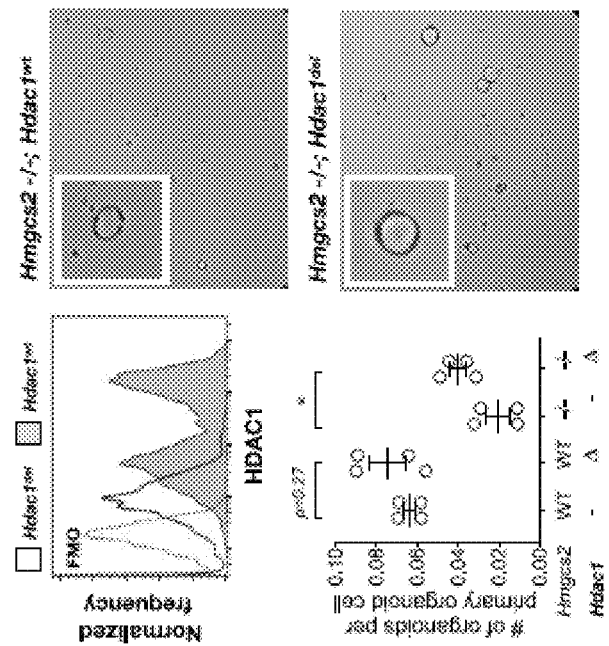
Figure 12F:
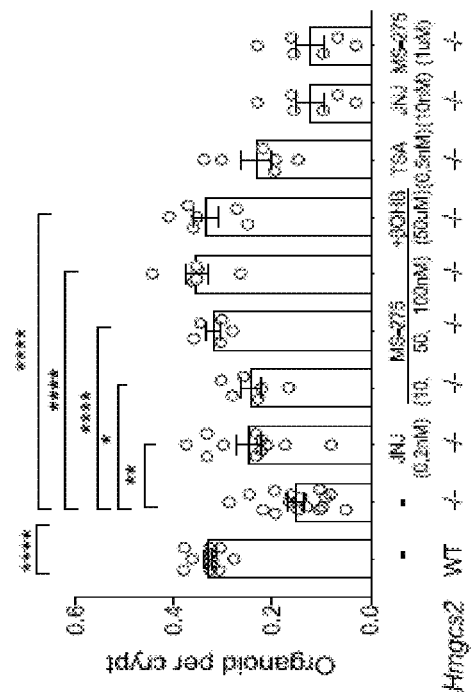

Next, Hmgcs2-null organoids were treated with βOHB, HDAC inhibitors or both and assessed the role of NOTCH in this process by treating a subset of cultures with GSI. Strikingly, it was found that HDAC inhibitor Quisinostat (JNJ-26481585, JNJ) at a dose shown to block HDAC1 activity (Arts et al., 2009), as did CRISPR deletion of HDAC1 (FIGS. 5C and 12G), rescued crypt organoid-forming capacity better than the more promiscuous pan-HDAC class I and II inhibitor trichostatin A (TSA) (FIGS. 5C and 12F). Also, co-treatment of Quisinostat (JNJ) with βOHB did not further augment crypt organoid-forming capacity, demonstrating redundancy between βOHB signaling and HDAC inhibition (FIG. 5C, left). Blockade of NOTCH signaling by GSI treatment prevented the ability of either βOHB or JNJ HDAC inhibitor (FIG. 5C, right) to restore the organoid-forming capacity of Hmgcs2-null crypts, indicating that βOHB and HDAC inhibition regulate ISC function through NICD-mediated transcriptional activity (FIG. 7F). In parallel experiments, treatment with HDAC1/3 inhibitor (MS-275, 10-to-100 nM) rescued Hmgcs2-null organoid function, however, doses beyond this range (Zimberlin et al., 2015) failed to do so (FIG. 12F).

Figure 5F:
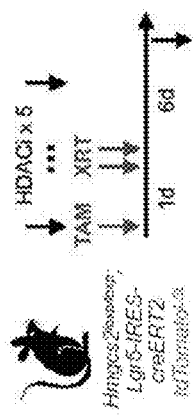
Figure 5G:
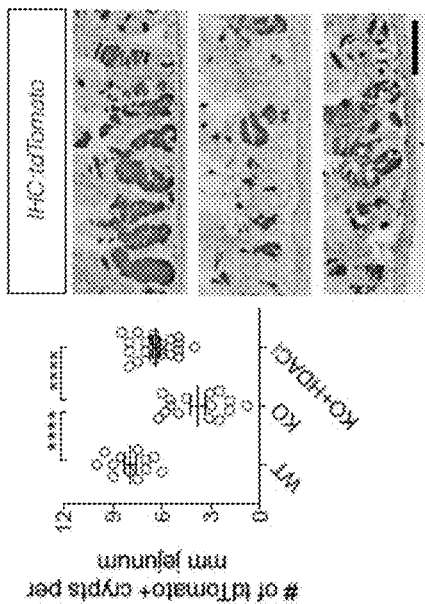
Figure 5E:
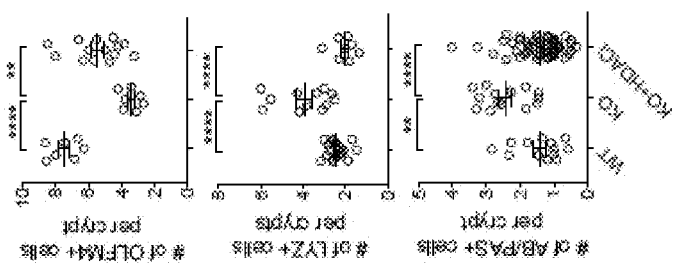
Figure 5D:
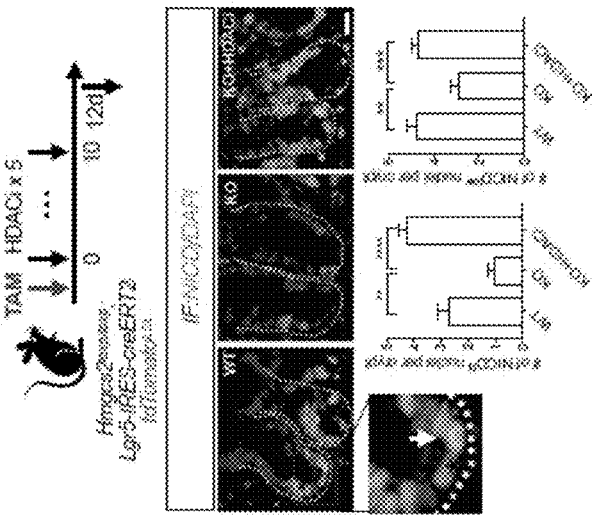
Figure 6B:
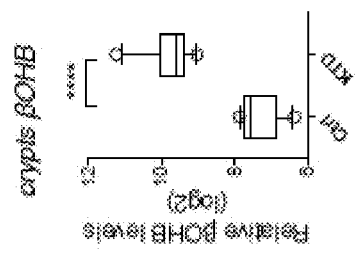
Figure 6C:
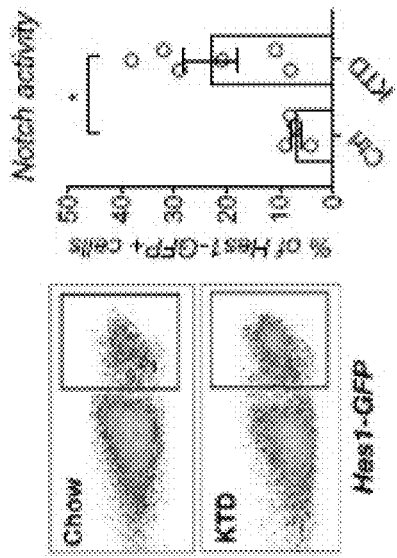
Figure 6A:
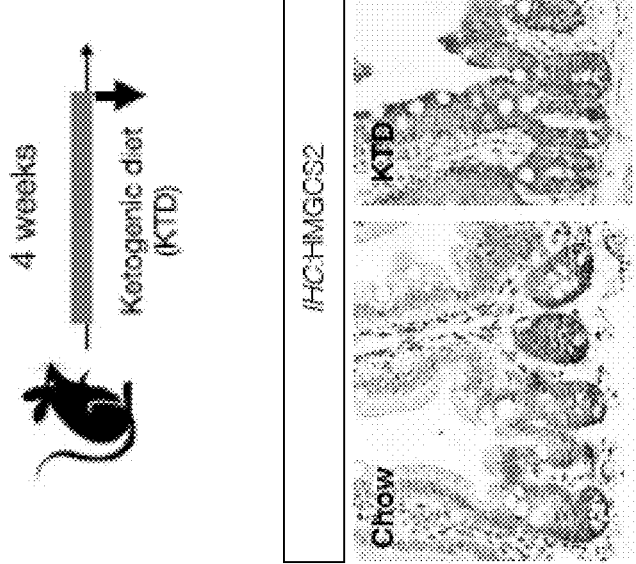
Figures 6G, 6H:
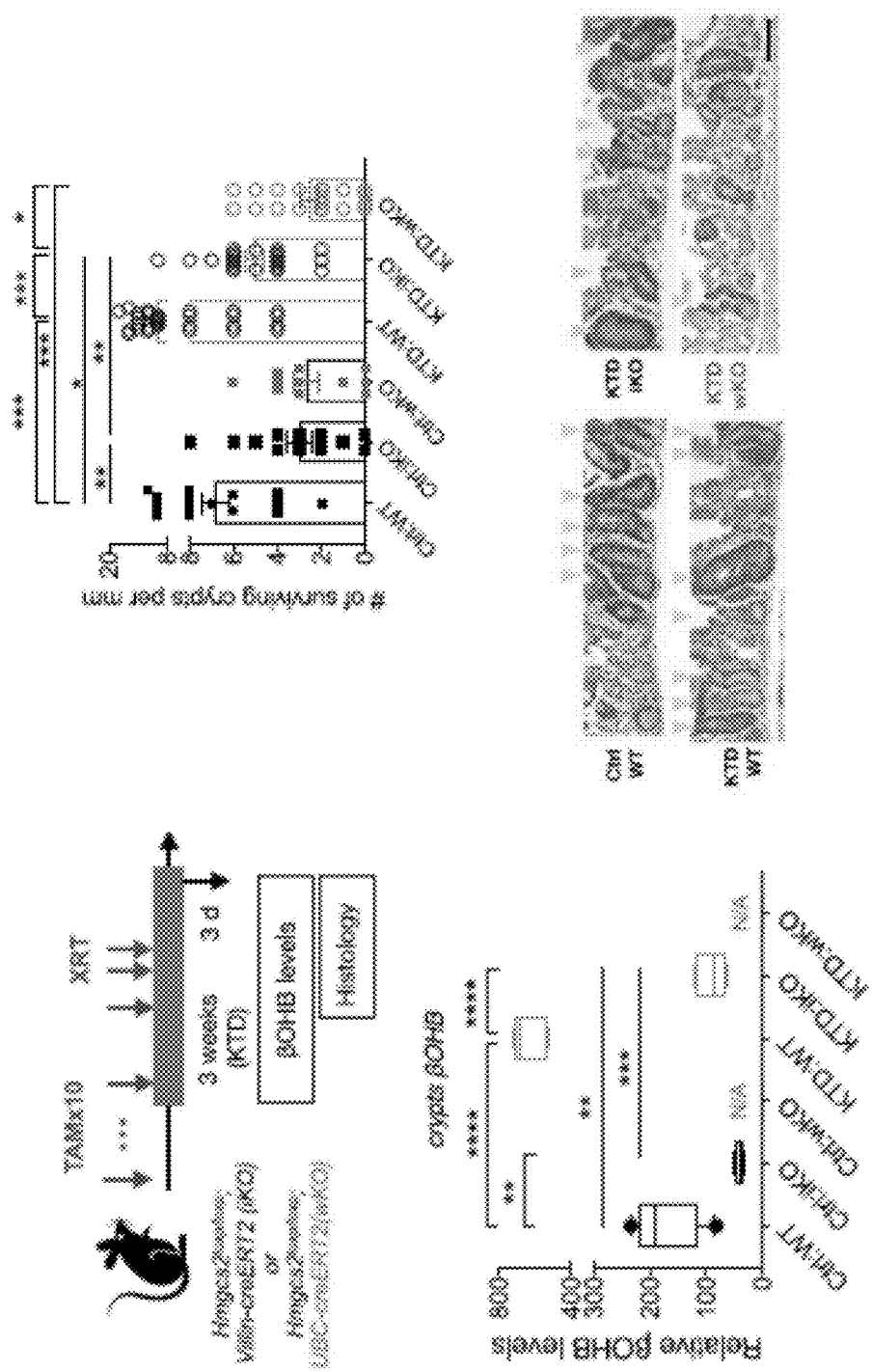
Figure 12H:
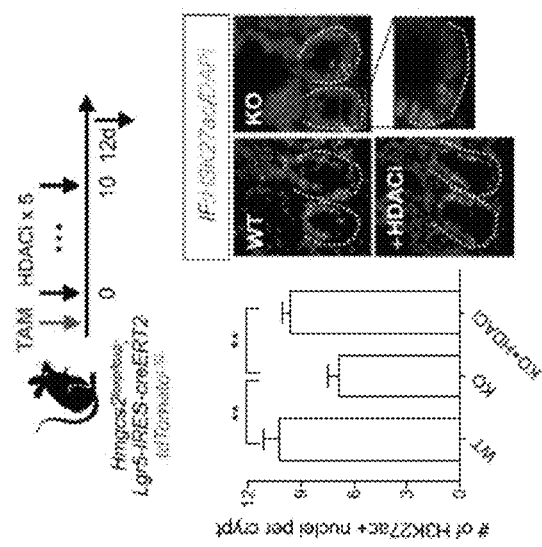
Figure 12I:
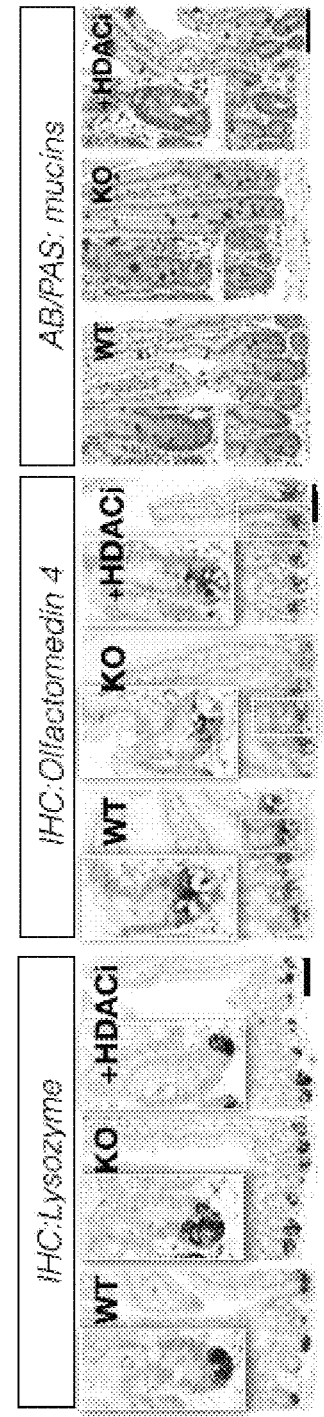

To bolster the connection between HMGCS2-mediated control of HDAC activity and NOTCH signaling in vivo, it was found that Hmgcs2-loss and ketone depletion (FIG. 4D) decreased the numbers of H3K27ac or NICD positive crypt cell nuclei, which correlates with greater HDAC activity and less NOTCH signaling (FIGS. 5D and 12H). Consistent with the paradigm that βOHB hinders HDAC1 activity, robust in vivo induction of Hmgcs2 (Mihaylova et al., 2018; Tinkum et al., 2015) and βOHB levels in the crypts with a 24 hour fast (FIG. 12B) associated with greater H3K27ac enrichment peaks compared to controls by ChIP-seq (FIG. 12C). Moreover, this trend also holds true at gene enhancer and promoter sites (−/+5 kbTSS), including at Hes1 (FIGS. 12D and 12E). Importantly, HDAC inhibitor treatment (JNJ, 1 mg/kg, 5 i.p. injections) of Hmgcs2-null mice not only prevented these changes, but also rescued the decline in ISCs numbers (FIG. 5E), ISC function after injury (FIGS. 5F and G) and the expansion of secretory cell types (FIG. 5E and FIG. 12G). These data collectively support the notion that βOHB drives the downstream effects of HMGCS2 through the inhibition of class I HDACs to stimulate NOTCH signaling for stemness (FIG. 6H).

Example 6

Ketogenic Diet Boosts ISCs Numbers and Function

Because HMGCS2-derived ketones in ISCs promote self-renewal and prevent premature differentiation, it was asked whether a ketogenic diet (KTD, Methods), an intervention that dramatically elevates circulating ketone body levels (Newman et al., 2017), enhances ISC numbers, function, or both. Lgr5$^+$ reporter mice fed a KTD for 4-6 weeks show no change in body mass, intestinal length or crypt depths and have a 3.5-fold increase in plasma βOHB level compared to chow controls (FIGS. 6A and 13A-13D). In the intestine, a KTD pronouncedly not only boosted HMGCS2 protein expression throughout the entire crypt/villous unit (FIG. 6A) that correlated with a 6.8-fold elevation in crypt βOHB concentrations (FIG. 6B) but also enhanced NOTCH activity by 2-fold as measured flow cytometrically for HES1-GFP positivity (FIG. 6C), NICD nuclear localization (FIG. 13F), and OLFM4 protein expression (a NOTCH target gene, FIG. 13E) (Tian et al., 2015; VanDussen et al., 2012). In addition, KTD mice had greater numbers of Lgr5-GFP$^{hi}$/OLFM4$^+$ ISCs and Lgr5-GFP$^{low}$ progenitors (FIGS. 6D and 13E) with higher rates of proliferation for ISCs, but not for progenitor cells, as determined after a 4-hour BrdU pulse (FIG. 13H).

Figure 13F:
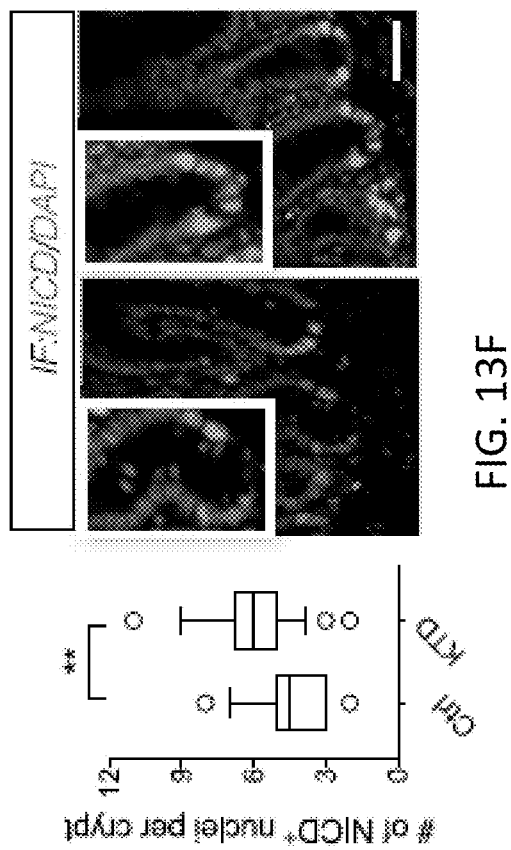
Figure 13G:
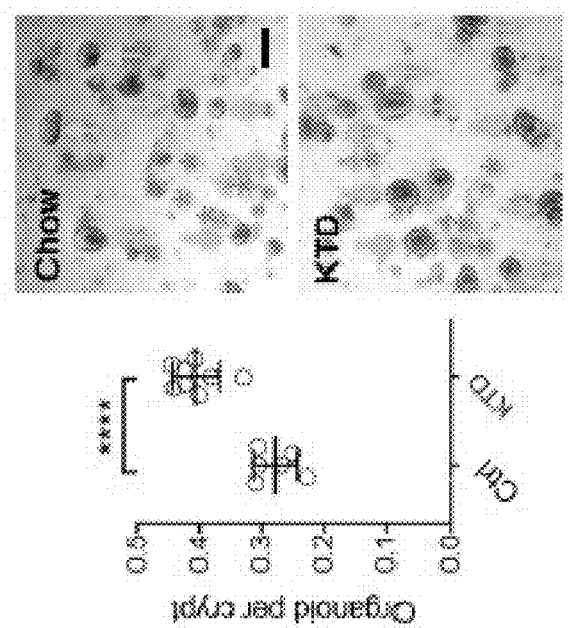
Figure 13L:
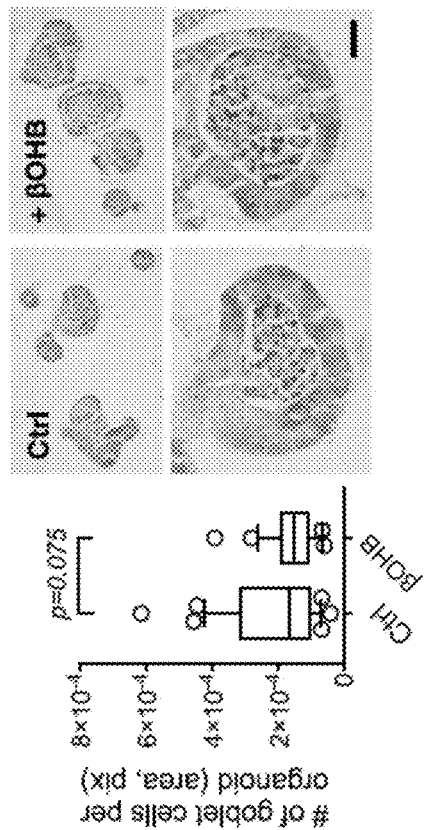
Figure 13K:
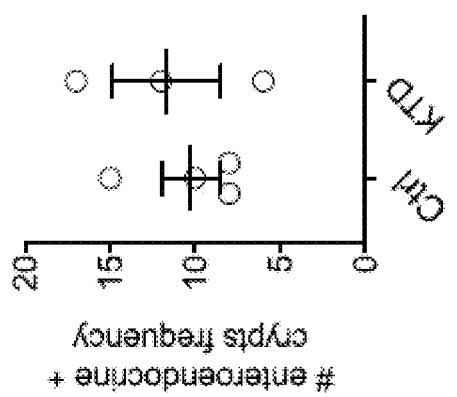

Not only did a KTD lead to quantitative changes in ISCs, both KTD crypts and KTD-derived ISCs in Paneth cell co-culture assays were more capable of forming organoids compared to controls (FIGS. 6E and 13F). Similarly, a KTD also boosted the regenerative output of tdTomato-labeled ISCs after radiation-induced damage relative to their chow counterparts (FIG. 4F). Since exogenous ketones rectify Hmgcs2 loss in vitro (FIG. 11L) and in vivo (FIG. 4F), liver or other non-intestinal sources of ketones may substitute for or supplement ISC-generated ketones in KTD-mediated regeneration (FIG. 4F) where plasma ketone levels are highly elevated (FIG. 13B). To distinguish between the contribution of plasma ketones versus intestinal ketones in this process, Hmgcs2$^{loxp/loxp}$; UBC-CreERT2 conditional whole-body knockout mice were engineered that disrupt Hmgcs2 in all adult cell types upon tamoxifen administration (FIG. 6G, termed wKO). Although Hmgcs2 loss in the iKO model significantly lowered crypt βOHB levels in a KTD, it was still higher than levels noted in control iKO crypts. This difference is likely due to uptake of circulating plasma ketones induced by the KTD (FIG. 6G) as crypt βOHB levels were undetectable in control or KTD crypts from wKO mice (FIG. 6G). Remarkably, this pattern of crypt βOHB concentration mirrored the numbers of intact surviving crypts after radiation-induced intestinal epithelial injury (FIG. 6H). While the pro-regenerative effects of a KTD were blunted by intestinal Hmgcs2 loss, they were entirely blocked with whole body Hmgcs2 loss, demonstrating that βOHB regulates ISCs in a cell autonomous and non-autonomous manner in ketogenic states (FIG. 6H).

Figure 13M:
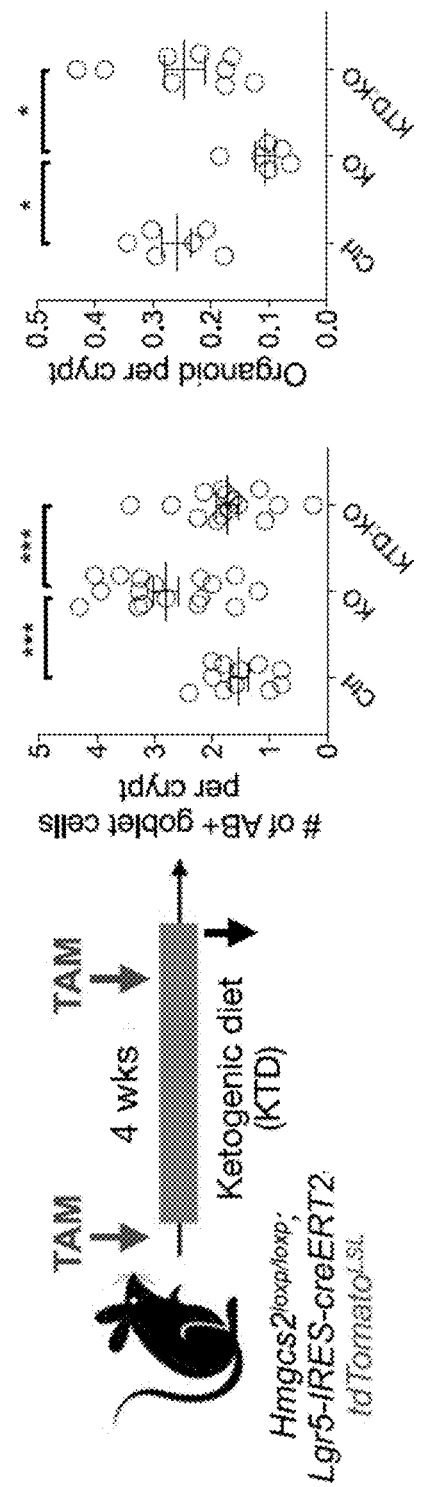

Although exogenous βOHB in a KTD restored the in vivo lineage differentiation defects and crypt organoid-forming capacity in Hmgcs2-null intestines (FIG. 13M), neither a KTD nor exogenous βOHB exposure in wild-type intestines or organoids impacted secretory cell lineage differentiation (FIGS. 13G to 13J). This finding indicates that while surplus intestinal βOHB bolsters ISC self-renewal (i.e. ISC numbers, proliferation, and in vitro and in vivo function) and NOTCH signaling, it is not sufficient to suppress secretory differentiation in Hmgcs2-compentent ISCs. This disconnect between excessive (i.e. supraphysiologic) NOTCH activity in driving stemness but not in inhibiting secretory differentiation has been previously documented in conditional genetic models of enforced NOTCH signaling in the adult intestine (Vooijs et al., 2011; Zecchini et al., 2005).

Example 7

A Glucose-Supplemented Diet Dampens Intestinal Ketogenesis and Stemness

Figure 14B:
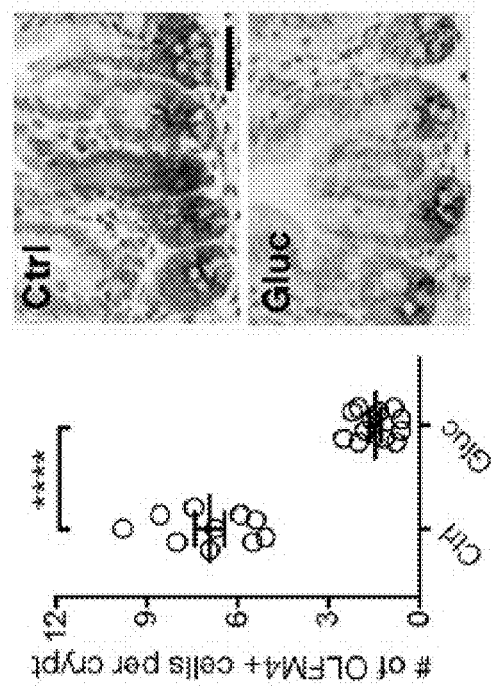
FIGS. 14A-14D. Characterization of the effects of a glucose supplemented diet on ISC and organoids. Related to FIG. 7.
Figure 14A:
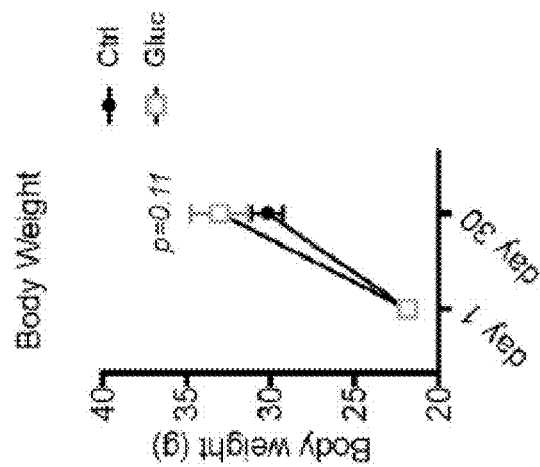
Figure 14C:
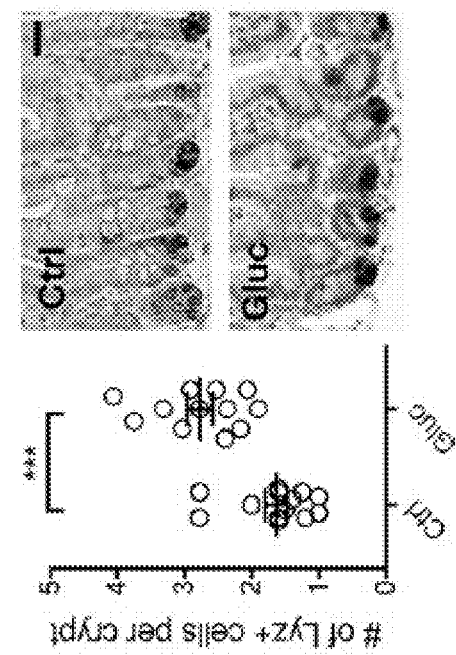
Figure 14D:
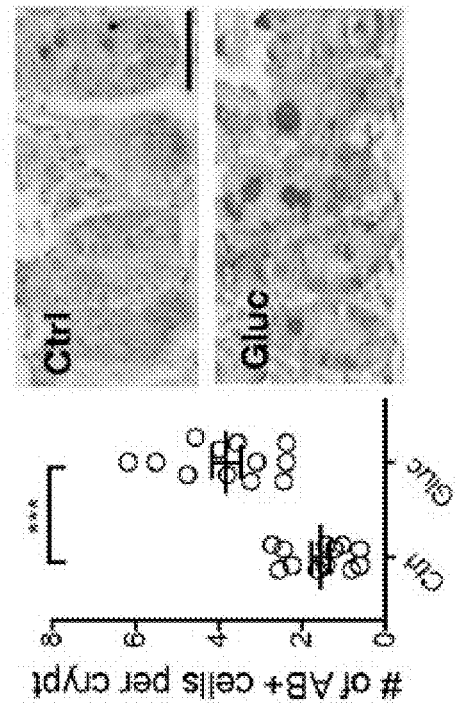

Ketogenesis is an adaptive response to dietary shortages of carbohydrates, where in low carbohydrate states liver-derived ketone bodies are utilized by peripheral tissues for energy (Newman and Verdin, 2017; Puchalska and Crawford, 2017). In the presence of dietary glucose, for example, hepatic HMGCS2 expression and ketone body production rapidly switch off in response to insulin (Cotter et al., 2013). To investigate how a glucose-supplemented diet alters ISCs, mice were fed a chow diet with glucose supplemented drinking water (13% glucose in drinking water, ad libitum) for 4 weeks (FIG. 7A), where mice consumed 2.68+/−0.5 ml of the glucose solution (per mouse per day). While 4-week glucose supplementation did not induce obesity (FIG. 14A), this regimen significantly diminished HMGCS2 expression at the crypt base (FIG. 7A) and reduced crypt βOHB levels (FIG. 7B). This dietary suppression of intestinal ketogenesis was accompanied by a 2-fold decrease in Hes1 expression, confirming that NOTCH activity correlates with βOHB concentrations (FIG. 7C). Similar to intestinal Hmgcs2 loss (FIG. 2), mice on this regimen had 3-fold fewer OLFM4+ ISCs and greater Lyz1+ Paneth cell and AB+ goblet cell numbers (FIGS. 14B-14D). Functionally, a 2-week course of glucose supplementation hampered the ability of ISCs by 2-fold to generate tdTomato$^+$ labeled progeny in lineage tracing experiment with radiation-induced injury (FIG. 7D) and separately decreased surviving intact crypt numbers compared to controls (FIG. 7E). These functional deficits could be rescued by a single oral bolus of βOHB (15 mg/25 g βOHB oligomers, 16 hrs prior to irradiation) (FIGS. 7D and 7E). These results illustrate that dietary suppression of βOHB production mimics many aspects of Hmgcs2 loss and that exogenous ketone bodies can compensate for these deficits.

The data described herein presents a model in which small intestinal Lgr5$^+$ ISCs express the enzyme 3-hydroxy-3-Methylglutaryl-CoA Synthase 2 (i.e., HMGCS2) that produces ketone bodies including acetoacetate, acetate, and β-hydroxybutyrate (βOHB) to regulate intestinal stemness (FIG. 6H). In the present disclosure, novel roles were identified for βOHB as a signaling metabolite in Lgr5$^+$ ISCs that facilitates NOTCH signaling—a developmental pathway that regulates stemness and differentiation in the intestine—through HDAC inhibition (FIG. 7F). Thus, dynamic control of βOHB levels in ISCs enables this metabolic messenger to execute rapid intestinal remodeling in response to diverse physiological states (FIG. 7F).

Figure 3J:
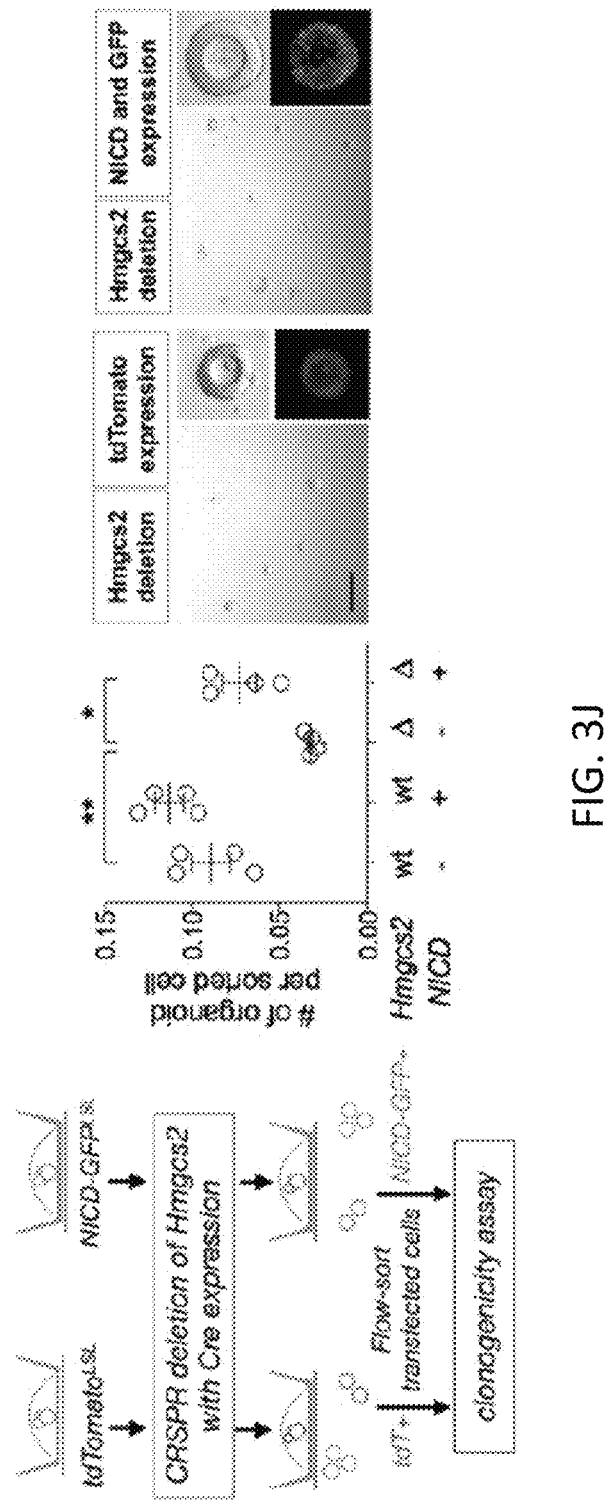

Many lines of evidence indicate that NOTCH signaling is undergirding the effects of HMGCS2 in Lgr5$^+$ ISCs: First, Hmgcs2 loss leads to a gradual decrease in the expression and number of OLFM4$^+$ cells within the crypt (FIG. 2D), which is a stem-cell marker dependent on NOTCH signaling (VanDussen et al., 2012). Second, Hmgcs2 loss emulates many of the characteristics of intestinal-specific Notch1 deletion with expansions in goblet and Paneth cell populations (FIGS. 2E, 2F, 9G, and 3A-3H) (Fre et al., 2005; Kim et al., 2014; Sancho et al., 2015; Yang et al., 2001). Third, Hmgcs2 loss dampens NOTCH target gene expression, perturbs NOTCH-mediated lateral inhibition (FIGS. 3H and 3I) and primes ISCs to adopt an early Paneth cell fate (FIGS. 3F, 3G, 10G and 10H). Lastly, these deficits correlate with a reduction in the number of NICD positive intestinal crypt cell nuclei (FIG. 5D) and constitutive NOTCH activity remedies Hmgcs2-null organoid function (FIG. 3J).

Figure 10G:
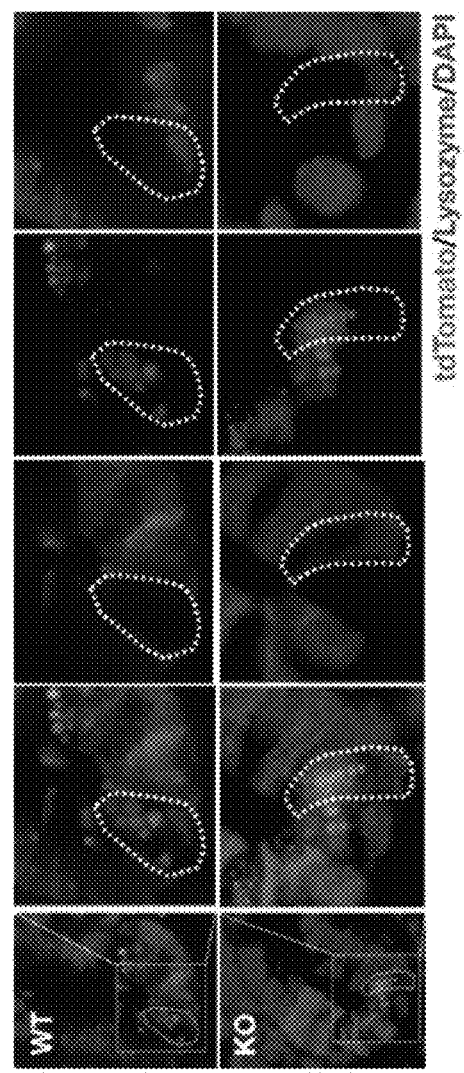
Figure 10H:
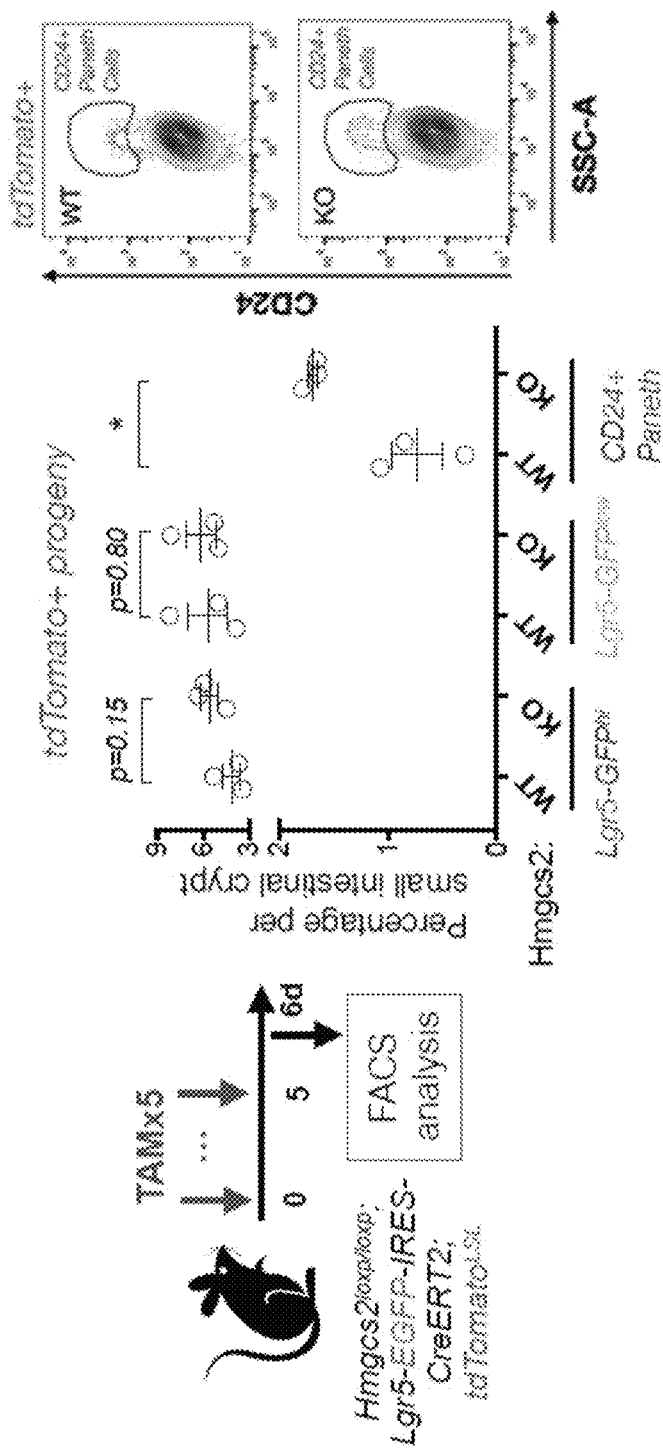

As Lgr5$^+$ ISCs receive NOTCH ligand stimulation (e.g. Dll1 and Dll4) from their Paneth cell niche, an important question is why do small intestinal Lgr5$^+$ ISCs reinforce NOTCH signaling with endogenous ketones? One answer is that stem cells, in contrast to lateral NOTCH inhibition in non-ISC progenitor cells that are higher up in the crypt, depend on greater NOTCH activity to maintain stemness and prevent their premature differentiation into Paneth cells (FIGS. 3G and 10G). These redundant pathways that stimulate NOTCH signaling in Lgr5$^+$ ISCs may, for example, permit these cells to persist when Paneth cells are depleted with diphtheria toxic (Sato et al., 2011) or in other genetic models (Durand et al., 2012; Kim et al., 2012a; Yang et al., 2001) such as with intestinal Atoh1-loss (FIGS. 4C, 11E and 11F).

Figure 9G:
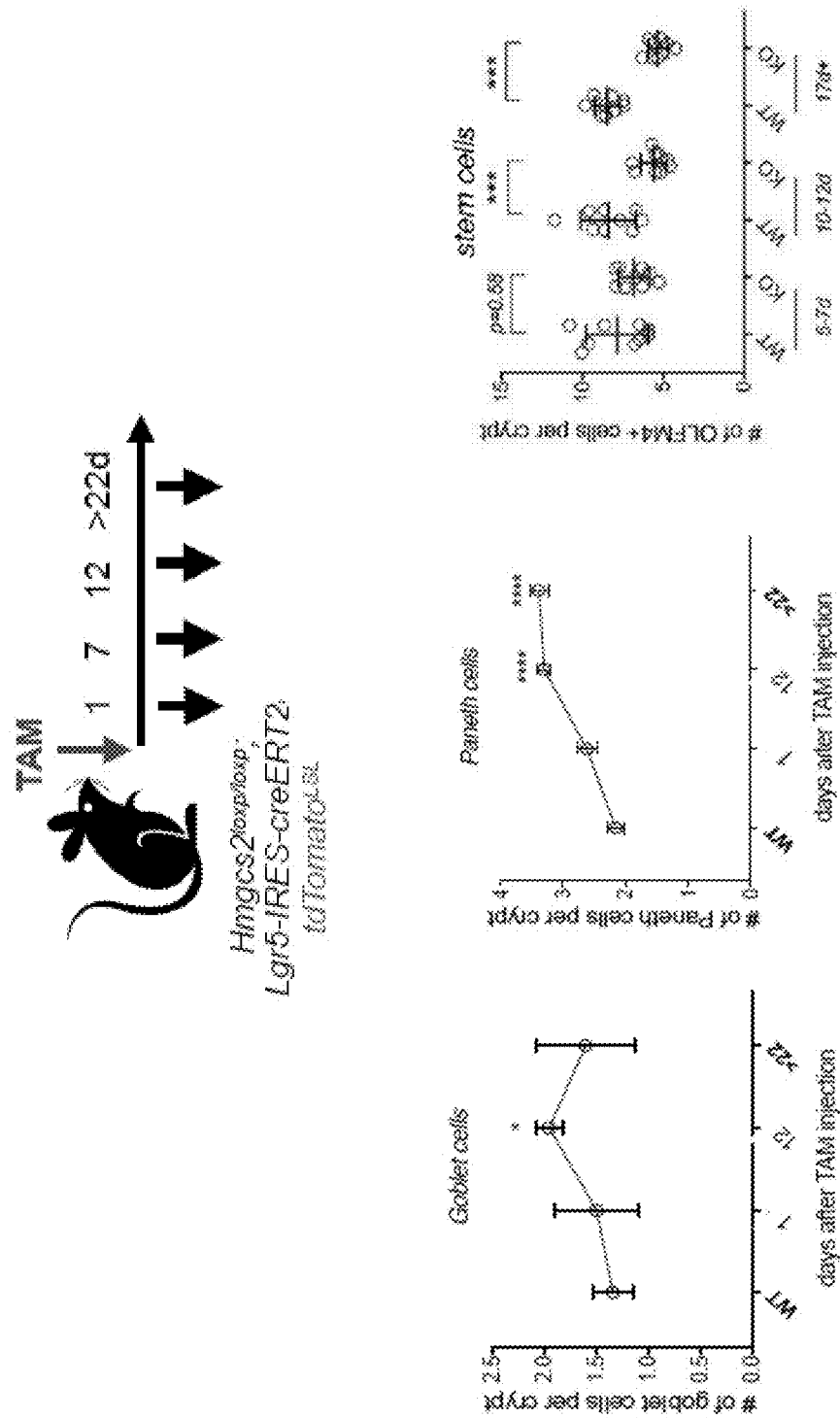

Another possibility is that systemic and intestinal βOHB production provides a signaling circuit that couples organismal diet and metabolism to intestinal adaptation (Barish et al., 2006; Beyaz et al., 2016; Ito et al., 2012; Narkar et al., 2008). For example, it was previously reported that diets that induce ketogenic states such as fasting (Mihaylova et al., 2018), high fat diets (Beyaz et al., 2016) and ketogenic diets (FIGS. 6 and 7E) strongly induce PPAR (Peroxisome Proliferator-activated Receptor) transcriptional targets in ISCs that also includes Hmgcs2 (FIG. 9E). Furthermore, these ketogenic states coordinately drive βOHB production in the liver (which accounts for plasma levels) and in the intestine, which both then stimulate a ketone body-mediated signaling cascade in stem cells that bolsters intestinal regeneration after injury (FIGS. 9F-H). The present disclosure shows that βOHB actuates the ISC-enhancing effects of these ketone-generating diets by functioning downstream of PPAR-delta signaling to reinforce NOTCH activity. Supporting this supposition, it was found that a ketogenic diet boosts not only crypt βOHB levels but also ISC numbers, function and NOTCH signaling. The converse occurs in glucose rich diets where βOHB levels are suppressed as are ISC numbers, function and NOTCH signaling. An interesting implication of this disclosure is to understand the cancer implications of ISC-promoting ketogenic diets, given that some intestinal cancers arise from ISCs (Barker et al., 2009) and that ketogenic diets in some mouse strains improve health and mid-life survival (Newman et al., 2017).

REFERENCES

Adijanto, J., Du, J., Moffat, C., Seifert, E. L., Hurle, J. B., and Philp, N. J. (2014). The retinal pigment epithelium utilizes fatty acids for ketogenesis. The Journal of biological chemistry 289, 20570-20582.

Agathocleous, M., Meacham, C. E., Burgess, R. J., Piskounova, E., Zhao, Z., Crane, G. M., Cowin, B. L., Bruner, E., Murphy, M. M., Chen, W., et al. (2017). Ascorbate regulates haematopoietic stem cell function and leukaemogenesis. Nature 549, 476-481.

Arts, J., King, P., Marien, A., Floren, W., Belien, A., Janssen, L., Pilatte, I., Roux, B., Decrane, L., Gilissen, R., et al. (2009). JNJ-26481585, a novel "second-generation" oral histone deacetylase inhibitor, shows broad-spectrum preclinical antitumoral activity. Clin Cancer Res 15, 6841-6851.

Barish, G. D., Narkar, V. A., and Evans, R. M. (2006). PPAR delta: a dagger in the heart of the metabolic syndrome. The Journal of clinical investigation 116, 590-597.

Barker, N., Ridgway, R. A., van Es, J. H., van de Wetering, M., Begthel, H., van den Born, M., Danenberg, E., Clarke, A. R., Sansom, O. J., and Clevers, H. (2009). Crypt stem cells as the cells-of-origin of intestinal cancer. Nature 457, 608-611.

Barker, N., van Es, J. H., Kuipers, J., Kujala, P., van den Born, M., Cozijnsen, M., Haegebarth, A., Korving, J., Begthel, H., Peters, P. J., et al. (2007). Identification of stem cells in small intestine and colon by marker gene Lgr5. Nature 449, 1003-1007.

Beumer, J., and Clevers, H. (2016). Regulation and plasticity of intestinal stem cells during homeostasis and regeneration. Development 143, 3639-3649.

Beyaz, S., Mana, M. D., Roper, J., Kedrin, D., Saadatpour, A., Hong, S. J., Bauer-Rowe, K. E., Xifaras, M. E., Akkad, A., Arias, E., et al. (2016). High-fat diet enhances stemness and tumorigenicity of intestinal progenitors. Nature 531, 53-58.

Biton, M., Haber, A. L., Rogel, N., Burgin, G., Beyaz, S., Schnell, A., Ashenberg, O., Su, C. W., Smillie, C., Shekhar, K., et al. (2018). T Helper Cell Cytokines Modulate Intestinal Stem Cell Renewal and Differentiation. Cell 175, 1307-1320 e1322.

Blecher-Gonen, R., Barnett-Itzhaki, Z., Jaitin, D., Amann-Zalcenstein, D., Lara-Astiaso, D., and Amit, I. (2013). High-throughput chromatin immunoprecipitation for genome-wide mapping of in vivo protein-DNA interactions and epigenomic states. Nat Protoc 8, 539-554.

Cimmino, L., Dolgalev, I., Wang, Y., Yoshimi, A., Martin, G. H., Wang, J., Ng, V., Xia, B., Witkowski, M. T., Mitchell-Flack, M., et al. (2017). Restoration of TET2 Function Blocks Aberrant Self-Renewal and Leukemia Progression. Cell 170, 1079-1095 e1020.

Cotter, D. G., Schugar, R. C., and Crawford, P. A. (2013). Ketone body metabolism and cardiovascular disease. Am J Physiol Heart Circ Physiol 304, H1060-1076.

de la Cruz Bonilla, M., Stemler, K. M., Taniguchi, C. M., and Piwnica-Worms, H. (2018). Stem cell enriched-epithelial spheroid cultures for rapidly assaying small intestinal radioprotectors and radiosensitizers in vitro. Scientific reports 8, 15410.

Degirmenci, B., Valenta, T., Dimitrieva, S., Hausmann, G., and Basler, K. (2018). GLI1-expressing mesenchymal cells form the essential Wnt-secreting niche for colon stem cells. Nature 558, 449-453.

Dixit, A., Parnas, O., Li, B., Chen, J., Fulco, C. P., Jerby-Arnon, L., Marjanovic, N. D., Dionne, D., Burks, T., Raychowdhury, R., et al. (2016). Perturb-Seq: Dissecting Molecular Circuits with Scalable Single-Cell RNA Profiling of Pooled Genetic Screens. Cell 167, 1853-1866 e1817.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Durand, A., Donahue, B., Peignon, G., Letourneur, F., Cagnard, N., Slomianny, C., Perret, C., Shroyer, N. F., and Romagnolo, B. (2012). Functional intestinal stem cells after Paneth cell ablation induced by the loss of transcription factor Math1 (Atoh1). Proceedings of the National Academy of Sciences of the United States of America 109, 8965-8970.

el Marjou, F., Janssen, K. P., Chang, B. H., Li, M., Hindie, V., Chan, L., Louvard, D., Chambon, P., Metzger, D., and Robine, S. (2004). Tissue-specific and inducible Cre-mediated recombination in the gut epithelium. Genesis 39, 186-193.

Faust, G. G., and Hall, I. M. (2014). SAMBLASTER: fast duplicate marking and structural variant read extraction. Bioinformatics 30, 2503-2505.

Finak, G., McDavid, A., Yajima, M., Deng, J., Gersuk, V., Shalek, A. K., Slichter, C. K., Miller, H. W., McElrath, M. J., Prlic, M., et al. (2015). MAST: a flexible statistical framework for assessing transcriptional changes and characterizing heterogeneity in single-cell RNA sequencing data. Genome biology 16, 278.

Fre, S., Huyghe, M., Mourikis, P., Robine, S., Louvard, D., and Artavanis-Tsakonas, S. (2005). Notch signals control the fate of immature progenitor cells in the intestine. Nature 435, 964-968.

Garber, M., Yosef, N., Goren, A., Raychowdhury, R., Thielke, A., Guttman, M., Robinson, J., Minie, B., Chevrier, N., Itzhaki, Z., et al. (2012). A high-throughput chromatin immunoprecipitation approach reveals principles of dynamic gene regulation in mammals. Mol Cell 47, 810-822.

Gonneaud, A., Turgeon, N., Boisvert, F. M., Boudreau, F., and Asselin, C. (2015). Loss of histone deacetylase Hdac1 disrupts metabolic processes in intestinal epithelial cells. FEBS Lett 589, 2776-2783.

Guo, J., Longshore, S., Nair, R., and Warner, B. W. (2009). Retinoblastoma protein (pRb), but not p107 or p130, is required for maintenance of enterocyte quiescence and differentiation in small intestine. J Biol Chem 284, 134-140.

Haber, A. L., Biton, M., Rogel, N., Herbst, R. H., Shekhar, K., Smillie, C., Burgin, G., Delorey, T. M., Howitt, M. R., Katz, Y., et al. (2017). A single-cell survey of the small intestinal epithelium. Nature 551, 333-339.

Haberland, M., Montgomery, R. L., and Olson, E. N. (2009). The many roles of histone deacetylases in development and physiology: implications for disease and therapy. Nature reviews Genetics 10, 32-42.

Hsieh, J. J., Zhou, S., Chen, L., Young, D. B., and Hayward, S. D. (1999). CIR, a corepressor linking the DNA binding factor CBF1 to the histone deacetylase complex. Proceedings of the National Academy of Sciences of the United States of America 96, 23-28.

Huch, M., Dorrell, C., Boj, S. F., van Es, J. H., Li, V. S., van de Wetering, M., Sato, T., Hamer, K., Sasaki, N., Finegold, M. J., et al. (2013). In vitro expansion of single Lgr5+ liver stem cells induced by Wnt-driven regeneration. Nature 494, 247-250.

Igarashi, M., and Guarente, L. (2016). mTORC1 and SIRT1 Cooperate to Foster Expansion of Gut Adult Stem Cells during Calorie Restriction. Cell 166, 436-450.

Ito, K., Carracedo, A., Weiss, D., Arai, F., Ala, U., Avigan, D. E., Schafer, Z. T., Evans, R. M., Suda, T., Lee, C. H., et al. (2012). A PML-PPAR-delta pathway for fatty acid oxidation regulates hematopoietic stem cell maintenance. Nature medicine 18, 1350-1358.

Johnson, W. E., Li, C., and Rabinovic, A. (2007). Adjusting batch effects in microarray expression data using empirical Bayes methods. Biostatistics 8, 118-127.

Kao, H. Y., Ordentlich, P., Koyano-Nakagawa, N., Tang, Z., Downes, M., Kintner, C. R., Evans, R. M., and Kadesch, T. (1998). A histone deacetylase corepressor complex regulates the Notch signal transduction pathway. Genes Dev 12, 2269-2277.

Kim, T. H., Escudero, S., and Shivdasani, R. A. (2012a). Intact function of Lgr5 receptor-expressing intestinal stem cells in the absence of Paneth cells. Proceedings of the National Academy of Sciences of the United States of America 109, 3932-3937.

Kim, T. H., Escudero, S., and Shivdasani, R. A. (2012b). Intact function of Lgr5 receptor-expressing intestinal stem cells in the absence of Paneth cells. Proceedings of the National Academy of Sciences of the United States of America 109, 3932-3937.

Kim, T. H., Li, F., Ferreiro-Neira, I., Ho, L. L., Luyten, A., Nalapareddy, K., Long, H., Verzi, M., and Shivdasani, R. A. (2014). Broadly permissive intestinal chromatin underlies lateral inhibition and cell plasticity. Nature 506, 511-515.

Kim, T. H., Saadatpour, A., Guo, G., Saxena, M., Cavazza, A., Desai, N., Jadhav, U., Jiang, L., Rivera, M. N., Orkin, S. H., et al. (2016). Single-Cell Transcript Profiles Reveal Multilineage Priming in Early Progenitors Derived from Lgr5(+) Intestinal Stem Cells. Cell reports 16, 2053-2060.

Kowalczyk, M. S., Tirosh, I., Heckl, D., Rao, T. N., Dixit, A., Haas, B. J., Schneider, R. K., Wagers, A. J., Ebert, B. L., and Regev, A. (2015). Single-cell RNA-seq reveals changes in cell cycle and differentiation programs upon aging of hematopoietic stem cells. Genome research 25, 1860-1872.

Langmead, B., Trapnell, C., Pop, M., and Salzberg, S. L. (2009). Ultrafast and memory-efficient alignment of short DNA sequences to the human genome. Genome biology 10, R25.

Leek, J. T., Johnson, W. E., Parker, H. S., Jaffe, A. E., and Storey, J. D. (2012). The sva package for removing batch effects and other unwanted variation in high-throughput experiments. Bioinformatics 28, 882-883.

Li, B., and Dewey, C. N. (2011). RSEM: accurate transcript quantification from RNA-Seq data with or without a reference genome. BMC Bioinformatics 12, 323.

Li, J., Ng, E. K., Ng, Y. P., Wong, C. Y., Yu, J., Jin, H., Cheng, V. Y., Go, M. Y., Cheung, P. K., Ebert, M. P., et al. (2009). Identification of retinoic acid-regulated nuclear matrix-associated protein as a novel regulator of gastric cancer. Br J Cancer 101, 691-698.

Lim, J. S., Ibaseta, A., Fischer, M. M., Cancilla, B., O'Young, G., Cristea, S., Luca, V. C., Yang, D., Jahchan, N. S., Hamard, C., et al. (2017). Intratumoural heterogeneity generated by Notch signalling promotes small-cell lung cancer. Nature 545, 360-364.

Lindemans, C. A., Calafiore, M., Mertelsmann, A. M., O'Connor, M. H., Dudakov, J. A., Jenq, R. R., Velardi, E., Young, L. F., Smith, O. M., Lawrence, G., et al. (2015). Interleukin-22 promotes intestinal-stem-cell-mediated epithelial regeneration. Nature 528, 560-564.

Liu, T., Ortiz, J. A., Taing, L., Meyer, C. A., Lee, B., Zhang, Y., Shin, H., Wong, S. S., Ma, J., Lei, Y., et al. (2011). Cistrome: an integrative platform for transcriptional regulation studies. Genome Biol 12, R83.

McCarthy, D. J., Chen, Y., and Smyth, G. K. (2012). Differential expression analysis of multifactor RNA-Seq experiments with respect to biological variation. Nucleic acids research 40, 4288-4297.

Metcalfe, C., Kljavin, N. M., Ybarra, R., and de Sauvage, F. J. (2014). Lgr5+ stem cells are indispensable for radiation-induced intestinal regeneration. Cell stem cell 14, 149-159.

Mihaylova, M. M., Cheng, C. W., Cao, A. Q., Tripathi, S., Mana, M. D., Bauer-Rowe, K. E., Abu-Remaileh, M., Clavain, L., Erdemir, A., Lewis, C. A., et al. (2018). Fasting Activates Fatty Acid Oxidation to Enhance Intestinal Stem Cell Function during Homeostasis and Aging. Cell stem cell 22, 769-778 e764.

Mihaylova, M. M., Sabatini, D. M., and Yilmaz, O. H. (2014). Dietary and metabolic control of stem cell function in physiology and cancer. Cell stem cell 14, 292-305.

Munoz, J., Stange, D. E., Schepers, A. G., van de Wetering, M., Koo, B. K., Itzkovitz, S., Volckmann, R., Kung, K. S., Koster, J., Radulescu, S., et al. (2012a). The Lgr5 intestinal stem cell signature: robust expression of proposed quiescent '+4' cell markers. The EMBO journal 31, 3079-3091.

Munoz, J., Stange, D. E., Schepers, A. G., van de Wetering, M., Koo, B. K., Itzkovitz, S., Volckmann, R., Kung, K. S., Koster, J., Radulescu, S., et al. (2012b). The Lgr5 intestinal stem cell signature: robust expression of proposed quiescent '+4' cell markers. The EMBO journal 31, 3079-3091.

Nakada, D., Levi, B. P., and Morrison, S. J. (2011). Integrating physiological regulation with stem cell and tissue homeostasis. Neuron 70, 703-718.

Narkar, V. A., Downes, M., Yu, R. T., Embler, E., Wang, Y. X., Banayo, E., Mihaylova, M. M., Nelson, M. C., Zou, Y., Juguilon, H., et al. (2008). AMPK and PPARdelta agonists are exercise mimetics. Cell 134, 405-415.

Newman, J. C., Covarrubias, A. J., Zhao, M., Yu, X., Gut, P., Ng, C. P., Huang, Y., Haldar, S., and Verdin, E. (2017). Ketogenic Diet Reduces Midlife Mortality and Improves Memory in Aging Mice. Cell metabolism 26, 547-557 e548.

Newman, J. C., and Verdin, E. (2017). β-Hydroxybutyrate: A Signaling Metabolite. Annu Rev Nutr 37, 51-76.

Ootani, A., Li, X., Sangiorgi, E., Ho, Q. T., Ueno, H., Toda, S., Sugihara, H., Fujimoto, K., Weissman, I. L., Capecchi, M. R., et al. (2009). Sustained in vitro intestinal epithelial culture within a Wnt-dependent stem cell niche. Nature medicine 15, 701-706.

Oswald, F., Kostezka, U., Astrahantseff, K., Bourteele, S., Dillinger, K., Zechner, U., Ludwig, L., Wilda, M., Hameister, H., Knochel, W., et al. (2002). SHARP is a novel component of the Notch/RBP-Jkappa signalling pathway. The EMBO journal 21, 5417-5426.

Peregrina, K., Houston, M., Daroqui, C., Dhima, E., Sellers, R. S., and Augenlicht, L. H. (2015). Vitamin D is a determinant of mouse intestinal Lgr5 stem cell functions. Carcinogenesis 36, 25-31.

Puchalska, P., and Crawford, P. A. (2017). Multi-dimensional Roles of Ketone Bodies in Fuel Metabolism, Signaling, and Therapeutics. Cell Metab 25, 262-284.

Qi, Z., Li, Y., Zhao, B., Xu, C., Liu, Y., Li, H., Zhang, B., Wang, X., Yang, X., Xie, W., et al. (2017). BMP restricts stemness of intestinal Lgr5(+) stem cells by directly suppressing their signature genes. Nature communications 8, 13824.

Ramirez, F., Ryan, D. P., Gruning, B., Bhardwaj, V., Kilpert, F., Richter, A. S., Heyne, S., Dundar, F., and Manke, T. (2016). deepTools2: a next generation web server for deep-sequencing data analysis. Nucleic Acids Res 44, W160-165.

Rickelt, S., and Hynes, R. O. (2018). Antibodies and methods for immunohistochemistry of extracellular matrix proteins. Matrix Biol 71-72, 10-27.

Rodriguez-Colman, M. J., Schewe, M., Meerlo, M., Stigter, E., Gerrits, J., Pras-Raves, M., Sacchetti, A., Hornsveld, M., Oost, K. C., Snippert, H. J., et al. (2017). Interplay between metabolic identities in the intestinal crypt supports stem cell function. Nature 543, 424-427.

Rognstad, R. (1979). Rate-limiting steps in metabolic pathways. The Journal of biological chemistry 254, 1875-1878.

Sancho, R., Cremona, C. A., and Behrens, A. (2015). Stem cell and progenitor fate in the mammalian intestine: Notch and lateral inhibition in homeostasis and disease. EMBO Rep 16, 571-581.

Sasaki, N., Sachs, N., Wiebrands, K., Ellenbroek, S. I., Fumagalli, A., Lyubimova, A., Begthel, H., van den Born, M., van Es, J. H., Karthaus, W. R., et al. (2016). Reg4+ deep crypt secretory cells function as epithelial niche for Lgr5+ stem cells in colon. Proceedings of the National Academy of Sciences of the United States of America 113, E5399-5407.

Sato, T., van Es, J. H., Snippert, H. J., Stange, D. E., Vries, R. G., van den Born, M., Barker, N., Shroyer, N. F., van de Wetering, M., and Clevers, H. (2011). Paneth cells constitute the niche for Lgr5 stem cells in intestinal crypts. Nature 469, 415-418.

Sato, T., Vries, R. G., Snippert, H. J., van de Wetering, M., Barker, N., Stange, D. E., van Es, J. H., Abo, A., Kujala, P., Peters, P. J., et al. (2009). Single Lgr5 stem cells build crypt-villus structures in vitro without a mesenchymal niche. Nature.

Shimazu, T., Hirschey, M. D., Newman, J., He, W., Shirakawa, K., Le Moan, N., Grueter, C. A., Lim, H., Saunders, L. R., Stevens, R. D., et al. (2013). Suppression of oxidative stress by beta-hydroxybutyrate, an endogenous histone deacetylase inhibitor. Science 339, 211-214.

Shoshkes-Carmel, M., Wang, Y. J., Wangensteen, K. J., Toth, B., Kondo, A., Massasa, E. E., Itzkovitz, S., and Kaestner, K. H. (2018). Author Correction: Subepithelial telocytes are an important source of Wnts that supports intestinal crypts. Nature 560, E29.

Shroyer, N. F., Helmrath, M. A., Wang, V. Y., Antalffy, B., Henning, S. J., and Zoghbi, H. Y. (2007). Intestine-specific ablation of mouse atonal homolog 1 (Math1) reveals a role in cellular homeostasis. Gastroenterology 132, 2478-2488.

Skarnes, W. C., Rosen, B., West, A. P., Koutsourakis, M., Bushell, W., Iyer, V., Mujica, A. O., Thomas, M., Harrow, J., Cox, T., et al. (2011). A conditional knockout resource for the genome-wide study of mouse gene function. Nature 474, 337-342.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Tian, H., Biehs, B., Chiu, C., Siebel, C. W., Wu, Y., Costa, M., de Sauvage, F. J., and Klein, O. D. (2015). Opposing activities of Notch and Wnt signaling regulate intestinal stem cells and gut homeostasis. Cell reports 11, 33-42.

Tinkum, K. L., Stemler, K. M., White, L. S., Loza, A. J., Jeter-Jones, S., Michalski, B. M., Kuzmicki, C., Pless, R., Stappenbeck, T. S., Piwnica-Worms, D., et al. (2015). Fasting protects mice from lethal DNA damage by promoting small intestinal epithelial stem cell survival. Proceedings of the National Academy of Sciences of the United States of America 112, E7148-7154.

van der Flier, L. G., van Gijn, M. E., Hatzis, P., Kujala, P., Haegebarth, A., Stange, D. E., Begthel, H., van den Born, M., Guryev, V., Oving, I., et al. (2009). Transcription factor achaete scute-like 2 controls intestinal stem cell fate. Cell 136, 903-912.

VanDussen, K. L., Carulli, A. J., Keeley, T. M., Patel, S. R., Puthoff, B. J., Magness, S. T., Tran, I. T., Maillard, I., Siebel, C., Kolterud, A., et al. (2012). Notch signaling modulates proliferation and differentiation of intestinal crypt base columnar stem cells. Development 139, 488-497.

Vooijs, M., Liu, Z., and Kopan, R. (2011). Notch: architect, landscaper, and guardian of the intestine. Gastroenterology 141, 448-459.

Wang, B., Rong, X., Palladino, E. N. D., Wang, J., Fogelman, A. M., Martin, M. G., Alrefai, W. A., Ford, D. A., and Tontonoz, P. (2018). Phospholipid Remodeling and Cholesterol Availability Regulate Intestinal Stemness and Tumorigenesis. Cell stem cell 22, 206-220 e204.

Wang, Q., Zhou, Y., Rychahou, P., Fan, T. W., Lane, A. N., Weiss, H. L., and Evers, B. M. (2017). Ketogenesis contributes to intestinal cell differentiation. Cell death and differentiation 24, 458-468.

Yamaguchi, M., Tonou-Fujimori, N., Komori, A., Maeda, R., Nojima, Y., Li, H., Okamoto, H., and Masai, I. (2005). Histone deacetylase 1 regulates retinal neurogenesis in zebrafish by suppressing Wnt and Notch signaling pathways. Development 132, 3027-3043.

Yan, K. S., Janda, C. Y., Chang, J., Zheng, G. X. Y., Larkin, K. A., Luca, V. C., Chia, L. A., Mah, A. T., Han, A., Terry, J. M., et al. (2017). Non-equivalence of Wnt and R-spondin ligands during Lgr5(+) intestinal stem-cell self-renewal. Nature 545, 238-242.

Yang, Q., Bermingham, N. A., Finegold, M. J., and Zoghbi, H. Y. (2001). Requirement of Math1 for secretory cell lineage commitment in the mouse intestine. Science 294, 2155-2158.

Yilmaz, O. H., Katajisto, P., Lamming, D. W., Gultekin, Y., Bauer-Rowe, K. E., Sengupta, S., Birsoy, K., Dursun, A., Yilmaz, V. O., Selig, M., et al. (2012). mTORC1 in the Paneth cell niche couples intestinal stem-cell function to calorie intake. Nature 486, 490-495.

Yin, X., Farin, H. F., van Es, J. H., Clevers, H., Langer, R., and Karp, J. M. (2014). Niche-independent high-purity cultures of Lgr5+ intestinal stem cells and their progeny. Nature methods 11, 106-112.

Zecchini, V., Domaschenz, R., Winton, D., and Jones, P. (2005). Notch signaling regulates the differentiation of post-mitotic intestinal epithelial cells. Genes & development 19, 1686-1691.

Zhang, M., Behbod, F., Atkinson, R. L., Landis, M. D., Kittrell, F., Edwards, D., Medina, D., Tsimelzon, A., Hilsenbeck, S., Green, J. E., et al. (2008). Identification of tumor-initiating cells in a p53-null mouse model of breast cancer. Cancer Res 68, 4674-4682.

Zhao, M., Chen, X., Gao, G., Tao, L., and Wei, L. (2009). RLEdb: a database of rate-limiting enzymes and their regulation in human, rat, mouse, yeast and E. coli. Cell research 19, 793-795.

Zimberlin, C. D., Lancini, C., Sno, R., Rosekrans, S. L., McLean, C. M., Vlaming, H., van den Brink, G. R., Bots, M., Medema, J. P., and Dannenberg, J. H. (2015). HDAC1 and HDAC2 collectively regulate intestinal stem cell homeostasis. FASEB journal: official publication of the Federation of American Societies for Experimental Biology 29, 2070-2080.

Juarez-Hernandez, R. E.; Franzblau, S. G.; Miller, M. J., Syntheses of mycobactin analogs as potent and selective inhibitors of Mycobacterium tuberculosis. Org. Biomol. Chem. 2012, 10, 7584-7593.

Seebach, D.; Brändli, U.; Schnurrenberger, P.; Przybylski, M., High-Yield Synthesis of 20-, 24-, and 28-Membered Macropentolide, -hexolide, and -heptolide, Respectively, from (R)- or (S)-3-hydroxybutanoic acid under Yamaguchi's macrolactonization conditions. *Helv. Chim. Acta* 1988, 71, 155-167.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A composition comprising β-hydroxybutyrate, or a pharmaceutically-acceptable salt thereof, or a 3-hydroxybutyrate ester derivative, or a pharmaceutically-acceptable salt thereof, encapsulated by a nanoparticle, wherein the nanoparticle comprises poly(lactic-co-glycolic acid) (PLGA).

2. The composition of claim 1, wherein the β-hydroxybutyrate is present in an oligomer comprising from 2 to about 2000 β-hydroxybutyrate monomers.

3. The composition of claim 2, wherein the oligomer is a cyclic oligomer or linear oligomer.

4. The composition of claim 1, further comprising a histone deacetylase (HDAC) inhibitor.

5. The composition of claim 1, wherein the 3-hydroxybutyrate ester derivative, or pharmaceutically-acceptable salt thereof, is glycerol-tri((R)-3-hydroxybutyrate), or a pharmaceutically-acceptable salt thereof.

* * * * *